United States Patent
Adler et al.

(10) Patent No.: US 10,093,718 B2
(45) Date of Patent: *Oct. 9, 2018

(54) T1R TASTE RECEPTORS AND GENES ENCODING SAME

(71) Applicant: Senomyx, Inc., San Diego, CA (US)

(72) Inventors: Jon Elliot Adler, Sherwood, OR (US); Sergey Zozulya, San Diego, CA (US); Xiaodong Li, San Diego, CA (US); Shawn O'Connell, Encinitas, CA (US); Lena Luukkonen, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,353

(22) Filed: Apr. 10, 2017

(65) Prior Publication Data

US 2017/0313761 A1 Nov. 2, 2017

Related U.S. Application Data

(60) Division of application No. 14/696,896, filed on Apr. 27, 2015, now Pat. No. 9,637,536, which is a division of application No. 13/600,377, filed on Aug. 31, 2012, now Pat. No. 9,040,247, which is a continuation of application No. 13/092,598, filed on Apr. 22, 2011, now Pat. No. 8,263,341, which is a division of application No. 12/392,143, filed on Feb. 25, 2009, now Pat. No. 8,815,525, which is a continuation of application No. 10/725,081, filed on Dec. 2, 2003, now Pat. No. 7,507,544, which is a division of application No. 09/799,629, filed on Mar. 7, 2001, now Pat. No. 7,244,835.

(60) Provisional application No. 60/195,536, filed on Apr. 7, 2000, provisional application No. 60/209,840, filed on Jun. 6, 2000, provisional application No. 60/214,213, filed on Jun. 23, 2000, provisional application No. 60/226,448, filed on Aug. 17, 2000, provisional application No. 60/259,227, filed on Jan. 3, 2001, provisional application No. 60/187,546, filed on Mar. 7, 2000.

(51) Int. Cl.
*G01N 33/566* (2006.01)
*C07K 14/705* (2006.01)
*C07K 14/72* (2006.01)

(52) U.S. Cl.
CPC .......... *C07K 14/723* (2013.01); *C07K 14/705* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,993,778 A | 11/1999 | Firestein et al. |
| 6,383,778 B1 | 5/2002 | Zuker et al. |
| 6,540,978 B1 | 4/2003 | Margolskee et al. |
| 6,558,910 B2 | 5/2003 | Zuker et al. |
| 6,955,887 B2 | 10/2005 | Adler et al. |
| 7,022,488 B2 | 4/2006 | Servant et al. |
| 7,208,290 B2 | 4/2007 | Li et al. |
| 7,223,551 B2 | 5/2007 | Adler et al. |
| 7,241,880 B2 | 7/2007 | Adler et al. |
| 7,244,584 B2 | 7/2007 | Zuker et al. |
| 7,244,835 B2 | 7/2007 | Adler et al. |
| 7,294,474 B2 | 11/2007 | Zoller et al. |
| 7,297,543 B2 | 11/2007 | Zoller et al. |
| 7,297,772 B2 | 11/2007 | Zoller et al. |
| 7,301,009 B2 | 11/2007 | Zoller et al. |
| 7,303,886 B2 | 12/2007 | Zoller et al. |
| 7,309,577 B2 | 12/2007 | Zoller et al. |
| 7,344,859 B2 | 3/2008 | Zoller et al. |
| 7,364,903 B2 | 4/2008 | Zoller et al. |
| 7,368,285 B2 | 5/2008 | Zoller et al. |
| 7,402,400 B2 | 7/2008 | Zuker et al. |
| 7,419,791 B2 | 9/2008 | Adler et al. |
| 7,435,552 B2 | 10/2008 | Adler et al. |
| 7,452,685 B2 | 11/2008 | Adler et al. |
| 7,459,277 B2 | 12/2008 | Erlenbach et al. |
| 7,465,550 B2 | 12/2008 | Zuker et al. |
| 7,476,399 B2 | 1/2009 | Tachdjian |
| 7,507,544 B2 | 3/2009 | Adler et al. |
| 7,507,793 B2 | 3/2009 | Zuker et al. |
| 7,524,637 B2 | 4/2009 | Adler et al. |
| 7,534,577 B2 | 5/2009 | Adler et al. |
| 7,588,900 B2 | 9/2009 | Zuker et al. |

(Continued)

FOREIGN PATENT DOCUMENTS

| | | |
|---|---|---|
| WO | 95/08627 | 3/1995 |
| WO | 00/06692 | 2/2000 |

(Continued)

OTHER PUBLICATIONS

Guo, et al., "Protein Tolerance to Random Amino Acid Change", PNAS, vol. 101, No. 25, pp. 9205-9210, Jun. 2004.
Nelson, et al., "Mammalian Sweet Taste Receptors", Cell, vol. 106, pp. 381-390, Aug. 10, 2001.
Database EMBL, Online, embl heidelberg; Acc# Ac062024. Jun. 21, 2000.
Nelson, et al., "An Amino-Acid Taste Receptor", Nature, vol. 416, pp. 199-202, Mar. 14, 2002.
Alexander, et al., "Altering the Antigenicity of Proteins", Proc. Natl. Acad. Sci. USA, vol. 89, pp. 3352-3366, Apr. 1992.

(Continued)

*Primary Examiner* — John D Ulm
(74) *Attorney, Agent, or Firm* — Robin L. Teskin; LeClairRyan PLLC

(57) ABSTRACT

Methods are provided for identifying human and non-human primate cells which respond to sweet tastants. These methods screen for human or non-human primate cells which express a polypeptide which binds to or responds to sweet tastants. These cells may be used in binding and functional assays to screen for compounds which modulate sweet taste.

15 Claims, 1 Drawing Sheet

Specification includes a Sequence Listing.

(56) References Cited

U.S. PATENT DOCUMENTS

| | | |
|---|---|---|
| 7,588,916 B2 | 9/2009 | Adler et al. |
| 7,601,513 B2 | 10/2009 | Zoller et al. |
| 7,655,422 B2 | 2/2010 | Adler et al. |
| 7,705,121 B2 | 4/2010 | Adler et al. |
| 7,737,254 B2 | 6/2010 | Adler et al. |
| 7,763,431 B1 | 7/2010 | Zoller et al. |
| 7,772,385 B2 | 8/2010 | Adler et al. |
| 7,781,181 B2 | 8/2010 | Adler et al. |
| 7,786,263 B2 | 8/2010 | Adler et al. |
| 7,790,848 B2 | 9/2010 | Adler et al. |
| 7,799,905 B2 | 9/2010 | Adler et al. |
| 7,834,165 B2 | 11/2010 | Adler et al. |
| 7,842,785 B2 | 11/2010 | Adler et al. |
| 7,847,080 B2 | 12/2010 | Adler et al. |
| 7,888,470 B2 | 2/2011 | Li et al. |
| 7,892,765 B2 | 2/2011 | Adler et al. |
| 7,906,328 B2 | 3/2011 | Zoller et al. |
| 7,906,627 B2 | 3/2011 | Li et al. |
| 7,910,322 B2 | 3/2011 | Zoller et al. |
| 7,927,823 B2 | 4/2011 | Adler et al. |
| 7,927,825 B2 | 4/2011 | Zoller et al. |
| 7,939,279 B2 | 5/2011 | Zuker et al. |
| 8,119,359 B2 | 2/2012 | Adler et al. |
| 8,168,401 B2 | 5/2012 | Zoller et al. |
| 8,198,048 B2 | 6/2012 | Zuker et al. |
| 8,206,938 B2 | 6/2012 | Zoller et al. |
| 8,222,019 B2 | 7/2012 | Zoller et al. |
| 8,247,184 B2 | 8/2012 | Li et al. |
| 8,247,542 B2 | 8/2012 | Adler et al. |
| 8,263,341 B2 | 9/2012 | Adler et al. |
| 8,314,224 B2 | 11/2012 | Adler et al. |
| 8,323,912 B2 | 12/2012 | Zoller et al. |
| 8,404,455 B2 | 3/2013 | Li et al. |
| 8,815,525 B2 * | 8/2014 | Adler .................. C07K 14/705 435/7.1 |
| 2002/0051997 A1 | 5/2002 | Zuker et al. |
| 2002/0061522 A1 | 5/2002 | Glucksmann et al. |
| 2002/0094551 A1 | 7/2002 | Adler et al. |
| 2002/0151052 A1 | 10/2002 | Chaudhari et al. |
| 2002/0160424 A1 | 10/2002 | Adler et al. |
| 2002/0168635 A1 | 11/2002 | Zuker et al. |
| 2003/0008344 A1 | 1/2003 | Adler et al. |
| 2003/0022278 A1 | 1/2003 | Zuker et al. |
| 2003/0022288 A1 | 1/2003 | Zuker et al. |
| 2003/0036089 A1 | 2/2003 | Wei et al. |
| 2003/0040045 A1 | 2/2003 | Zuker et al. |
| 2003/0054448 A1 | 3/2003 | Adler et al. |
| 2003/0166137 A1 | 9/2003 | Zuker et al. |
| 2003/0232407 A1 | 12/2003 | Zoller et al. |
| 2004/0086877 A1 | 5/2004 | Zuker et al. |
| 2004/0132075 A1 | 7/2004 | Elliot et al. |
| 2004/0171042 A1 | 9/2004 | Adler et al. |
| 2004/0175792 A1 | 9/2004 | Zoller et al. |
| 2004/0175793 A1 | 9/2004 | Zoller et al. |
| 2004/0185469 A1 | 9/2004 | Zoller et al. |
| 2004/0191805 A1 | 9/2004 | Adler et al. |
| 2004/0191862 A1 | 9/2004 | Zoller et al. |
| 2004/0209286 A1 | 10/2004 | Adler et al. |
| 2004/0229239 A1 | 11/2004 | Adler et al. |
| 2005/0032158 A1 | 2/2005 | Adler et al. |
| 2005/0084506 A1 | 4/2005 | Tachdjian |
| 2005/0084932 A1 | 4/2005 | Zoller et al. |
| 2005/0106571 A1 | 5/2005 | Erlenbach et al. |
| 2005/0260599 A1 | 11/2005 | Ryba et al. |
| 2005/0287517 A1 | 12/2005 | Adler et al. |
| 2006/0014208 A1 | 1/2006 | Zoller et al. |
| 2006/0045953 A1 | 3/2006 | Tachdjian |
| 2006/0127977 A1 | 6/2006 | Zoller et al. |
| 2006/0160176 A1 | 7/2006 | Zoller et al. |
| 2007/0104709 A1 | 5/2007 | Li et al. |
| 2007/0105159 A1 | 5/2007 | Erlenbach et al. |
| 2007/0161053 A1 | 7/2007 | Li et al. |
| 2007/0292944 A1 | 12/2007 | Adler et al. |
| 2008/0026404 A1 | 1/2008 | Adler et al. |
| 2008/0038741 A1 | 2/2008 | Adler et al. |
| 2008/0050778 A1 | 2/2008 | Zoller et al. |
| 2008/0085994 A1 | 4/2008 | Li et al. |
| 2008/0213880 A1 | 9/2008 | Adler et al. |
| 2008/0214784 A1 | 9/2008 | Adler et al. |
| 2008/0220451 A1 | 9/2008 | Adler et al. |
| 2008/0233596 A1 | 9/2008 | Adler et al. |
| 2008/0244761 A1 | 10/2008 | Zoller et al. |
| 2008/0244762 A1 | 10/2008 | Zoller et al. |
| 2008/0248996 A1 | 10/2008 | Zoller et al. |
| 2008/0248997 A1 | 10/2008 | Zoller et al. |
| 2008/0262087 A1 | 10/2008 | Zoller et al. |
| 2008/0318251 A1 | 12/2008 | Zuker et al. |
| 2009/0004676 A1 | 1/2009 | Adler et al. |
| 2009/0029455 A1 | 1/2009 | Adler et al. |
| 2009/0047736 A1 | 2/2009 | Adler et al. |
| 2009/0053730 A1 | 2/2009 | Adler et al. |
| 2009/0061458 A1 | 3/2009 | Adler et al. |
| 2009/0093051 A1 | 4/2009 | Adler et al. |
| 2009/0098579 A1 | 4/2009 | Adler et al. |
| 2009/0098580 A1 | 4/2009 | Zuker et al. |
| 2009/0111834 A1 | 4/2009 | Tachdjian |
| 2009/0155819 A1 | 6/2009 | Erlenbach et al. |
| 2009/0176657 A1 | 7/2009 | Adler et al. |
| 2009/0209731 A1 | 8/2009 | Zoller et al. |
| 2009/0215174 A1 | 8/2009 | Zoller et al. |
| 2009/0221000 A1 | 9/2009 | Zoller et al. |
| 2009/0221001 A1 | 9/2009 | Zoller et al. |
| 2009/0221002 A1 | 9/2009 | Zoller et al. |
| 2009/0221067 A1 | 9/2009 | Zoller et al. |
| 2009/0221709 A1 | 9/2009 | Zoller et al. |
| 2009/0221796 A1 | 9/2009 | Zoller et al. |
| 2009/0221797 A1 | 9/2009 | Zoller et al. |
| 2009/0233807 A1 | 9/2009 | Adler et al. |
| 2009/0275125 A1 | 11/2009 | Adler et al. |
| 2010/0075412 A1 | 3/2010 | Adler et al. |
| 2010/0033059 A1 | 12/2010 | Adler et al. |
| 2011/0081658 A1 | 4/2011 | Adler et al. |
| 2011/0151483 A1 | 6/2011 | Zuker et al. |

FOREIGN PATENT DOCUMENTS

| | | |
|---|---|---|
| WO | 00/06693 | 2/2000 |
| WO | 01/64882 | 9/2001 |
| WO | 01/66563 | 9/2001 |
| WO | 01/83749 | 11/2001 |
| WO | 02/064631 | 8/2002 |
| WO | 03/001876 | 1/2003 |
| WO | 03/004992 | 1/2003 |
| WO | 03/025137 | 3/2003 |
| WO | 05/015158 | 2/2005 |
| WO | 05/033125 | 4/2005 |
| WO | 05/041684 | 5/2005 |
| WO | 06/084246 | 8/2006 |

OTHER PUBLICATIONS

GenBank Accession No. AL 139287. clone RP5-89003, Feb. 13, 2000.
GenBank Accession No. AA907022, May 19, 1998.
Undemann B., "A taste for Umami", Nature Neuroscience, vol. 3, No. 2, pp. 99-100, Feb. 2000.
Temussi et al., J. Mol. Recognition, 19 (188-199) 2006.
Bowie et al., 1990, Science 247: 1306-1310.
Hoon, et al., Cell 96(541-551), 1999.
Krautwurst et al. Cell 95 (917-920), 1998.
Li et al., "Human Receptors for Sweet and Umami Taste", Proceedings of the National Academy of Sciences of USA, National Academy of Science, vol. 99, No. 7, Apr. 2, 2002, pp. 4692-4696—XP-002254830.
Waterson, R.H., Direct Submission, Genome Sequencing Center Apr. 21, 2000—XP 002262036.
Adler, et al., "A Novel Family of Mammalian Taste Receptors", Cell, vol. 100, pp. 693-702, Mar. 17, 2000—XP-000982340.
Montmayeur, et al., "A Candidate Taste Receptor Gene Near a Sweet Taste Locus", Nature Neuroscience, May 2001, pp. 492-498, vol. 4, No. 5, Nature America, Inc. US.

(56) References Cited

OTHER PUBLICATIONS

Max, et al., "Tas1r3, Encoding a New Candidate Taste Receptor is Allelic to the Sweet Responsiveness Locus Sac", Nature Genetics, May 2001, pp. 55-63, vol. 28, No. 1, Nature America, NY, US.
Sainz, et al., "Identification of Novel Member of the T1R Family of Purative Taste Receptors", Journal of Neurochemistry, May 2001, pp. 896-903, vol. 77, No. 3, NY, US.
Johnson, et al., "The Effect of the Sweetness Inhibitor 2(4-methoxyphenoxy) Propanoic Acid (Sodium Salt) (Na-PMP) on the Taste of Bitter-sweet Stimuli", Chemical Sense, Aug. 1994 pp. 349-358, vol. 19, No. 4, Oxford UK.
Akabas, MH: Dodd, J; Al-Awqati Q, (1998) A bitter substance induces a rise in intracellular calcium in a subpopulation of rat taste cells, Science 242: 1047-1050.
Akabas, MH, Dodd, J, Al-Awqati. Q, (1990) Identification of electrophysiologically distinct subpopulations of rat tasts cells. J. Membr. Biol. 114 71-78.
Avenet, P., Lindemann, B. (1987) Patch-clamp study of isolated taste receptor cells of the frog. J. Membr Biol 97:223-240.
Avenet, P.: Lindemann, B. (1989) Perspectives of taste reception, J Membrane Biol 112:1-8.
Behe, P.: DeSimone, J.A., Avenet, P.; Lindemann, B. (1990) Membrane currents in taste cells of the rat fungiform papillae: evidence for two types of Ca currents and inhibition of K currents by saccharin. J Gen Physiol 96: 1061-1084.
Bernhardt, S.J.; Naim, M.; Zehavi, U.; Lindemann, B. (1996) Changes in IP3 and cytosolic CA2+ in response to sugars and non-sugar sweeteners in transduction of sweet taste in the rat. J Physiol 490(P12):325-36.
Boughter, Jr., J.D.: Gilbertson, T.A. (1999) From channels to behavior: an integrative model of NaCl taste. Neuron 22:213-215.
Chen, Y.; Herness, M.S. (1997) Electrophysiological actions of quinine on voltage-dependent currents in dissociated rat taste cells. Pflugers Arch 434:215-226.
Chen, Y.; Sun, X-D: Herness, M.S. (1996) Characteristics of action potentials and their underlying outward currents in rat taste receptor cells. J Neurophysiol 75:820-831.
Cummings, T.A.; Daniels, C.: Kinnamon, S.C. (1996) Sweet taste transduction in hamster: sweeteners and cyclic nucleotides depolanzo taste cells by reducing a K+ current. J Neurophisiol 75: 1256-1263.
Erickson, R.P. (1968) Stimulus coding in topographic and nontopographic afferent modalities; on the significance of the activity of individual sensor neurons. Psychol Rev 75:447-465.
Frank, M.; Pfaffman, C. (1969) Taste nerve fibers: a random distribution of sensitivities to four tastes. Science 164:1183-1185.
Frank, M.E., Contreras, R.J., Hettinger, T.P. (1983) Nerve fibers sensitive to ionic taste stimuli in chorda tympani of the rat, J Neurophysiol 50:941-960.
Frank, M.E.; Bieber, S.L.; Smith, D.V. (1968) The organization of taste sensibilities in hamster chorda tympani nerve fibers. J Gen Physiol 91:861-896.
Furue, H.; Yoshii, K. (1997) In situ tight-seal recordings of taste substance elicited action currents and voltage-gated Ba currents from single taste buds cells in the pesied eplthelium of mouse tongue. Brain Res 776:133-139.
Furue, H., Yoshii, K. (1998) A method for in-situ tight-seal recordings from single taste bud cells of mice. J Neurosci Methods 84:109-114.
Gilbertson, T.A. (1995) Patch-clamping of taste cells in hamster and rat. In: Experimental cell biology of taste and olfaction current techniques and protocols (Spielman, A.I.: Brand, J.G., eds.), pp. 317-326, Boca Raton, FL: CRC.
Gilbertson, T.A.; Zhang, H. (1998) Characterization of sodium transport in gustatory epithelia from the hamster and rat. Chem senses 23:283-293.
Gilbertson, T.A.: Avenet, P.; Kinnamon, S.C., Roper, S.D. (1992) Proton currents through amitoride-sensitive Na channels in hamster cells role in acid transduction. J Gen Physiol 100:803-824.
Gilbertson, T.A.; Roper, S.D.; Kinnamon, S.C. (1993) Proton currents through amilcride-sensitive NA+ channels in isolated hamster taste cells: enhancement by vasopressin and cAMP. Neuron 10:931-942.
Gilbertson, T.A.; Fontenot, D.T.; Zhang, H.; Liu, L. Monroe, W.T. (1997) Fatty acid modulation of K+ channels in taste receptor cells: gustatory cues for dietary fat, Am J Physiol 272(4 Pt 1):C1203-C1210.
Gilbertson, T.A.; Zhang, H.: Boughter, Jr., J.D.; Smith, D.V. (1999) Multiple sensitivity of rat fungi form taste cells, whole cell responses to apical chemical stimulation. Chem Senses 24 569.
Gilbertson, T.A.: Boughter, Jr., J.D., Zhang, H.; Smith, D.V. (2001) Distribution of gustatory sensitivities in rat taste cells; whole-coil responses to epical chemical stimulation, J Neurosci 21:4931-4951.
Herness, M.S.; Gilbertson, T.A. (1999) Cellular mechanisms of taste transduction. Annu Rev Physiol 61:873-900.
Herness, M.S.; Sun, X-D (1995) Voltage-dependent sodium currents recorded from dissociated rat taste cells. J. Membr Biol 146:73-84.
Kimura, K.; Beidler, L.M. (1961) Microelectrode study of tast receptor of rat and hamster. J Cell Comp Physiol 58:131-140.
Kinnamon, S. (1988) Taste transduction: a diversity of mechanisms. Trends Neurosci 11:491-496.
Kinnamon, S.; Divonne, V.F., Beam, K.G. (1988) Apical localization of K+ channels in taste cells provides the basis of sour taste transduction. Proc. natl Acad Sci USA 85:7023-7027.
Lindemann, B. (1996) Taste reception. Physiol Rev 76: 719-765.
MacKay-Sim A.; Delay, R.J.; Roper, S.D.; Kinnamon, S.C. (1996) Development of voltage-dependent currents in taste receptor cells. J Comp Neurol 365:278-288.
Monroe, W.T.; Smith, D.V.; Gilbertson, T.A. (1996) The MU chamber: a new method to record electrophysiological responses of taste receptor cells to gustatory stimuli. Chem Senses 21:644-645.
Ogawa, H.; Sato, M.; Yamashita, S. (1968) Multiple sensitivity of chorda tympani fibres of the rat and hamster to gustatory and thermal stimuli. J Physiol (Lond) 199:223-240.
Ohtubo, Y.; Suemitsu, T.; Shobara, S.; Matumoto, T.; Kumazawa, T., Yoshii, K. (2001) Optical recordings of taste responses from fungiform papillae of mouse in situ. J Physiol (Lond) 530:287-293.
Ozeki, M.; Sato, M. (1972) Responses of gustatory cells in the tongue of rat to stimuli representing four taste qualities. Comp Biochem Physiol [A] 41:391-407.
Pfaffman, C. (1955) Gustatory nerve impulses in rat, cat, and rabbit. J Neurophysiol 18:429-440.
Pfaffman, C. (1959) The afferent code for sensory quality. Am Psychol 14:226-232.
Roper, S.D. (1993) Synaptic interactions in taste buds. In: Mechanisms of taste transduction (Simon, S.A.; Roper, S.D., eds.), pp. 275-293. Boca Raton, FL: CRC.
Roper, S.D.; McBride, Jr, D.W. (1989) Distribution of ion channels on taste cells and its relationship to chemosensory transduction. J Membr. Biol 109:29-39.
Sato, T.; Beidler, L.M. (1982) The response characteristics of rat taste cells to four basic taste stimuli. Comp Biochem Physiol A 73:1-10.
Sato, T.; Beidler, L.M. (1997) Broad tuning of rat taste cells to four basic taste stimuli. Chem Senses 22:287-293.
Seto, E., Hayashi, Y.; Mori, T. (1999) Patch clamp recording of the responses to three bitter stimuli in mouse taste cells. Cell Mol Biol 45:317-325.
Smith, D.V.; Frank, M.E. (1993) Sensory coding by peripheral taste fibers. In: Mechanisms of Taste Transduction (Simon, S.A.; Roper, S.D., eds.), pp. 295-338. Boca Raton, FL: CRC.
Smith, D.V., St. John, S.J. (1999) Neural coding of gustatory information. Curr Opin Neurobiol 9:427-435.
Smith, D.V., Travers, J.B. (1979) A metric for the breadth of tuning of gustatory neurons. Chem Senses Flav 4:215-229.
Smith, D.V.: Van Buskirk, R.L., Travers, J.B.: Bieber, S.L. (1983) Coding of taste stimuli by hamster brain stem neurons, J. Neurophysiol 50:541-558.
Smith, D.V.; Zhang, H.; Boughter, Jr., J.D.; St. John, S.J.; Gilbertson, T.A. (2000) Random distribution of gustatory sensitivities across rat taste receptor cells and brainstem neurons. Chem Senses 25:661.

(56) References Cited

OTHER PUBLICATIONS

Spector, A.C.; Markison, S.; St. John, S.J.; Garcea, M. (1997) Sucrose vs. maltose taste discrimination by rats depends on the input of the seventh cranial nerve. Am J Physiol 272 (4 Pt 2):R1210-R1218.

Sweazey, R.D.; Smith, D.V. (1987) Convergence onto hamster madulary taste neurons. Brain Res 408: 173-184.

Tonosaki, K.; Funakoshi, M. (1984) Intracellular taste cell responses of mouse. Comp Biochem Physiol [A] 78:651-665.

Travers, J.B.; Smith, D.V. (1979) Gustatory sensitivities in neurons of the hamster nucleus tractus solitarius. Sens Processes 3:1-26.

Travers, S.P. (1993) Orosensory processing in neural systems of the nucleus of the solitary tract. In: Mechanisms of taste transduction (Simon, S.A.; Roper, S.D., eds.), pp. 339-394. Boca Raton, FL: CRC.

Van Buskirk, R.L.; Smith, D.V. (1981) Taste sensitivity of hamster parabrachial pontine neurons. J Neurophysiol 45:144-171.

Wong, G.T.; Gannon, K.S.; Margolskee, R.F. (1996) Transduction of bitter and sweet taste by gusducin. Nature 381:796-800.

Yamamoto, T.; Yuyama, N.; Kato, T.; Kawamura, Y. (1984) Gustatory responses of cortical neurons in rats. I. Response characteristics J Neurophysiol 61:616-635.

Han, G.; Hampson, D.R. (1999) Ligand binding to the amino-terminal domain of the mGluR4 subtype of metaborrapic glutamate receptor. J Biol Chem 274(15):10008-13.

Bonigk, W. et al., "The Native Rat Olfactory Cyclic Nucleotide-Gated Channel is Composed of Three Distinct Subunits", The Journal of Neuroscience, vol. 19, No. 136, p. 5332-5347 Jul. 1, 1999.

Damak, S., "Detection of Sweet and Umami Taste in the Absence of Taste Receptor T1r3", Science, vol. 301, pp. 850-853, 2003.

European Search Report for European Appl. No. 08153652.6, dated Jan. 21, 2009.

Extended European Search Report and Opinion for European Application No. 08075748.7, dated Nov. 21, 2008.

Hayashi, "Effects of Ionic Compositions of the Medium on Monosodium Glutamate Binding to Taste Epithelial Cells", Biosci. Biotechnol. Biochem., 1999, 63(3):480-484.

Kinnamon, S. and Cummings, T., "Chemosensory Transduction Mechanisms in Taste", Annu. Rev. Physiol., vol. 54, p. 715-731, 1992.

Kitagawa, M., et al., "Molecular Genetic Identification of a Candidate Receptor Gene for Sweet Taste", Biochemical and Biophysical Research Communications, vol. 283, p. 236-242, 2001.

Perruccio, et al., "Possible Role for gustductin in Taste Transduction in Hirudo Medicinalls", Society for Neuroscience Abstracts, vol. 26, No. 1-2, Abstract No. 66. 15, 2000.

Alla et al., Extracellular Domain of the Bradykinin B2 Receptor Involved in Ligand Binding and Agonist Sensing Defined by Anti-peptide Antibodies, Jan. 19, 1996, The Journal of Biological Chemistry 271(3):1748-1755.

Elies et al., Immunochemical and Functional Characterization of an Agonist-like Monoclonal Antibody Against the M2 Acetylcholine Receptor, Feb. 1, 1998, European Journal of Biochemistry 251(3):659-666.

Hoon et al., Putative Mammalian Taste Receptors: A Class of Taste-Specific GPCRs with Distinct Topographic Selectivity, Feb. 19, 1999, Cell 96:541-551.

Jiang P., et al. "Lactisole interacts with the transmembrane domains of human T1 R3 to inhibit sweet taste," J Biol Chem. Apr. 15, 2005;280(15):15238-46.

Lebesque et al., An Agonist-like Monoclonal Antibody Against the beta2-adrenoreceptor, May 1, 1998, European Journal of Pharmacology 348(1):123-133.

Xu H, et al. "Different functional roles of T1R subunits in the heteromeric taste receptors," Proc Natl Acad Sci U S A. Sep. 28, 2004;101(39):14258-63.

\* cited by examiner

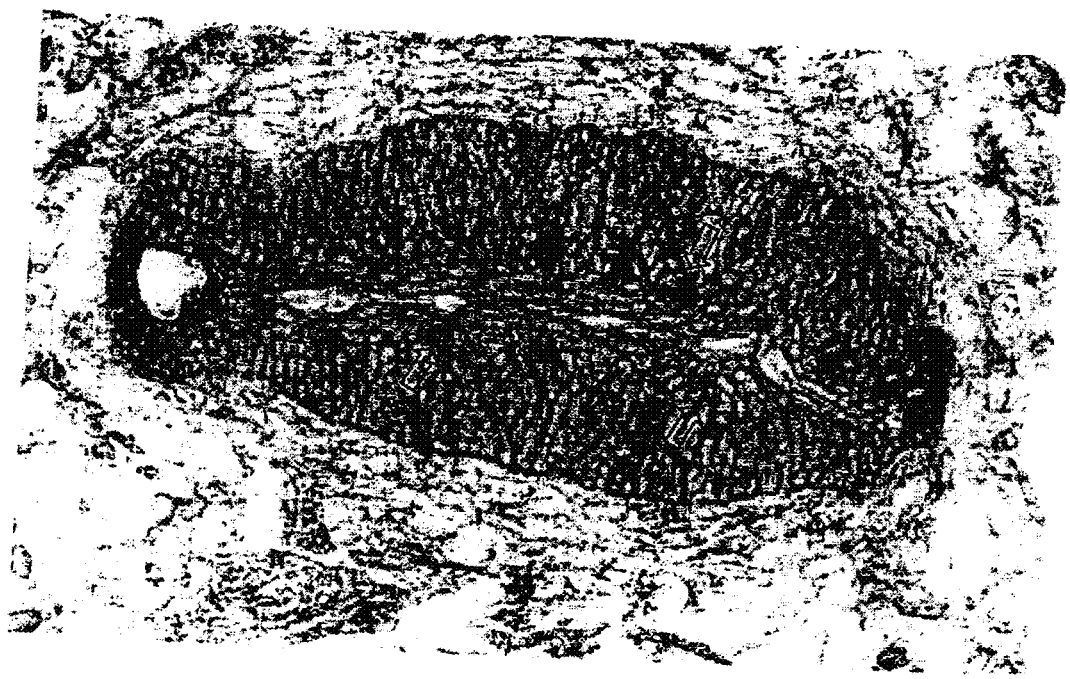

SEQUENCE LISTING

<160> NUMBER OF SEQ ID NOS: 20

<210> SEQ ID NO 1
<211> LENGTH: 876
<212> TYPE: DNA
<213> ORGANISM: Homo sapiens

<400> SEQUENCE: 1

```
agcctggcag tggcctcagg cagagtctga cgcgcacaaa ctttcaggcc caggaagcga      60
ggacaccact ggggcccag ggtgtggcaa gtgaggatgg caagggtttt gctaaacaaa      120
tcctctgccc gctccccgcc ccgggctcac tccatgtgag gccccagtcg ggcagccac      180
ctgccgtgcc tgttggaagt tgcctctgcc atgctgggcc ctgctgtcct gggcctcagc      240
ctctgggctc tcctgcaccc tgggacgggg gccccattgt gcctgtcaca gcaacttagg      300
atgaagggg actacgtgct gggggggctg ttccccctgg gcgaggccga ggaggctggc      360
ctccgcagcc ggacacggcc cagcagccct gtgtgcacca ggtacagagg tgggacggcc      420
tgggtcgggg tcagggtgac caggtctggg gtgctcctga gctggggccg aggtggccat      480
ctgcggttct gtgtggcccc aggttctcct caaacggcct gctctgggca ctggccatga      540
aaatggccgt ggaggagatc aacaacaagt cggatctgct gcccgggctg cgcctgggct      600
acgacctctt tgatacgtgc tcggagcctg tggtggccat gaagcccagc ctcatgttcc      660
tggccaaggc aggcagccgc gacatcgccg cctactgcaa ctacacgcag taccagcccc      720
gtgtgctggc tgtcatcggg ccccactcgt cagagctcgc catggtcacc ggcaagttct      780
tcagcttctt cctcatgccc cagtggggcg ccccccacca tcacccaccc ccaaccaacc      840
cctgccccgt gggagcccct tgtgtcagga gaatgc                                 876
```

<210> SEQ ID NO 2
<211> LENGTH: 2687

```
<212> TYPE: DNA
<213> ORGANISM: Homo sapiens

<400> SEQUENCE: 2
tacatgcacc ccacccagcc ctgccctggg agccctgtgt cagaagatgc tcttggcctt      60
gcaggtcagc tacggtgcta gcatggagct gctgagcgcc cgggagacct tcccctcctt     120
cttccgcacc gtgcccagcg accgtgtgca gctgacggcc gccgcggagc tgctgcagga     180
gttcggctgg aactgggtgg ccgccctggg cagcgacgac gagtacgcc ggcagggcct      240
gagcatcttc tcggccctgg ccgcggcacg cggcatctgc atcgcgcacg agggcctggt     300
gccgctgccc cgtgccgatg actcgcggct ggggaaggtg caggacgtcc tgcaccaggt     360
gaaccagagc agcgtgcagg tggtgctgct gttcgcctcc gtgcacgccg cccacgccct     420
cttcaactac agcatcagca gcaggctctc gcccaaggtg tgggtggcca gcgaggcctg     480
gctgacctct gacctggtca tggggctgcc cggcatggcc cagatgggca cggtgcttgg     540
cttcctccag aggggtgccc agctgcacga gttcccccag tacgtgaaga cgcacctggc     600
cctggccacc gacccggcct tctgctctgc cctgggcgag agggagcagg gtctggagga     660
ggacgtggtg ggccagcgct gcccgcagtg tgactgcatc acgctgcaga acgtgagcgc     720
agggctaaat caccaccaga cgttctctgt ctacgcagct gtgtatagcg tggcccaggc     780
cctgcacaac actcttcagt gcaacgcctc aggctgcccc gcgcaggacc ccgtgaagcc     840
ctggcaggtg agcccgggag atgggggtgt gctgtcctct gcatgtgccc aggccaccag     900
gcacggccac cacgcctgag ctggaggtgg ctggcggctc agcccgtcc cccgcccgca      960
gctcctggag aacatgtaca acctgacctt ccacgtgggc gggctgccgc tgcggttcga    1020
cagcagcgga aacgtggaca tggagtacga cctgaagctg tgggtgtggc agggctcagt    1080
gcccaggctc cacgacgtgg gcaggttcaa cggcagcctc aggacagagc gcctgaagat    1140
ccgctggcac acgtctgaca accaggtgag gtgagggtgg gtgtgccagg cgtgcccgtg    1200
gtagcccccg cggcagggcg cagcctgggg gtgggggccg ttccagtctc ccgtgggcat    1260
gcccagccga gcagagccag accccaggcc tgtgcgcaga agcccgtgtc ccggtgctcg    1320
cggcagtgcc aggagggcca ggtgcgccgg gtcaaggggt tccactcctg ctgctacgac    1380
tgtgtggact gcgaggcggg cagctaccgg caaaacccag gtgagccgcc ttcccggcag    1440
gcgggggtgg gaacgcagca ggggagggtc ctgccaagtc ctgactctga gaccagagcc    1500
cacagggtac aagacgaaca cccagcgccc ttctcctctc tcacagacga catcgcctgc    1560
accttttgtg gccaggatga gtggtccccg gagcgaagca cacgctgctt ccgccgcagg    1620
tctcggttcc tggcatgggg cgagccggct gtgctgctgc tgctcctgct gctgagcctg    1680
gcgctgggcc ttgtgctggc tgctttgggg ctgttcgttc accatcggga cagcccactg    1740
gttcaggcct cgggggggcc cctggcctgc tttggcctgg tgtgcctggg cctggtctgc    1800
ctcagcgtcc tcctgttccc tggccagccc agccctgccc gatgcctggc ccagcagccc    1860
ttgtcccacc tcccgctcac gggctgcctg agcacactct tcctgcaggc ggccgagatc    1920
ttcgtggagt cagaactgcc tctgagctgg gcagaccggc tgagtggctg cctgcggggg    1980
ccctgggcct ggctggtggt gctgctggcc atgctgtgtg aggtcgcact gtgcacctgg    2040
tacctggtgg ccttcccgcc ggaggtggtg acggactggc acatgctgcc cacggaggcg    2100
ctggtgcact gccgcacacg ctcctgggtc agcttcggcc tagcgcacgc caccaatgcc    2160
acgctggcct ttctctgctt cctgggcact ttcctggtgc ggagccagcc gggctgctac    2220
```

| | |
|---|---:|
| aaccgtgccc gtggcctcac cttttgccatg ctggcctact tcatcacctg gtctcctttt | 2280 |
| gtgcccctcc tggccaatgt gcaggtggtc ctcaggcccg ccgtgcagat gggcgccctc | 2340 |
| ctgctctgtg tcctgggcat cctggctgcc ttccacctgc ccaggtgtta cctgctcatg | 2400 |
| cggcagccag ggctcaacac ccccgagttc ttcctgggag ggggccctgg ggatgcccaa | 2460 |
| ggccagaatg acgggaacac aggaaatcag gggaaacatg agtgacccaa ccctgtgatc | 2520 |
| tcagccccgg tgaacccaga cttagctgcg atccccccca agccagcaat gacccgtgtc | 2580 |
| tcgctacaga gaccctcccg ctctaggttc tgaccccagg ttgtctcctg accctgaccc | 2640 |
| cacagtgagc cctaggcctg gagcacgtgg acacccctgt gaccatc | 2687 |

<210> SEQ ID NO 3
<211> LENGTH: 2553
<212> TYPE: DNA
<213> ORGANISM: Homo sapiens

<400> SEQUENCE: 3

| | |
|---|---:|
| atgctgggcc ctgctgtcct gggcctcagc ctctgggctc tcctgcaccc tgggacgggg | 60 |
| gccccattgt gcctgtcaca gcaacttagg atgaaggggg actacgtgct ggggggggctg | 120 |
| ttcccccctgg gcgaggccga ggaggctggc ctccgcagcc ggacacggcc cagcagccct | 180 |
| gtgtgcacca ggttctcctc aaacggcctg ctctgggcac tggccatgaa atggccgtg | 240 |
| gaggagatca caacaagtc ggatctgctg cccgggctgc cctgggcta cgacctcttt | 300 |
| gatacgtgct cggagcctgt ggtggccatg aagcccagcc tcatgttcct ggccaaggca | 360 |
| ggcagccgcg acatcgccgc ctactgcaac tacacgcagt accagccccg tgtgctggct | 420 |
| gtcatcgggc cccactcgtc agagctcgcc atggtcaccg gcaagttctt cagcttcttc | 480 |
| ctcatgcccc actacggtgc tagcatggag ctgctgagcg cccgggagac cttcccctcc | 540 |
| ttcttccgca ccgtgcccag cgaccgtgtg cagctgacgg ccgccgcgga gctgctgcag | 600 |
| gagttcggct ggaactgggt ggccgccctg ggcagcgacg acgagtacgg ccggcagggc | 660 |
| ctgagcatct tctcggccct ggccgcggca cgcggcatct gcatcgcgca cgagggcctg | 720 |
| gtgccgctgc cccgtgccga tgactcgcgg ctggggaagg tgcaggacgt cctgcaccag | 780 |
| gtgaaccaga gcagcgtgca ggtggtgctg ctgttcgcct ccgtgcacgc cgcccacgcc | 840 |
| ctcttcaact acagcatcag cagcaggctc tcgcccaagg tgtgggtggc cagcgaggcc | 900 |
| tggctgacct ctgacctggt catggggctg cccggcatgg cccagatggg cacggtgctt | 960 |
| ggcttcctcc agaggggtgc ccagctgcac gagttccccc agtacgtgaa gacgcacctg | 1020 |
| gccctggcca ccgacccggc cttctgctct gccctgggcg agagggagca gggtctggag | 1080 |
| gaggacgtgg tgggccagcg ctgccgcag tgtgactgca tcacgctgca gaacgtgagc | 1140 |
| gcagggctaa atcaccacca gacgttctct gtctacgcag ctgtgtatag cgtggcccag | 1200 |
| gccctgcaca acactcttca gtgcaacgcc tcaggctgcc ccgcgcagga ccccgtgaag | 1260 |
| ccctggcagc tcctggagaa catgtacaac ctgaccttcc acgtgggcgg gctgccgctg | 1320 |
| cggttcgaca gcagcggaaa cgtggacatg gagtacgacc tgaagctgtg ggtgtggcag | 1380 |
| ggctcagtgc ccaggctcca cgacgtgggc aggttcaacg gcagcctcag acagagcgc | 1440 |
| ctgaagatcc gctggcacac gtctgacaac cagaagcccg tgtccggtg ctcgcggcag | 1500 |
| tgccaggagg ccaggtgcg ccgggtcaag gggttccact cctgctgcta cgactgtgtg | 1560 |
| gactgcgagg cgggcagcta ccggcaaaac ccagacgaca tcgcctgcac cttttgtggc | 1620 |
| caggatgagt ggtcccccga gcgaagcaca cgctgcttcc gccgcaggtc tcggttcctg | 1680 |

-continued

```
gcatggggcg agccggctgt gctgctgctg ctcctgctgc tgagcctggc gctgggcctt    1740
gtgctggctg ctttggggct gttcgttcac catcgggaca gcccactggt tcaggcctcg    1800
ggggggcccc tggcctgctt tggcctggtg tgcctgggcc tggtctgcct cagcgtcctc    1860
ctgttccctg gccagcccag ccctgcccga tgcctggccc agcagccctt gtcccacctc    1920
ccgctcacgg gctgcctgag cacactcttc ctgcaggcgg ccgagatctt cgtggagtca    1980
gaactgcctc tgagctgggc agaccggctg agtggctgcc tgcgggggcc ctgggcctgg    2040
ctggtggtgc tgctggccat gctggtggag gtcgcactgt gcacctggta cctggtggcc    2100
ttcccgccgg aggtggtgac ggactggcac atgctgccca cggaggcgct ggtgcactgc    2160
cgcacacgct cctgggtcag cttcggccta gcgcacgcca ccaatgccac gctggccttt    2220
ctctgcttcc tgggcacttt cctggtgcgc agccagccgg gctgctacaa ccgtgcccgt    2280
ggcctcacct ttgccatgct ggcctacttc atcacctggg tctcctttgt gcccctcctg    2340
gccaatgtgc aggtggtcct caggcccgcc gtgcagatgg gcgccctcct gctctgtgtc    2400
ctgggcatcc tggctgcctt ccacctgccc aggtgttacc tgctcatgcg gcagccaggg    2460
ctcaacaccc ccgagttctt cctgggaggg ggccctgggg atgcccaagg ccagaatgac    2520
gggaacacag gaaatcaggg gaaacatgag tga                                 2553
```

<210> SEQ ID NO 4
<211> LENGTH: 850
<212> TYPE: PRT
<213> ORGANISM: Homo sapiens

<400> SEQUENCE: 4

```
Met Leu Gly Pro Ala Val Leu Gly Leu Ser Leu Trp Ala Leu Leu His
 1               5                  10                  15

Pro Gly Thr Gly Ala Pro Leu Cys Leu Ser Gln Gln Leu Arg Met Lys
             20                  25                  30

Gly Asp Tyr Val Leu Gly Gly Leu Phe Pro Leu Gly Glu Ala Glu Glu
         35                  40                  45

Ala Gly Leu Arg Ser Arg Thr Arg Pro Ser Ser Pro Val Cys Thr Arg
     50                  55                  60

Phe Ser Ser Asn Gly Leu Leu Trp Ala Leu Ala Met Lys Met Ala Val
 65                  70                  75                  80

Glu Glu Ile Asn Asn Lys Ser Asp Leu Leu Pro Gly Leu Arg Leu Gly
                 85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro His Tyr Gly Ala Ser Met Glu Leu Leu Ser Ala Arg Glu
                165                 170                 175

Thr Phe Pro Ser Phe Phe Arg Thr Val Pro Ser Asp Arg Val Gln Leu
            180                 185                 190

Thr Ala Ala Ala Glu Leu Leu Gln Glu Phe Gly Trp Asn Trp Val Ala
        195                 200                 205

Ala Leu Gly Ser Asp Asp Glu Tyr Gly Arg Gln Gly Leu Ser Ile Phe
```

```
                210                 215                 220
Ser Ala Leu Ala Ala Ala Arg Gly Ile Cys Ile Ala His Glu Gly Leu
225                 230                 235                 240

Val Pro Leu Pro Arg Ala Asp Asp Ser Arg Leu Gly Lys Val Gln Asp
                245                 250                 255

Val Leu His Gln Val Asn Gln Ser Ser Val Gln Val Val Leu Leu Phe
                260                 265                 270

Ala Ser Val His Ala Ala His Ala Leu Phe Asn Tyr Ser Ile Ser Ser
            275                 280                 285

Arg Leu Ser Pro Lys Val Trp Val Ala Ser Glu Ala Trp Leu Thr Ser
            290                 295                 300

Asp Leu Val Met Gly Leu Pro Gly Met Ala Gln Met Gly Thr Val Leu
305                 310                 315                 320

Gly Phe Leu Gln Arg Gly Ala Gln Leu His Glu Phe Pro Gln Tyr Val
                325                 330                 335

Lys Thr His Leu Ala Leu Ala Thr Asp Pro Ala Phe Cys Ser Ala Leu
            340                 345                 350

Gly Glu Arg Glu Gln Gly Leu Glu Glu Asp Val Val Gly Gln Arg Cys
            355                 360                 365

Pro Gln Cys Asp Cys Ile Thr Leu Gln Asn Val Ser Ala Gly Leu Asn
370                 375                 380

His His Gln Thr Phe Ser Val Tyr Ala Ala Val Tyr Ser Val Ala Gln
385                 390                 395                 400

Ala Leu His Asn Thr Leu Gln Cys Asn Ala Ser Gly Cys Pro Ala Gln
                405                 410                 415

Asp Pro Val Lys Pro Trp Gln Leu Leu Glu Asn Met Tyr Asn Leu Thr
            420                 425                 430

Phe His Val Gly Gly Leu Pro Leu Arg Phe Asp Ser Ser Gly Asn Val
            435                 440                 445

Asp Met Glu Tyr Asp Leu Lys Leu Trp Val Trp Gln Gly Ser Val Pro
450                 455                 460

Arg Leu His Asp Val Gly Arg Phe Asn Gly Ser Leu Arg Thr Glu Arg
465                 470                 475                 480

Leu Lys Ile Arg Trp His Thr Ser Asp Asn Gln Lys Pro Val Ser Arg
                485                 490                 495

Cys Ser Arg Gln Cys Gln Glu Gly Gln Val Arg Val Lys Gly Phe
                500                 505                 510

His Ser Cys Cys Tyr Asp Cys Val Asp Cys Glu Ala Gly Ser Tyr Arg
            515                 520                 525

Gln Asn Pro Asp Asp Ile Ala Cys Thr Phe Cys Gly Gln Asp Glu Trp
            530                 535                 540

Ser Pro Glu Arg Ser Thr Arg Cys Phe Arg Arg Arg Ser Arg Phe Leu
545                 550                 555                 560

Ala Trp Gly Glu Pro Ala Val Leu Leu Leu Leu Leu Leu Ser Leu
                565                 570                 575

Ala Leu Gly Leu Val Leu Ala Ala Leu Gly Leu Phe Val His His Arg
            580                 585                 590

Asp Ser Pro Leu Val Gln Ala Ser Gly Gly Pro Leu Ala Cys Phe Gly
            595                 600                 605

Leu Val Cys Leu Gly Leu Val Cys Leu Ser Val Leu Leu Phe Pro Gly
            610                 615                 620

Gln Pro Ser Pro Ala Arg Cys Leu Ala Gln Gln Pro Leu Ser His Leu
625                 630                 635                 640
```

```
Pro Leu Thr Gly Cys Leu Ser Thr Leu Phe Leu Gln Ala Ala Glu Ile
                645                 650                 655

Phe Val Glu Ser Glu Leu Pro Leu Ser Trp Ala Asp Arg Leu Ser Gly
            660                 665                 670

Cys Leu Arg Gly Pro Trp Ala Trp Leu Val Val Leu Leu Ala Met Leu
        675                 680                 685

Val Glu Val Ala Leu Cys Thr Trp Tyr Leu Val Ala Phe Pro Pro Glu
690                 695                 700

Val Val Thr Asp Trp His Met Leu Pro Thr Glu Ala Leu Val His Cys
705                 710                 715                 720

Arg Thr Arg Ser Trp Val Ser Phe Gly Leu Ala His Ala Thr Asn Ala
                725                 730                 735

Thr Leu Ala Phe Leu Cys Phe Leu Gly Thr Phe Leu Val Arg Ser Gln
            740                 745                 750

Pro Gly Cys Tyr Asn Arg Ala Arg Gly Leu Thr Phe Ala Met Leu Ala
        755                 760                 765

Tyr Phe Ile Thr Trp Val Ser Phe Val Pro Leu Leu Ala Asn Val Gln
770                 775                 780

Val Val Leu Arg Pro Ala Val Gln Met Gly Ala Leu Leu Leu Cys Val
785                 790                 795                 800

Leu Gly Ile Leu Ala Ala Phe His Leu Pro Arg Cys Tyr Leu Leu Met
                805                 810                 815

Arg Gln Pro Gly Leu Asn Thr Pro Glu Phe Phe Leu Gly Gly Gly Pro
            820                 825                 830

Gly Asp Ala Gln Gly Gln Asn Asp Gly Asn Thr Gly Asn Gln Gly Lys
        835                 840                 845

His Glu
    850

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown
<220> FEATURE:
<221> NAME/KEY: modified_base
<222> LOCATION: (12)
<223> OTHER INFORMATION: a, c, t, g, other or unknown
<220> FEATURE:
<221> NAME/KEY: modified_base
<222> LOCATION: (18)
<223> OTHER INFORMATION: a, c, t, g, other or unknown

<400> SEQUENCE: 5
cgnttyytng cntggggnga rcc                                           23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
       primer
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (18)
<223> OTHER INFORMATION: a, c, t, g, other or unknown
<220> FEATURE:
<221> NAME/KEY: modified_base
<222> LOCATION: (21)
<223> OTHER INFORMATION: a, c, t, g, other or unknown

<400> SEQUENCE: 6
cgngcncgrt trtarcancc ngg                                          23

<210> SEQ ID NO 7
<211> LENGTH: 9
<212> TYPE: PRT
<213> ORGANISM: Homo sapiens

<400> SEQUENCE: 7

Arg Phe Leu Ala Trp Gly Glu Pro Ala
 1               5

<210> SEQ ID NO 8
<211> LENGTH: 8
<212> TYPE: PRT
<213> ORGANISM: Homo sapiens

<400> SEQUENCE: 8

Pro Gly Cys Tyr Asn Arg Ala Arg
 1               5

<210> SEQ ID NO 9
<211> LENGTH: 552
<212> TYPE: DNA
<213> ORGANISM: Mus sp.

<400> SEQUENCE: 9
gtgctgtcac tcctcctgct gctttgcctg gtgctgggtc tagcactggc tgctctgggg    60
ctctctgtcc accactggga cagccctctt gtccaggcct caggcggctc acagttctgc   120
tttggcctga tctgcctagg cctcttctgc ctcagtgtcc ttctgttccc aggacggcca   180
agctctgcca gctgccttgc acaacaacca atggctcacc tccctctcac aggctgcctg   240
agcacactct tcctgcaagc agctgagacc tttgtggagt ctgagctgcc actgagctgg   300
gcaaactggc tatgcagcta ccttcgggac tctggcctgc tagtggtact gttggccact   360
tttgtggagg cagcactatg tgcctggtat ttgaccgctt caccagaagt ggtgacagac   420
tggtcagtgc tgcccacaga ggtactggag cactgccacg tgcgttcctg ggtcaacctg   480
ggcttggtgc acatcaccaa tgcaatggta gcttttctct gctttctggg cactttcctg   540
gtacaagacc ag                                                      552

<210> SEQ ID NO 10
<211> LENGTH: 184
<212> TYPE: PRT
<213> ORGANISM: Mus sp.

<400> SEQUENCE: 10
```

Val Leu Ser Leu Leu Leu Leu Cys Leu Val Leu Gly Leu Ala Leu
1               5                   10                  15

Ala Ala Leu Gly Leu Ser Val His His Trp Asp Ser Pro Leu Val Gln
            20                  25                  30

Ala Ser Gly Gly Ser Gln Phe Cys Phe Gly Leu Ile Cys Leu Gly Leu
        35                  40                  45

Phe Cys Leu Ser Val Leu Leu Phe Pro Gly Arg Pro Ser Ser Ala Ser
    50                  55                  60

Cys Leu Ala Gln Gln Pro Met Ala His Leu Pro Leu Thr Gly Cys Leu
65                  70                  75                  80

Ser Thr Leu Phe Leu Gln Ala Ala Glu Thr Phe Val Glu Ser Glu Leu
                85                  90                  95

Pro Leu Ser Trp Ala Asn Trp Leu Cys Ser Tyr Leu Arg Asp Ser Gly
                100                 105                 110

Leu Leu Val Val Leu Leu Ala Thr Phe Val Glu Ala Ala Leu Cys Ala
                115                 120                 125

Trp Tyr Leu Thr Ala Ser Pro Glu Val Val Thr Asp Trp Ser Val Leu
    130                 135                 140

Pro Thr Glu Val Leu Glu His Cys His Val Arg Ser Trp Val Asn Leu
145                 150                 155                 160

Gly Leu Val His Ile Thr Asn Ala Met Val Ala Phe Leu Cys Phe Leu
                165                 170                 175

Gly Thr Phe Leu Val Gln Asp Gln
                180

<210> SEQ ID NO 11
<211> LENGTH: 558
<212> TYPE: DNA
<213> ORGANISM: Rattus sp.

<400> SEQUENCE: 11
gtgctgtcac ttctcctgct gctttgcctg gtgctgggcc tgacactggc tgccctgggg      60
ctctttgtcc actactggga cagccctctt gttcaggcct caggtgggtc actgttctgc     120
tttggcctga tctgcctagg cctcttctgc ctcagtgtcc ttctgttccc aggacgacca     180
cgctctgcca gctgccttgc ccaacaacca atggctcacc tccctctcac aggctgcctg     240
agcacactct tcctgcaagc agccgagatc tttgtggagt ctgagctgcc actgagttgg     300
gcaaactggc tctgcagcta ccttcggggc ccctgggctt ggctggtggt actgctggcc     360
actcttgtgg aggctgcact atgtgcctgg tacttgatgg cttccctcc agaggtggtg      420 acagattggc aggtgctgcc acggaggta ctggaacact gccgcatgcg ttcctgggtc     480
agcctgggct tggtgcacat caccaatgca ggggtagctt cctctgctt tctgggcact     540 ttcctggtac aaagccag                                                  558

<210> SEQ ID NO 12
<211> LENGTH: 186
<212> TYPE: PRT
<213> ORGANISM: Rattus sp.

<400> SEQUENCE: 12

Val Leu Ser Leu Leu Leu Leu Cys Leu Val Leu Gly Leu Thr Leu
1               5                   10                  15

Ala Ala Leu Gly Leu Phe Val His Tyr Trp Asp Ser Pro Leu Val Gln
            20                  25                  30

```
           Ala Ser Gly Gly Ser Leu Phe Cys Phe Gly Leu Ile Cys Leu Gly Leu
                   35                  40                  45

Phe Cys Leu Ser Val Leu Leu Phe Pro Gly Arg Pro Arg Ser Ala Ser
            50                  55                  60

Cys Leu Ala Gln Gln Pro Met Ala His Leu Pro Leu Thr Gly Cys Leu
            65                  70                  75                  80

Ser Thr Leu Phe Leu Gln Ala Ala Glu Ile Phe Val Glu Ser Glu Leu
                           85                  90                  95

Pro Leu Ser Trp Ala Asn Trp Leu Cys Ser Tyr Leu Arg Gly Pro Trp
                       100                 105                 110

Ala Trp Leu Val Val Leu Leu Ala Thr Leu Val Glu Ala Ala Leu Cys
                   115                 120                 125

Ala Trp Tyr Leu Met Ala Phe Pro Pro Glu Val Val Thr Asp Trp Gln
            130                 135                 140

Val Leu Pro Thr Glu Val Leu Glu His Cys Arg Met Arg Ser Trp Val
           145                 150                 155                 160

Ser Leu Gly Leu Val His Ile Thr Asn Ala Gly Val Ala Phe Leu Cys
                           165                 170                 175

Phe Leu Gly Thr Phe Leu Val Gln Ser Gln
                       180                 185

<210> SEQ ID NO 13
<211> LENGTH: 2577
<212> TYPE: DNA
<213> ORGANISM: Rattus sp.

<400> SEQUENCE: 13
atgccgggtt tggctatctt gggcctcagt ctggctgctt tcctggagct tgggatgggg      60 tcctcttgt gtctgtcaca gcaattcaag gcacaagggg actatatatt gggtggacta     120
tttcccctgg cacaactga ggaggccact ctcaaccaga gaacacagcc caacggcatc      180
ctatgtacca ggttctcgcc ccttggtttg ttcctggcca tggctatgaa gatggctgta      240
gaggagatca acaatggatc tgccttgctc cctgggctgc gactgggcta tgacctgttt      300
gacacatgct cagagccagt ggtcaccatg aagcccagcc tcatgttcat ggccaaggtg      360
ggaagtcaaa gcattgctgc ctactgcaac tacacacagt accaaccccg tgtgctggct      420
gtcattggtc cccactcatc agagcttgcc ctcattacag caagttcttc agcttcttc      480 ctcatgccac aggtcagcta tagtgccagc atggatcggc taagtgaccg ggaaacattt      540
ccatccttct tccgcacagt gcccagtgac cgggtcagc tgcaggccgt tgtgacactg      600
ttgcagaatt tcagctggaa ctgggtggct gccttaggta gtgatgatga ctatggccgg      660
gaaggtctga gcatcttttc tggtctggcc aactcacgag gtatctgcat tgcacacgag      720
ggcctggtgc cacaacatga cactagtggc caacaattgg gcaaggtggt ggatgtgcta      780
cgccaagtga accaaagcaa agtacaggtg gtggtgctgt ttgcatctgc ccgtgctgtc      840
tactcccttt ttagctacag catccttcat gacctctcac ccaaggtatg ggtggccagt      900
gagtcctggc tgacctctga cctggtcatg acacttccca atattgcccg tgtgggcact      960
gttcttgggt ttctgcagcg cggtgcccta ctgcctgaat tttccccatta tgtgagact      1020 cgccttgccc tagctgctga cccaacattc tgtgcctccc tgaaagctga gttggatctg      1080
gaggagcgcg tgatgggcc acgctgttca caatgtgact acatcatgct acagaacctg     1140
tcatctgggc tgatgcagaa cctatcagct gggcagttgc accaccaaat atttgcaacc      1200
tatgcagctg tgtacagtgt ggctcaggcc cttcacaaca ccctgcagtg caatgtctca      1260
```

```
cattgccaca catcagagcc tgttcaaccc tggcagctcc tggagaacat gtacaatatg    1320
agtttccgtg ctcgagactt gacactgcag tttgatgcca agggagtgt agacatggaa     1380 tatgacctga agatgtgggt gtggcagagc cctacacctg tactacatac tgtaggcacc    1440
ttcaacggca cccttcagct gcagcactcg aaaatgtatt ggccaggcaa ccaggtgcca    1500
gtctcccagt gctcccggca gtgcaaagat ggccaggtgc gcagagtaaa gggctttcat    1560
tcctgctgct atgactgtgt ggactgcaag cagggagct accggaagca tccagatgac     1620
ttcacctgta ctccatgtgg caaggatcag tggtccccag aaaaaagcac aacctgctta    1680
cctcgcaggc ccaagtttct ggcttggggg gagccagctg tgctgtcact tctcctgctg    1740
ctttgcctgg tgctgggcct gacactggct gccctggggc tctttgtcca ctactgggac    1800
agccctcttg ttcaggcctc aggtgggtca ctgttctgct ttggcctgat ctgcctaggc    1860
ctcttctgcc tcagtgtcct tctgttccca ggacgaccac gctctgccag ctgccttgcc    1920
caacaaccaa tggctcacct ccctctcaca ggctgcctga gcacactctt cctgcaagca    1980
gccgagatct ttgtggagtc tgagctgcca ctgagttggg caaactggct ctgcagctac    2040
cttcggggcc cctgggcttg ctggtggta ctgctgccca ctcttgtgga ggctgcacta     2100
tgtgcctggt acttgatggc tttccctcca gaggtggtga cagattggca ggtgctgccc    2160
acggaggtac tggaacactg ccgcatgcgt tcctgggtca gctgggcttg gtgcacatc     2220 accaatgcag tgttagcttt cctctgcttt ctgggcactt tcctggtaca gagccagcct    2280
ggtcgctata accgtgcccg tggcctcacc ttcgccatgc tagcttattt catcatctgg    2340
gtctcttttg tgcccctcct ggctaatgtg caggtggcct accagccagc tgtgcagatg    2400
ggtgctatct tattctgtgc cctgggcatc ctggccacct tccacctgcc caaatgctat    2460
gtacttctgt ggctgccaga gctcaacacc caggagttct tcctgggaag gagccccaag    2520
gaagcatcag atgggaatag tggtagtagt gaggcaactc ggggacacag tgaatga       2577
```

<210> SEQ ID NO 14
<211> LENGTH: 858
<212> TYPE: PRT
<213> ORGANISM: Rattus sp.

<400> SEQUENCE: 14

```
Met Pro Gly Leu Ala Ile Leu Gly Leu Ser Leu Ala Ala Phe Leu Glu
 1               5                  10                  15

Leu Gly Met Gly Ser Ser Leu Cys Leu Ser Gln Gln Phe Lys Ala Gln
             20                  25                  30

Gly Asp Tyr Ile Leu Gly Gly Leu Phe Pro Leu Gly Thr Thr Glu Glu
         35                  40                  45

Ala Thr Leu Asn Gln Arg Thr Gln Pro Asn Gly Ile Leu Cys Thr Arg
     50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Pro
            100                 105                 110

Ser Leu Met Phe Met Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140
```

```
His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Tyr Gly Arg Glu Gly Leu Ser
210                 215                 220

Ile Phe Ser Gly Leu Ala Asn Ser Arg Gly Ile Cys Ile Ala His Glu
225                 230                 235                 240

Gly Leu Val Pro Gln His Asp Thr Ser Gly Gln Gln Leu Gly Lys Val
                245                 250                 255

Val Asp Val Leu Arg Gln Val Asn Gln Ser Lys Val Gln Val Val Val
                260                 265                 270

Leu Phe Ala Ser Ala Arg Ala Val Tyr Ser Leu Phe Ser Tyr Ser Ile
        275                 280                 285

Leu His Asp Leu Ser Pro Lys Val Trp Val Ala Ser Glu Ser Trp Leu
        290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr Arg Leu Ala Leu Ala Ala Asp Pro Thr Phe Cys Ala
                340                 345                 350

Ser Leu Lys Ala Glu Leu Asp Leu Glu Glu Arg Val Met Gly Pro Arg
        355                 360                 365

Cys Ser Gln Cys Asp Tyr Ile Met Leu Gln Asn Leu Ser Ser Gly Leu
        370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Thr Ser Glu Pro Val Gln Pro Trp Gln
                420                 425                 430

Leu Leu Glu Asn Met Tyr Asn Met Ser Phe Arg Ala Arg Asp Leu Thr
        435                 440                 445

Leu Gln Phe Asp Ala Lys Gly Ser Val Asp Met Glu Tyr Asp Leu Lys
        450                 455                 460

Met Trp Val Trp Gln Ser Pro Thr Pro Val Leu His Thr Val Gly Thr
465                 470                 475                 480

Phe Asn Gly Thr Leu Gln Leu Gln His Ser Lys Met Tyr Trp Pro Gly
                485                 490                 495

Asn Gln Val Pro Val Ser Gln Cys Ser Arg Gln Cys Lys Asp Gly Gln
                500                 505                 510

Val Arg Arg Val Lys Gly Phe His Ser Cys Cys Tyr Asp Cys Val Asp
                515                 520                 525

Cys Lys Ala Gly Ser Tyr Arg Lys His Pro Asp Asp Phe Thr Cys Thr
        530                 535                 540

Pro Cys Gly Lys Asp Gln Trp Ser Pro Glu Lys Ser Thr Thr Cys Leu
545                 550                 555                 560
```

-continued

```
Pro Arg Arg Pro Lys Phe Leu Ala Trp Gly Glu Pro Ala Val Leu Ser
                565                 570                 575
Leu Leu Leu Leu Leu Cys Leu Val Leu Gly Leu Thr Leu Ala Ala Leu
            580                 585                 590
Gly Leu Phe Val His Tyr Trp Asp Ser Pro Leu Val Gln Ala Ser Gly
        595                 600                 605
Gly Ser Leu Phe Cys Phe Gly Leu Ile Cys Leu Gly Leu Phe Cys Leu
    610                 615                 620
Ser Val Leu Leu Phe Pro Gly Arg Pro Arg Ser Ala Ser Cys Leu Ala
625                 630                 635                 640
Gln Gln Pro Met Ala His Leu Pro Leu Thr Gly Cys Leu Ser Thr Leu
                645                 650                 655
Phe Leu Gln Ala Ala Glu Ile Phe Val Glu Ser Glu Leu Pro Leu Ser
            660                 665                 670
Trp Ala Asn Trp Leu Cys Ser Tyr Leu Arg Gly Pro Trp Ala Trp Leu
        675                 680                 685
Val Val Leu Leu Ala Thr Leu Val Glu Ala Ala Leu Cys Ala Trp Tyr
    690                 695                 700
Leu Met Ala Phe Pro Pro Glu Val Val Thr Asp Trp Gln Val Leu Pro
705                 710                 715                 720
Thr Glu Val Leu Glu His Cys Arg Met Arg Ser Trp Val Ser Leu Gly
                725                 730                 735
Leu Val His Ile Thr Asn Ala Val Leu Ala Phe Leu Cys Phe Leu Gly
            740                 745                 750
Thr Phe Leu Val Gln Ser Gln Pro Gly Arg Tyr Asn Arg Ala Arg Gly
        755                 760                 765
Leu Thr Phe Ala Met Leu Ala Tyr Phe Ile Ile Trp Val Ser Phe Val
    770                 775                 780
Pro Leu Leu Ala Asn Val Gln Val Ala Tyr Gln Pro Ala Val Gln Met
785                 790                 795                 800
Gly Ala Ile Leu Phe Cys Ala Leu Gly Ile Leu Ala Thr Phe His Leu
                805                 810                 815
Pro Lys Cys Tyr Val Leu Leu Trp Leu Pro Glu Leu Asn Thr Gln Glu
            820                 825                 830
Phe Phe Leu Gly Arg Ser Pro Lys Glu Ala Ser Asp Gly Asn Ser Gly
        835                 840                 845
Ser Ser Glu Ala Thr Arg Gly His Ser Glu
    850                 855
```

```
<210> SEQ ID NO 15
<211> LENGTH: 8194
<212> TYPE: DNA
<213> ORGANISM: Homo sapiens
<220> FEATURE:
<221> NAME/KEY: modified_base
<222> LOCATION: (1251)..(1300)
<223> OTHER INFORMATION: a, c, t, g, other or unknown
<220> FEATURE:
<221> NAME/KEY: modified_base
<222> LOCATION: (1951)..(2000)
<223> OTHER INFORMATION: a, c, t, g, other or unknown

<400> SEQUENCE: 15
gagaatctcg cgagatcccg tcggtccgcc ccgctgccct cccagctgcc gaaaagaggg    60
gcctccgagc cgccggcgcc ctctgccggc aacctccgga agcacactag gaggttccag   120
ccgatctggt cgaggggctc cacggaggac tccatttacg ttacgcaaat tccctacccc   180
```

```
agccggccgg agagagaaag ccagaaacct cgcgaccagc catgggccac ctctccggaa    240
aaacaccggg atattttttt tctcctgcag aaaaagcttt aggattggca gtttaaacaa    300
aacatgtcta tttgcatacc ttcggtttgc atgcatttgt ttcgaagtga gcaaccctgg    360
gtaacaaggc gaaagtatat gacaatttgc tcagaatctt aatgtcagaa aactggagac    420
tggggcaggg gggtgtcgac tcaaagctgt gtctcattta gtaaactgag gcccaggtaa    480
aaagttctga aacctcgcaa cacccggaga aattgtgttc cagcctccca cctgccccca    540
aaatgccaga gctccttttc taagccaggt gaagtcacag agcgtggaca gaacccacaa    600
ccgtccagag gaagggtcac tgggtgccac ctggtttgca tctgtgcctt cgtcctgccc    660
agttcctgag tgggaccgca ggcccggaat gtcaaggcaa acagtcctgc ttcagccact    720
gggctccagt cccaccccctt ttgggggcct gaagttagga agcatccggc agctgccttc    780
tatttaagca actggcctcc ttagaggcca ctccttggcc atgccaggcg cgggcatctg    840
gccagcatgc tgctctgcac ggctcgcctg gtcggcctgc agcttctcat ttcctgctgc    900
tgggcctttg cctgccatag cacggagtct tctcctgact tcaccctccc cggagattac    960
ctcctggcag gcctgttccc tctccattct ggctgtctgc aggtgaggca cagacccgag   1020
gtgaccctgt gtgacaggtg agtgaggggc cagcagagcc acacttagtg ggaccccctgg   1080 ctatagggcc cctctggctg ccatcctcca aacaggacct tgcctctgcc tttgcccctt   1140
gaactgtccc caggccttgt tcatcaatcc acttgccacc taagtgctgg ctagaccttc   1200
ctagacactt cggccagttt ccaattattt caccccttgct gttagaatgt nnnnnnnnnn   1260
nnnnnnnnnn nnnnnnnnnn nnnnnnnnnn nnnnnnnnnn aattccttaa actaaatttc   1320
tcactttctc tctctctctg gaaaacactg actaatgtag caggtttctc tgctccagga   1380
cttcaggacc ttttcgatgc taataagttt ctccatcagg gccagcttgt tcctcctact   1440
gagcttgaga gcccttgttg aagttgtggt ttgggggact ggaccgatga cctcaaaggt   1500
tccctttgct cccaagcctc agagtctagg aggccagagg gtctcagcag gcctttgtcc   1560
ttctcagctg tctcttactg gctttctcca caggtcttgt agcttcaatg agcatggcta   1620
ccacctcttc caggctatgc ggcttggggt tgaggagata aacaactcca cggccctgct   1680
gcccaacatc accctggggt accagctgta tgatgtgtgt tctgactctg ccaatgtgta   1740
tgccacgctg agagtgctct ccctgccagg gcaacaccac atagagctcc aaggagacct   1800
tctccactat tcccctacgg tgctggcagt gattgggcct gacagcacca accgtgctgc   1860
caccacagcc gccctgctga gcccttttcct ggtgccatg gtaagctgga gcctcagacc   1920
tttgcccatc tcccttcagg caagtctggg nnnnnnnnnn nnnnnnnnnn nnnnnnnnnn   1980
nnnnnnnnnn nnnnnnnnnn gccaccatgc ccggctaatt ttttttgtatt tttagtagag   2040 acggggtttc accgtgttag ccaggctggt cgcaaactcc taacctcgtg atccacccac   2100
ctcggcctcc caatgtgctg ggattacagg tgtgagccac tgcacccggc cataatgtat   2160
taatataata aaataattat acaactcacc ataatgtaga atcagtggga gccctgagct   2220
tgttttccta caactagatg gtcccatctg ggggtgatgg gagacagtga cagatcatca   2280
gacattagat tctcataagt agcgtgcaac ccagatccct cgcatgtgca gttcacagta   2340
gggttcaagc tcctacaaga atctgatgct gctgctgatc tgacaggagg ggagcagctg   2400
taaatacaga tgaagcttcg cttactcacc agctgctcac ctcctcctgt gaggcccggt   2460
tcctaacagg ccactgacct aacttctgcc ctgacctaca catgcttctc ttcttccttg   2520
caaactgcct ccagtggaag tccctgaagg tccccaaaca cacgggacta tttcactcct   2580
```

```
atgcaggttt tgtctccttt gcttggaatg catcccctca cccctttgtcc ccaggcagat   2640 tcccacccct cccccagaac ctgccccagt ggagccttcg caggtgattt gtcagtttca   2700
caggctgagg ggtgctctcc tggtctcccc ggctccctgt atccccacac ccagcacagg   2760
gccaggcact ggggggggcct tcagtggaga ctgaaatggc tgaacgggac ctcccataga   2820
ttagctatgc ggccagcagc gagacgctca gcgtgaagcg gcagtatccc tctttcctgc   2880
gcaccatccc caatgacaag taccaggtgg agaccatggt gctgctgctg cagaagttcg   2940
ggtggacctg gatctctctg gttggcagca gtgacgacta tgggcagcta ggggtgcagg   3000
cactggagaa ccaggccact ggtcagggga tctgcattgc tttcaaggac atcatgccct   3060
tctctgccca ggtgggcgat gagaggatgc agtgcctcat gcgccacctg gcccaggccg   3120
gggccaccgt cgtggttgtt ttttccagcc ggcagttggc cagggtgttt ttcgagtccg   3180
tggtgctgac caacctgact ggcaaggtgt gggtcgcctc agaagcctgg gccctctcca   3240
ggcacatcac tggggtgccc gggatccagc gcattgggat ggtgctgggc gtggccatcc   3300
agaagagggc tgtccctggc ctgaaggcgt ttgaagaagc ctatgcccgg gcagacaaga   3360
aggcccctag gccttgccac aagggctcct ggtgcagcag caatcagctc tgcagagaat   3420
gccaagcttt catggcacac acgatgccca agctcaaagc cttctccatg agttctgcct   3480
acaacgcata ccgggctgtg tatgcggtgg cccatggcct ccaccagctc ctgggctgtg   3540
cctctggagc ttgttccagg ggccgagtct accccctggca ggtaagagag cccacccccag   3600 cacctcctgt cagggagaac agccaatcct gagatgagca gagtgggcac tctccggtca   3660
ctctaaatgc caaggggggat aaatgccact aacttgaggt ttttttgtttt gttttgtttt   3720 gttttttgag acagtctggc tctgtcaccc aggctgcagt gtagtgatgc gatctcggct   3780
ctctgcaact tccacctcct gggttcaagt gattctcttg cctcggcctc ctgagtagct   3840
gggattacag gcacccacca ccatgcctgg ataatttttc ttttctttttt tttttttttg   3900 agatagagtc tcgctctgtt gcccaggctg gaatgcagtg gtgcgatctt ggctcactgt   3960
gagctccgcc tcccaggttc actccattcc cctgcctcag cctcccaagt aggtgggact   4020
acgggcgccc gccaccacgc ccagctaatt ttttttgtat tttgagtaga cacggggttt   4080
caccatgtta gccaggatgg tctcaatctc ctgaccttgt catccgccca cctcgtcctc   4140
ccaaagtgct gggattacag gcgtgagcca ccgcacccgg cctaattttt gtatttttag   4200
tagagatggg gtttcaccat gttggccagg ctggtctcga actcctggca tcaagtgatc   4260
ctcctgcttc ggcctcccaa agtgctggga ttacaggcat tagctctctt ctcttagaca   4320
gatctttctc tctgatcctt gccttctctc acccactgtg tcttggaagt gtcaagtgat   4380
aagatccagg gctaaaactg tctgtaaagg agtgtttgtt agaggcctcc tctcaggagg   4440
ttggtgggga agattgaggg gcttcctaag aaggaaggga cgagaccttc ctgatgggct   4500
gaaaccacca ggacggaaac ccaggaaggc cccaggccct tgcttctggg accatgtggg   4560
tctgtgctgt ctgtggtggc ttcatgatac gcgtttcttt cagcttttgg agcagatcca   4620
caaggtgcat ttccttctac acaaggacac tgtggcgttt aatgacaaca gagatcccct   4680
cagtagctat aacataattg cctgggactg gaatggaccc aagtggacct tcacggtcct   4740
cggttcctcc acatggtctc cagttcagct aaacataaat gagaccaaaa tccagtggca   4800
cggaaaggac aaccaggtaa tggggatgtg gctactcacc atgtaactgg cttatgggca   4860
acctagagcc tgggggtgat gctgacacag tgtacaggga gcaggagggg ggccccaggg   4920
```

```
gtccagctgc caccactcta cccatcctgg ccagggaagc agggaagaca ctccgtaggc    4980
gagtgtgcag atgccctggg gcggaagttc acacgaccag gggccctgcc ctggagtga     5040
gccctgaggg cagatgcaca gagattctgt tttctgttcc acatgtgagc tgtcctttga    5100
cttgggcccc tacgtgtggc ccctctggct tcttacaggt gcctaagtct gtgtgttcca    5160
gcgactgtct tgaagggcac cagcgagtgg ttacgggttt ccatcactgc tgctttgagt    5220
gtgtgccctg tggggctggg accttcctca acaagagtgg tgagtgggca atggagcagg    5280
cgagctaccc agcactcccg ggggctgcac ggtggaggga gggcctccct tgggcccat     5340
gtgccctgcc ccagaaccaa ggcccagtca ctgggctgcc agttagcttc aggttggagg    5400
acacctgcta ccagacagaa ttctgatcaa gagaatcagc cactgggtgc ggtggctcat    5460
gcctgtaatc ccagcacttt ggaggctga ggcgggtgga tcacttgagg tcggagttc      5520
gagaccagcc tggccaacat ggtgaaaccc catctctacc aaaaatataa aaaattagct    5580
gggtgtggtg cgcgtgcct gtaatcccag ctactcggga ggctgaggca ggagaatcac     5640
ttgaacccag gaggcggagg ttgcagtgag ccaagatgca ttccagcctg gaccacaaag    5700
cgagaattcg tcccccccaaa aaaagaaagg aggccgggcg cggtggctca cacctgtaat   5760
cccagcactt tgggaggccg aggtgggtgg atcacctgag gtcaggagtt cgagaccagc    5820
ctgaccaaca tggtgaaacc ccatctctac taaaaataca aaaaagtta gccgggcgtt     5880
gtggcgtgtg cctgtaattc cagctactcg ggaggctgag gcaggagaat tgcttgaacc    5940
cgggaggcgg aggttgcagt gagccaagat tgcaccattg cactccagcc tgggcgacaa    6000
gagaaaaact ctgtctcaaa aaaaagaaa gaaagaaaga attagccaac tgaaagcctt     6060
agactgaggt gtgtcctctg ttagagagct gtcatcacaa ctcctacaaa agcagtcgta    6120
tcctgaattc aacctctttc tctaaatgaa tatagctatt gttccctttg tgccctcttg    6180
tcctactgtc ccttctgttg cccatgccaa agacagctag ctccttgaac agcttggcct    6240
gaatacagat actagcgtgt ctgcagcaga gaaaaaaaca gcattcccca tccagaaatg    6300
caaggtcaag aacagagagc aaattaggta gctaaggact caggtcctta gttggtgtcc    6360
aggggccaca ttctttcctt tcaccatctc tgtagggaca ggaatacttc ccttctgtcc    6420
tcagagggtc aggactcaga gaaaccacag agcagcagct caggaaagtg gttcatggaa    6480
atgctggcaa gagagagggg ttacaatgcc ctcccttggg agcaggctgc tcccatcaga    6540
tcgtaacctc tctggtatgt gggcagagct accaggttaa ggtcctccct agggtttgca    6600
aaaccctcat gggatcatga gccatacaga accgacctgt gtgtctccag agtctgtaat    6660
taacacaggc attttgagga aatgcgtggc ctcaggcccc actcccggct accccatcc    6720
cactatgcct agtatagtct agctgccctg gtacaattct cccagtatct tgcaggcccc    6780
tatttcctat tcctactctg ctcatctggc tctcaggaac cttcttggcc ttcccttca    6840
gacctctaca gatgccagcc ttgtgggaaa gaagagtggg cacctgaggg aagccagacc    6900
tgcttcccgc gcactgtggt gttttttggct ttgcgtgagc acacctcttg ggtgctgctg   6960
gcagctaaca cgctgctgct gctgctgctg cttgggactg ctggcctgtt tgcctggcac    7020
ctagacaccc ctgtggtgag gtcagcaggg ggccgcctgt gctttcttat gctgggctcc    7080
ctggcagcag gtagtggcag cctctatggc ttctttgggg aacccacaag gcctgcgtgc    7140
ttgctacgcc aggccctctt tgcccttggt ttcaccatct tcctgtcctg cctgacagtt    7200
cgctcattcc aactaatcat catcttcaag ttttccacca aggtacctac attctaccac    7260
gcctgggtcc aaaaccacgg tgctggcctg tttgtgatga tcagctcagc ggcccagctg    7320
```

```
cttatctgtc taacttggct ggtggtgtgg acccactgc ctgctaggga ataccagcgc    7380
ttcccccatc tggtgatgct tgagtgcaca gagaccaact ccctgggctt catactggcc    7440
ttcctctaca atggcctcct ctccatcagt gcctttgcct gcagctacct gggtaaggac    7500
ttgccagaga actacaacga ggccaaatgt gtcaccttca gcctgctctt caacttcgtg    7560
tcctggatcg ccttcttcac cacggccagc gtctacgacg gcaagtacct gcctgcggcc    7620
aacatgatgg ctgggctgag cagcctgagc agcggcttcg gtgggtattt tctgcctaag    7680
tgctacgtga tcctctgccg cccagacctc aacagcacag agcacttcca ggcctccatt    7740
caggactaca cgaggcgctg cggctccacc tgaccagtgg gtcagcaggc acggctggca    7800
gccttctctg ccctgagggt cgaaggtcga gcaggccggg ggtgtccggg aggtctttgg    7860
gcatcgcggt ctgggttgg acgtgtaag cgcctgggag agcctagacc aggctccggg    7920
ctgccaataa agaagtgaaa tgcgtatctg gtctcctgtc gtgggagagt gtgaggtgta    7980
acggattcaa gtctgaaccc agagcctgga aaaggctgac cgcccagatt gacgttgcta    8040
ggcaactccg gaggcgggcc cagcgccaaa agaacagggc gaggcgtcgt ccccgcatcc    8100
cattggccgt tctctgcggg gccccgcct cggggccgg agctagaagc tctacgcttc    8160
cgaggcgcac ctcctggcct gcacgctttg acgt                                8194

<210> SEQ ID NO 16
<211> LENGTH: 2526
<212> TYPE: DNA
<213> ORGANISM: Homo sapiens

<400> SEQUENCE: 16
atgctgctct gcacggctcg cctggtcggc ctgcagcttc tcatttcctg ctgctgggcc      60
tttgcctgcc atagcacgga gtcttctcct gacttcaccc tccccggaga ttacctcctg     120
gcaggcctgt tccctctcca ttctggctgt ctgcaggtga ggcacagacc cgaggtgacc     180
ctgtgtgaca ggtcttgtag cttcaatgag catggctacc acctcttcca ggctatgcgg     240
cttggggttg aggagataaa caactccacg gccctgctgc caacatcac cctgggtac     300
cagctgtatg atgtgtgttc tgactctgcc aatgtgtatg ccacgctgag agtgctctcc     360
ctgccagggc aacaccacat agagctccaa ggagaccttc tccactattc ccctacggtg     420
ctggcagtga ttgggcctga cagcaccaac cgtgctgcca ccacagccgc cctgctgagc     480
cctttcctgg tgcccatgat tagctatgcg ccagcagcg agacgctcag cgtgaagcgg     540
cagtatccct ctttcctgcg caccatcccc aatgacaagt accaggtgga ccatggtg      600
ctgctgctgc agaagttcgg gtggacctgg atctctctgg ttggcagcag tgacgactat     660
gggcagctag gggtgcaggc actggagaac caggccactg tcagggat ctgcattgct     720
ttcaaggaca tcatgccctt ctctgcccag gtgggcgatg agaggatgca gtgcctcatg     780
cgccacctgg cccaggccgg ggccaccgtc gtggttgttt tttccagccg gcagttggcc     840
agggtgtttt tcgagtccgt ggtgctgacc aacctgactg gcaaggtgtg ggtcgcctca     900
gaagcctggg ccctctccag gcacatcact ggggtgcccg ggatccagcg cattgggatg     960
gtgctgggcg tggccatcca gaagagggct gtccctggcc tgaaggcgtt tgaagaagcc    1020
tatgcccggg cagacaagaa ggcccctagg ccttgccaca gggctcctg gtgcagcagc    1080
aatcagctct gcagagaatg ccaagctttc atggcacaca cgatgcccaa gctcaaagcc    1140
ttctccatga gttctgccta caacgcatac cgggctgtgt atgcggtggc ccatggcctc    1200
```

```
caccagctcc tgggctgtgc ctctggagct tgttccaggg gccgagtcta cccctggcag    1260
cttttggagc agatccacaa ggtgcatttc cttctacaca aggacactgt ggcgtttaat    1320
gacaacagag atcccctcag tagctataac ataattgcct gggactggaa tggacccaag    1380
tggaccttca cggtcctcgg ttcctccaca tggtctccag ttcagctaaa cataaatgag    1440
accaaaatcc agtggcacgg aaaggacaac caggtgccta agtctgtgtg ttccagcgac    1500
tgtcttgaag ggcaccagcg agtggttacg ggtttccatc actgctgctt tgagtgtgtg    1560
ccctgtgggg ctgggacctt cctcaacaag agtgacctct acagatgcca gccttgtggg    1620
aaagaagagt gggcacctga gggaagccag acctgcttcc cgcgcactgt ggtgtttttg    1680
gctttgcgtg agcacacctc ttgggtgctg ctggcagcta acacgctgct gctgctgctg    1740
ctgcttggga ctgctggcct gtttgcctgg cacctagaca cccctgtggt gaggtcagca    1800
gggggccgcc tgtgctttct tatgctgggc tccctggcag caggtagtgg cagcctctat    1860
ggcttctttg gggaacccac aaggcctgcg tgcttgctac gccaggccct ctttgccctt    1920
ggtttcacca tcttcctgtc ctgcctgaca gttcgctcat ccaactaat catcatcttc    1980 aagtttttcca ccaaggtacc tacattctac cacgcctggg tccaaaacca cggtgctggc    2040
ctgtttgtga tgatcagctc agcggcccag ctgcttatct gtctaacttg ctggtggtg    2100 tggaccccac tgcctgctag ggaataccag cgcttccccc atctggtgat gcttgagtgc    2160
acagagacca actccctggg cttcatactg gccttcctct acaatggcct cctctccatc    2220
agtgcctttg cctgcagcta cctgggtaag gacttgccag agaactacaa cgaggccaaa    2280
tgtgtcacct tcagcctgct cttcaacttc gtgtcctgga tcgccttctt caccacggcc    2340
agcgtctacg acggcaagta cctgcctgcg gccaacatga tggctgggct gagcagcctg    2400
agcagcggct tcggtgggta ttttctgcct aagtgctacg tgatcctctg ccgcccagac    2460
ctcaacagca cagagcactt ccaggcctcc attcaggact acacgaggcg ctgcggctcc    2520
acctga                                                               2526
```

<210> SEQ ID NO 17
<211> LENGTH: 841
<212> TYPE: PRT
<213> ORGANISM: Homo sapiens

<400> SEQUENCE: 17

```
Met Leu Leu Cys Thr Ala Arg Leu Val Gly Leu Gln Leu Leu Ile Ser
 1               5                  10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
```

```
                     130                 135                 140
Gly Pro Asp Ser Thr Asn Arg Ala Ala Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Gln Lys Phe Gly Trp
        195                 200                 205

Thr Trp Ile Ser Leu Val Gly Ser Ser Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
                260                 265                 270

Val Phe Ser Ser Arg Gln Leu Ala Arg Val Phe Phe Glu Ser Val Val
            275                 280                 285

Leu Thr Asn Leu Thr Gly Lys Val Trp Val Ala Ser Glu Ala Trp Ala
            290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
                340                 345                 350

His Lys Gly Ser Trp Cys Ser Ser Asn Gln Leu Cys Arg Glu Cys Gln
            355                 360                 365

Ala Phe Met Ala His Thr Met Pro Lys Leu Lys Ala Phe Ser Met Ser
            370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
                420                 425                 430

His Lys Asp Thr Val Ala Phe Asn Asp Asn Arg Asp Pro Leu Ser Ser
            435                 440                 445

Tyr Asn Ile Ile Ala Trp Asp Trp Asn Gly Pro Lys Trp Thr Phe Thr
            450                 455                 460

Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
            515                 520                 525

Asn Lys Ser Asp Leu Tyr Arg Cys Gln Pro Cys Gly Lys Glu Glu Trp
        530                 535                 540

Ala Pro Glu Gly Ser Gln Thr Cys Phe Pro Arg Thr Val Val Phe Leu
545                 550                 555                 560
```

```
Ala Leu Arg Glu His Thr Ser Trp Val Leu Ala Ala Asn Thr Leu
            565                 570                 575

Leu Leu Leu Leu Leu Leu Gly Thr Ala Gly Leu Phe Ala Trp His Leu
            580                 585                 590

Asp Thr Pro Val Val Arg Ser Ala Gly Gly Arg Leu Cys Phe Leu Met
            595                 600                 605

Leu Gly Ser Leu Ala Ala Gly Ser Gly Ser Leu Tyr Gly Phe Phe Gly
            610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
            645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
            675                 680                 685

Ala Gln Leu Leu Ile Cys Leu Thr Trp Leu Val Val Trp Thr Pro Leu
            690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
            725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
            755                 760                 765

Asn Phe Val Ser Trp Ile Ala Phe Phe Thr Thr Ala Ser Val Tyr Asp
            770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
            805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
            835                 840

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)
<223> OTHER INFORMATION: Thr or Arg
<220> FEATURE:
<221> NAME/KEY: MOD_RES
<222> LOCATION: (3)
<223> OTHER INFORMATION: Phe or Leu
<220> FEATURE:
<221> NAME/KEY: MOD_RES
<222> LOCATION: (4)
<223> OTHER INFORMATION: Arg, Gln or Pro
<220> FEATURE:
<221> NAME/KEY: MOD_RES
<222> LOCATION: (6)
<223> OTHER INFORMATION: Arg or Thr
```

```
<220> FEATURE:
<221> NAME/KEY: MOD_RES
<222> LOCATION: (7)
<223> OTHER INFORMATION: Ser, Pro or Val
<220> FEATURE:
<221> NAME/KEY: MOD_RES
<222> LOCATION: (8)
<223> OTHER INFORMATION: Val, Glu, Arg, Lys or Thr
<220> FEATURE:
<221> NAME/KEY: MOD_RES
<222> LOCATION: (11)
<223> OTHER INFORMATION: Ala or Glu
<220> FEATURE:
<221> NAME/KEY: MOD_RES
<222> LOCATION: (12)
<223> OTHER INFORMATION: Trp or Leu
<220> FEATURE:
<221> NAME/KEY: MOD_RES
<222> LOCATION: (13)
<223> OTHER INFORMATION: Arg, His or Gly

<400> SEQUENCE: 18

Xaa Cys Xaa Xaa Arg Xaa Xaa Xaa Phe Leu Xaa Xaa Xaa Glu
 1               5                  10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)
<223> OTHER INFORMATION: Leu or Gln
<220> FEATURE:
<221> NAME/KEY: MOD_RES
<222> LOCATION: (3)
<223> OTHER INFORMATION: Glu, Gly or Thr
<220> FEATURE:
<221> NAME/KEY: MOD_RES
<222> LOCATION: (4)
<223> OTHER INFORMATION: Asn, Arg or Cys
<220> FEATURE:
<221> NAME/KEY: MOD_RES
<222> LOCATION: (7)
<223> OTHER INFORMATION: Arg or Glu
<220> FEATURE:
<221> NAME/KEY: MOD_RES
<222> LOCATION: (9)
<223> OTHER INFORMATION: Arg or Lys
<220> FEATURE:
<221> NAME/KEY: MOD_RES
<222> LOCATION: (10)
<223> OTHER INFORMATION: Cys, Gly or Phe
<220> FEATURE:
<221> NAME/KEY: MOD_RES
<222> LOCATION: (11)
<223> OTHER INFORMATION: Val, Leu or Ile
<220> FEATURE:
<221> NAME/KEY: MOD_RES
<222> LOCATION: (13)
<223> OTHER INFORMATION: Phe or Leu
<220> FEATURE:
<221> NAME/KEY: MOD_RES
<222> LOCATION: (14)
<223> OTHER INFORMATION: Ala or Asn
<220> FEATURE:
<221> NAME/KEY: MOD_RES
<222> LOCATION: (15)
<223> OTHER INFORMATION: Met or Leu

<400> SEQUENCE: 19

Xaa Pro Xaa Xaa Tyr Asn Xaa Ala Xaa Xaa Xaa Thr Xaa Xaa Xaa
 1               5                  10                  15
```

<210> SEQ ID NO 20
<211> LENGTH: 3563
<212> TYPE: DNA
<213> ORGANISM: Homo sapiens

<400> SEQUENCE: 20

| | | | | | |
|---|---|---|---|---|---|
| agcctggcag | tggcctcagg | cagagtctga | cgcgcacaaa | ctttcaggcc | caggaagcga | 60 |
| ggacaccact | ggggcccag | ggtgtggcaa | gtgaggatgg | caagggtttt | gctaaacaaa | 120 |
| tcctctgccc | gctccccgcc | ccgggctcac | tccatgtgag | gccccagtcg | gggcagccac | 180 |
| ctgccgtgcc | tgttggaagt | tgcctctgcc | atgctgggcc | ctgctgtcct | gggcctcagc | 240 |
| ctctgggctc | tcctgcaccc | tgggacgggg | gccccattgt | gcctgtcaca | gcaacttagg | 300 |
| atgaagggg | actacgtgct | gggggggctg | ttcccctgg | gcgaggccga | ggaggctggc | 360 |
| ctccgcagcc | ggacacggcc | cagcagccct | gtgtgcacca | ggtacagagg | tgggacggcc | 420 |
| tgggtcgggg | tcagggtgac | caggtctggg | gtgctcctga | gctggggccg | aggtggccat | 480 |
| ctgcggttct | gtgtggcccc | aggttctcct | caaacggcct | gctctgggca | ctggccatga | 540 |
| aaatggccgt | ggaggagatc | aacaacaagt | cggatctgct | gcccgggctg | cgcctgggct | 600 |
| acgacctctt | tgatacgtgc | tcggagcctg | tggtggccat | gaagcccagc | ctcatgttcc | 660 |
| tgccaaggc | aggcagccgc | gacatcgccg | cctactgcaa | ctacacgcag | taccagcccc | 720 |
| gtgtgctggc | tgtcatcggg | ccccactcgt | cagagctcgc | catggtcacc | ggcaagttct | 780 |
| tcagcttctt | cctcatgccc | cagtggggcg | ccccccacca | tcaccacccc | caaccaacc | 840 |
| cctgccccgt | gggagcccct | tgtgtcagga | gaatgctaca | tgcaccccac | ccagccctgc | 900 |
| cctgggagcc | ctgtgtcaga | agatgctctt | ggccttgcag | gtcagctacg | gtgctagcat | 960 |
| ggagctgctg | agcgcccggg | agaccttccc | ctccttcttc | cgcaccgtgc | cagcgaccg | 1020 |
| tgtgcagctg | acggccgccg | cggagctgct | gcaggagttc | ggctggaact | gggtggccgc | 1080 |
| cctgggcagc | gacgacgagt | acggccggca | gggcctgagc | atcttctcgg | ccctggccgc | 1140 |
| ggcacgcggc | atctgcatcg | cgcacgaggg | cctggtgccg | ctgccccgtg | ccgatgactc | 1200 |
| gcggctgggg | aaggtgcagg | acgtcctgca | ccaggtgaac | cagagcagcg | tgcaggtggt | 1260 |
| gctgctgttc | gcctccgtgc | acgccgccca | cgccctcttc | aactacagca | tcagcagcag | 1320 |
| gctctcgccc | aaggtgtggg | tggccagcga | ggcctggctg | acctctgacc | tggtcatggg | 1380 |
| gctgcccggc | atgcccagda | tgggcacggt | gcttggcttc | ctccagaggg | gtgcccagct | 1440 |
| gcacgagttc | ccccagtacg | tgaagacgca | cctggcctg | gccaccgacc | cggccttctg | 1500 |
| ctctgccctg | ggcgagaggg | agcagggtct | ggaggaggac | gtggtgggcc | agcgctgccc | 1560 |
| gcagtgtgac | tgcatcacgc | tgcagaacgt | gagcgcaggg | ctaaatcacc | accagacgtt | 1620 |
| ctctgtctac | gcagctgtgt | atagcgtggc | ccaggccctg | cacaacactc | ttcagtgcaa | 1680 |
| cgcctcaggc | tgccccgcgc | aggacccgt | gaagccctgg | caggtgagcc | cgggagatgg | 1740 |
| gggtgtgctg | tcctctgcat | gtgcccaggc | caccaggcac | ggccaccacg | cctgagctgg | 1800 |
| aggtggctgg | cggctcagcc | ccgtccccg | cccgcagctc | ctggagaaca | tgtacaacct | 1860 |
| gaccttccac | gtgggcgggc | tgcctctgcg | gttcgacagc | agcggaaacg | tggacatgga | 1920 |
| gtacgacctg | aagctgtggg | tgtggcaggg | ctcagtgccc | aggctccacg | acgtgggcag | 1980 |
| gttcaacggc | agcctcagga | cagagcgcct | gaagatccgc | tggcacacgt | ctgacaacca | 2040 |
| ggtgaggtga | gggtgggtgt | gccaggcgtg | cccgtggtag | ccccccgcggc | agggcgcagc | 2100 |

```
ctggggggtgg gggccgttcc agtctcccgt gggcatgccc agccgagcag agccagaccc    2160
caggcctgtg cgcagaagcc cgtgtcccgg tgctcgcggc agtgccagga gggccaggtg    2220
cgccgggtca aggggttcca ctcctgctgc tacgactgtg tggactgcga ggcgggcagc    2280
taccggcaaa acccaggtga gccgccttcc cggcaggcgg gggtgggaac gcagcagggg    2340
agggtcctgc caagtcctga ctctgagacc agagcccaca gggtacaaga cgaacaccca    2400
gcgcccttct cctctctcac agacgacatc gcctgcacct tttgtggcca ggatgagtgg    2460
tccccggagc gaagcacacg ctgcttccgc cgcaggtctc ggttcctggc atggggcgag    2520
ccggctgtgc tgctgctgct cctgctgctg agcctggcgc tgggccttgt gctggctgct    2580
ttggggctgt tcgttcacca tcgggacagc ccactggttc aggcctcggg ggggcccctg    2640
gcctgctttg gctggtgtg cctgggcctg gtctgcctca gcgtcctcct gttccctggc    2700
cagcccagcc ctgcccgatg cctggcccag cagcccttgt cccacctccc gctcacgggc    2760
tgcctgagca cactcttcct gcaggcggcc gagatcttcg tggagtcaga actgcctctg    2820
agctgggcag accggctgag tggctgcctg cgggggccct gggcctggct ggtggtgctg    2880
ctggccatgc tggtggaggt cgcactgtgc acctggtacc tggtggcctt cccgccggag    2940
gtggtgacgg actggcacat gctgcccacg gaggcgctgg tgcactgccg cacacgctcc    3000
tgggtcagct tcggcctagc gcacgccacc aatgccacgc tggcctttct ctgcttcctg    3060
ggcactttcc tggtgcggag ccagccgggc tgctacaacc gtgcccgtgg cctcaccttt    3120
gccatgctgg cctacttcat cacctgggtc tcctttgtgc ccctcctggc caatgtgcag    3180
gtggtcctca ggcccgccgt gcagatgggc gccctcctgc tctgtgtcct gggcatcctg    3240
gctgccttcc acctgcccag gtgttacctg ctcatgcggc agccagggct caacacccc    3300 gagttcttcc tgggaggggg ccctggggat gcccaaggcc agaatgacgg gaacacagga    3360
aatcagggga aacatgagtg acccaaccct gtgatctcag ccccggtgaa cccagactta    3420
gctgcgatcc cccccaagcc agcaatgacc cgtgtctcgc tacagagacc ctcccgctct    3480
aggttctgac cccaggttgt ctcctgaccc tgaccccaca gtgagcccta ggcctggagc    3540
acgtggacac ccctgtgacc atc                                           3563
```

T1R TASTE RECEPTORS AND GENES ENCODING SAME

RELATED APPLICATIONS

This application us a divisional of U.S. application Ser. No. 14/696,896 filed Apr. 27, 2015, which is a divisional of U.S. application Ser. No. 13/600,377 filed Aug. 31, 2012, now U.S. Pat. No. 9,040,247, which is a continuation of U.S. application Ser. No. 13/092,598, filed Apr. 22, 2011, now U.S. Pat. No. 8,263,341, which is a divisional of U.S. application Ser. No. 12/392,143, filed Feb. 25, 2009, now U.S. Pat. No. 8,815,525, which is a continuation of U.S. application Ser. No. 10/725,081, filed Dec. 2, 2003, now U.S. Pat. No. 7,507,544, which is a divisional of U.S. application Ser. No. 09/799,629, filed Mar. 7, 2001, now U.S. Pat. No. 7,244,835, which application claims the benefit of the following provisional applications: U.S. Ser. No. 60/187,546, filed Mar. 7, 2000, entitled "NOVEL TASTE RECEPTOR AND GENE ENCODING SAME", to Zozulya and Adler; U.S. Ser. No. 60/195,536, filed Apr. 7, 2000, entitled "MAMMALIAN TASTE RECEPTOR AND HUMAN ORTHOLOG", to Adler; U.S. 60/209,840, filed Jun. 6, 2000, entitled "NOVEL TASTE RECEPTOR AND GENE ENCODING SAME", to Zozulya and Adler, U.S. Ser. No. 60/214,213, filed Jun. 23, 2000, entitled "NOVEL TASTE RECEPTOR AND GENE ENCODING SAME", to Zozulya and Adler; U.S. Ser. No. 60/226,448, filed Aug. 17, 2000, entitled "NOVEL TASTE RECEPTOR AND GENE ENCODING SAME", to Zozulya and Adler, and U.S. Ser. No. 60/259,227, filed Jan. 3, 2001, entitled "T1R TASTE RECEPTORS AND GENES ENCODING SAME", to Adler, Li, Staszewski (now Luukkonen) and O'Connell, all of which are hereby incorporated by reference in their entireties.

BACKGROUND OF THE INVENTION

Sequence Listing

This application includes as part of its disclosure a biological sequence listing text file named "43268o4308.txt" having a size of 59,622 bytes that was created Apr. 10, 2017, which is hereby incorporated by reference in its entirety.

Field of the Invention

The invention relates to newly identified mammalian chemosensory G protein-coupled receptors, to family of such receptors, and to the genes and cDNA encoding said receptors. More particularly, the invention relates to newly identified mammalian chemosensory G protein-coupled receptors active in taste signaling, to a family of such receptors, to the genes and cDNA encoding said receptors, and to methods of using such receptors, genes, and cDNA in the analysis and discovery of taste modulators.

Description of the Related Art

The taste system provides sensory information about the chemical composition of the external world. Taste transduction is one of the most sophisticated forms of chemical-triggered sensation in animals. At present, the means by which taste sensations are elicited remains poorly understood. See, e.g., Margolskee, *BioEssays*, 15:645-50 (1993); Avenet et al., *J. Membrane Biol.*, 112:1-8 (1989). Taste signaling is found throughout the animal kingdom, from simple metazoans to the most complex of vertebrates. Taste sensation is thought to involve distinct signaling pathways. These pathways are believed to be mediated by receptors, i.e., metabotropic or inotropic receptors. Cells which express taste receptors, when exposed to certain chemical stimuli, elicit taste sensation by depolarizing to generate an action potential, which is believed to trigger the sensation. This event is believed to trigger the release of neurotransmitters at gustatory afferent neuron synapses, thereby initiating signaling along neuronal pathways that mediate taste perception. See, e.g., Roper, *Ann. Rev. Neurosci.*, 12:329-53 (1989).

As such, taste receptors specifically recognize molecules that elicit specific taste sensation. These molecules are also referred to herein as "tastants." Many taste receptors belong to the 7-transmembrane receptor superfamily (Hoon et al., *Cell* 96:451 (1999); Adler et al., *Cell* 100:693 (2000)), which are also known as G protein-coupled receptors (GPCRs). Other tastes are believed to be mediated by channel proteins. G protein-coupled receptors control many physiological functions, such as endocrine function, exocrine function, heart rate, lipolysis, carbohydrate metabolism, and transmembrane signaling. The biochemical analysis and molecular cloning of a number of such receptors has revealed many basic principles regarding the function of these receptors.

For example, U.S. Pat. No. 5,691,188 describes how upon a ligand binding to a GPCR, the receptor presumably undergoes a conformational change leading to activation of the G protein. G proteins are comprised of three subunits: a guanyl nucleotide binding $\alpha$ subunit, a $\beta$ subunit, and a $\gamma$ subunit. G proteins cycle between two forms, depending on whether GDP or GTP is bound to the $\alpha$ subunit. When GDP is bound, the G protein exists as a heterotrimer: the G$\alpha\beta\gamma$ complex. When GTP is bound, the $\alpha$ subunit dissociates from the heterotrimer, leaving a G$\beta\gamma$ complex. When a G$\alpha\beta\gamma$ complex operatively associates with an activated G protein-coupled receptor in a cell membrane, the rate of exchange of GTP for bound GDP is increased and the rate of dissociation of the bound G$\alpha$ subunit from the G$\alpha\mu\gamma$ complex increases. The free G$\alpha$ subunit and G$\beta\gamma$ complex are thus capable of transmitting a signal to downstream elements of a variety of signal transduction pathways. These events form the basis for a multiplicity of different cell signaling phenomena, including for example the signaling phenomena that are identified as neurological sensory perceptions such as taste and/or smell.

Mammals are believed to have five basic taste modalities: sweet, bitter, sour, salty, and umami (the taste of monosodium glutamate). See, e.g., Kawamura et al., *Introduction to Umami: A Basic Taste* (1987); Kinnamon et al., *Ann. Rev. Physiol.*, 54:715-31 (1992); Lindemann, *Physiol. Rev.*, 76:718-66 (1996); Stewart et al., *Am J. Physiol.*, 272:1-26 (1997). Numerous physiological studies in animals have shown that taste receptor cells may selectively respond to different chemical stimuli. See, e.g., Akabas et al., *Science*, 242:1047-50 (1988); Gilbertson et al., *J. Gen. Physiol.*, 100:803-24 (1992); Bernhardt et al., *J. Physiol.*, 490:325-36 (1996); Cummings et al., *J. Neurophysiol.*, 75:1256-63 (1996).

In mammals, taste receptor cells are assembled into taste buds that are distributed into different papillae in the tongue epithelium. Circumvallate papillae, found at the very back of the tongue, contain hundreds to thousands of taste buds. By contrast, foliate papillae, localized to the posterior lateral edge of the tongue, contain dozens to hundreds of taste buds. Further, fungiform papillae, located at the front of the tongue, contain only a single or a few taste buds.

Each taste bud, depending on the species, contains 50-150 cells, including precursor cells, support cells, and taste receptor cells. See, e.g., Lindemann, *Physiol. Rev.,* 76:718-66 (1996). Receptor cells are innervated at their base by afferent nerve endings that transmit information to the taste centers of the cortex through synapses in the brain stem and thalamus. Elucidating the mechanisms of taste cell signaling and information processing is important to understanding the function, regulation, and perception of the sense of taste.

Although much is known about the psychophysics and physiology of taste cell function, very little is known about the molecules and pathways that mediate its sensory signaling response. The identification and isolation of novel taste receptors and taste signaling molecules could allow for new methods of chemical and genetic modulation of taste transduction pathways. For example, the availability of receptor and channel molecules could permit the screening for high affinity agonists, antagonists, inverse agonists, and modulators of taste activity. Such taste modulating compounds could be useful in the pharmaceutical and food industries to improve the taste of a variety of consumer products, or to block undesirable tastes, e.g., in certain pharmaceuticals.

Complete or partial sequences of numerous human and other eukaryotic chemosensory receptors are currently known. See e.g., Pilpel, Y. and Lancet, D., *Protein Science,* 8:969-977 (1999); Mombaerts, P., *Annu. Rev. Neurosci.,* 22:487-50 (1999). See also, EP0867508A2. U.S. Pat. No. 5,874,243, WO 92/17585, WO 95/18140, WO 97/17444, WO 99/67282. Because of the complexity of ligand-receptor interactions, and more particularly tastant-receptor interactions, information about ligand-receptor recognition is lacking. In part, the present invention addresses the need for better understanding of the interactions between chemosensory receptors and chemical stimuli. The present invention also provides, among other things, novel chemosensory receptors, and methods for utilizing such receptors, and the genes a cDNAs encoding such receptors, to identify molecules that can be used to modulate chemosensory transduction, such as taste sensation.

SUMMARY OF THE INVENTION

The invention relates to a new family of G protein-coupled receptors, and to the genes and cDNAs encoding said receptors. The receptors are thought to be primarily involved in sweet taste transduction, but can be involved in transducing signals from other taste modalities as well.

The invention provides methods for representing the perception of taste and/or for predicting the perception of taste in a mammal, including in a human. Preferably, such methods may be performed by using the receptors and genes encoding said receptors disclosed herein.

Toward that end, it is an object of the invention to provide a new family of mammalian G protein-coupled receptors, herein referred to as T1Rs, active in taste perception. It is another object of the invention to provide fragments and variants of such T1Rs that retain tastant-binding activity.

It is yet another object of the invention to provide nucleic acid sequences or molecules that encode such T1Rs, fragments, or variants thereof.

It is still another object of the invention to provide expression vectors which include nucleic acid sequences that encode such T1Rs, or fragments or variants thereof, which are operably linked to at least one regulatory sequence such as a promoter, enhancer, or other sequence involved in positive or negative gene transcription and/or translation.

It is still another object of the invention to provide human or non-human cells that functionally express at least one of such T1Rs, or fragments or variants thereof.

It is still another object of the invention to provide T1R fusion proteins or polypeptides which include at least a fragment of at least one of such T1Rs.

It is another object of the invention to provide an isolated nucleic acid molecule encoding a T1R polypeptide comprising a nucleic acid sequence that is at least 50%, preferably 75%, 85%, 90%, 95%, 96%, 97%, 98%, or 99% identical to a nucleic acid sequence selected from the group consisting of: SEQ ID NOS: 1, 2, 3, 9, 11, 13, 15, 16, 20, and conservatively modified variants thereof.

It is a further object of the invention to provide an isolated nucleic acid molecule comprising a nucleic acid sequence that encodes a polypeptide having an amino acid sequence at least 35 to 50%, and preferably 60%, 75%, 85%, 90%, 95%, 96%, 97%, 98%, or 99% identical to an amino acid sequence selected from the group consisting of: SEQ ID NOS: 4, 10, 12, 14, 17, and conservatively modified variants thereof, wherein the fragment is at least 20, preferably 40, 60, 80, 100, 150, 200, or 250 amino acids in length. Optionally, the fragment can be an antigenic fragment which binds to an anti-T1R antibody.

It is still a further object of the invention to provide an isolated polypeptide comprising a variant of said fragment, wherein there is a variation in at most 10, preferably 5, 4, 3, 2, or 1 amino acid residues.

It is still another object of the invention to provide agonists or antagonists of such T1Rs, or fragments or variants thereof.

It is yet another object of the invention to provide methods for representing the perception of taste and/or for predicting the perception of taste in a mammal, including in a human. Preferably, such methods may be performed by using the T1Rs, or fragments or variants thereof, and genes encoding such T1Rs, or fragments or variants thereof, disclosed herein.

It is yet another object of the invention to provide novel molecules or combinations of molecules which elicit a predetermined taste perception in a mammal. Such molecules or compositions can be generated by determining a value of taste perception in a mammal for a known molecule or combinations of molecules; determining a value of taste perception in a mammal for one or more unknown molecules or combinations of molecules; comparing the value of taste perception in a mammal for one or more unknown compositions to the value of taste perception in a mammal for one or more known compositions; selecting a molecule or combination of molecules that elicits a predetermined taste perception in a mammal; and combining two or more unknown molecules or combinations of molecules to form a molecule or combination of molecules that elicits a predetermined taste perception in a mammal. The combining step yields a single molecule or a combination of molecules that elicits a predetermined taste perception in a mammal.

It is still a further object of the invention to provide a method of screening one or more compounds for the presence of a taste detectable by a mammal, comprising: a step of contacting said one or more compounds with at least one of the disclosed T1Rs, fragments or variants thereof, preferably wherein the mammal is a human.

It is another object of the invention to provided a method for simulating a taste, comprising the steps of: for each of a plurality of T1Rs, or fragments of variants thereof disclosed herein, preferably human T1Rs, ascertaining the extent to which the T1R interacts with the tastant; and combining a plurality of compounds, each having a previously ascertained interaction with one or more of the T1Rs, in amounts that together provide a receptor-stimulation profile that mimics the profile for the taste. Interaction of a tastant with a T1R can be determined using any of the binding or reporter assays described herein. The plurality of compounds may then be combined to form a mixture. If desired, one or more of the plurality of the compounds can be combined covalently. The combined compounds substantially stimulate at least 50%, 60%, 70%, 75%, 80% or 90% or all of the receptors that are substantially stimulated by the tastant.

In yet another aspect of the invention, a method is provided wherein a plurality of standard compounds are tested against a plurality of T1Rs, or fragments or variants thereof, to ascertain the extent to which the T1Rs each interact with each standard compound, thereby generating a receptor stimulation profile for each standard compound. These receptor stimulation profiles may then be stored in a relational database on a data storage medium. The method may further comprise providing a desired receptor-stimulation profile for a taste; comparing the desired receptor stimulation profile to the relational database; and ascertaining one or more combinations of standard compounds that most closely match the desired receptor-stimulation profile. The method may further comprise combining standard compounds in one or more of the ascertained combinations to simulate the taste.

It is a further object of the invention to provide a method for representing taste perception of a particular tastant in a mammal, comprising the steps of: providing values $X_1$ to $X_n$ representative of the quantitative stimulation of each of n T1Rs of said vertebrate, where n is greater than or equal to 2; and generating from said values a quantitative representation of taste perception. The T1Rs may be an taste receptor disclosed herein, or fragments or variants thereof, the representation may constitutes a point or a volume in n-dimensional space, may constitutes a graph or a spectrum, and may constitutes a matrix of quantitative representations. Also, the providing step may comprise contacting a plurality of recombinantly-produced T1Rs, or fragments or variants thereof, with a test composition and quantitatively measuring the interaction of said composition with said receptors.

It is yet another object of the invention to provide a method for predicting the taste perception in a mammal generated by one or more molecules or combinations of molecules yielding unknown taste perception in a mammal, comprising the steps of: providing values $X_1$ to $X_n$ representative of the quantitative stimulation of each of n T1Rs of said vertebrate, where n is greater than or equal to 2; for one or more molecules or combinations of molecules yielding known taste perception in a mammal; and generating from said values a quantitative representation of taste perception in a mammal for the one or more molecules or combinations of molecules yielding known taste perception in a mammal, providing values $X_1$ to $X_n$ representative of the quantitative stimulation of each of n T1Rs of said vertebrate, where n is greater than or equal to 2; for one or more molecules or combinations of molecules yielding unknown taste perception in a mammal; and generating from said values a quantitative representation of taste perception in a mammal for the one or more molecules or combinations of molecules yielding unknown taste perception in a mammal, and predicting the taste perception in a mammal generated by one or more molecules or combinations of molecules yielding unknown taste perception in a mammal by comparing the quantitative representation of taste perception in a mammal for the one or more molecules or combinations of molecules yielding unknown taste perception in a mammal to the quantitative representation of taste perception in a mammal for the one or more molecules or combinations of molecules yielding known taste perception in a mammal. The T1Rs used in this method may include a taste receptor, or fragment or variant thereof, disclosed herein.

BRIEF DESCRIPTION OF THE DRAWINGS

The FIGURE contains a cryosection of frozen mouse tongue showing T1R3 gene expression in taste buds of mouse circumvallate papillae by in situ hybridization. Select T1R3-expressing taste receptor cells are marked with arrows.

DETAILED DESCRIPTION OF THE INVENTION

The invention thus provides isolated nucleic acid molecules encoding taste-cell-specific G protein-coupled receptors ("GPCR"), and the polypeptides they encode. These nucleic acid molecules and the polypeptides that they encode are members of the T1R family of taste-cell-specific GPCRs. Members of the T1R family of taste-cell-specific GPCRs are identified in Hoon et al., *Cell*, 96:541-551 (1999), WO 00/06592, and WO 00/06593, all of which are incorporated herein by reference in their entireties.

More particularly, the invention provides nucleic acids encoding a novel family of taste-cell-specific GPCRs. These nucleic acids and the receptors that they encode are referred to as members of the "T1R" family of taste-cell-specific GPCRs. In particular embodiments of the invention, the T1R family members include rT1R3, mT1R3, hT1R3, and hT1R1. While not wishing to be bound by theory, it is believed that these taste-cell-specific GPCRs are components of the taste transduction pathway, and may be involved in the taste detection of sweet substances and/or other taste modalities.

Further, it is believed that T1R family members may act in combination with other T1R family members, other taste-cell-specific GPCRs, or a combination thereof, to thereby effect chemosensory taste transduction. For instance, it is believed that T1R1 and T1R3 maybe coexpressed within the same taste receptor cell type, and the two receptors may physically interact to form a heterodimeric taste receptor. Alternatively, T1R1 and T1R3 may both independently bind to the same type of ligand, and their combined binding may result in a specific perceived taste sensation.

These nucleic acids provide valuable probes for the identification of taste cells, as the nucleic acids are specifically expressed in taste cells. For example, probes for T1R polypeptides and proteins can be used to identify taste cells present in foliate, circumvallate, and fungiform papillae, as well as taste cells present in the geschmackstreifen, oral cavity, gastrointestinal epithelium, and epiglottis. They may also serve as tools for the generation of taste topographic maps that elucidate the relationship between the taste cells of the tongue and taste sensory neurons leading to taste centers in the brain. In particular, methods of detecting T1Rs can be used to identify taste cells sensitive to sweet tastants or other specific modalities of tastants. Furthermore, the nucleic acids and the proteins they encode can be used as probes to dissect taste-induced behaviors. Also, chromosome localization of the genes encoding human T1Rs can be used to identify diseases, mutations, and traits caused by and associated with T1R family members.

The nucleic acids encoding the T1R proteins and polypeptides of the invention can be isolated from a variety of sources, genetically engineered, amplified, synthesized, and/or expressed recombinantly according to the methods disclosed in WO 00/035374, which is herein incorporated by reference in its entirety.

The invention also provides methods of screening for modulators, e.g., activators, inhibitors, stimulators, enhancers, agonists, and antagonists, of these novel taste-cell-specific GPCRs. Such modulators of taste transduction are useful for pharmacological, chemical, and genetic modulation of taste signaling pathways. These methods of screening can be used to identify high affinity agonists and antagonists of taste cell activity. These modulatory compounds can then be used in the food and pharmaceutical industries to customize taste, e.g., to modulate the sweet tastes of foods or drugs.

Thus, the invention provides assays for detecting and characterizing taste modulation, wherein T1R family members act as direct or indirect reporter molecules of the effect of modulators on taste transduction. GPCRs can be used in assays to, e.g., measure changes in ligand binding, ion concentration, membrane potential, current flow, ion flux, transcription, signal transduction, receptor-ligand interactions, second messenger concentrations, in vitro, in vivo, and er vivo. In one embodiment, members of the T1R family can be used as indirect reporters via attachment to a second reporter molecule such as green fluorescent protein (see, e.g., Mistili & Spector, *Nature Biotechnology*, 15:961-964 (1997)). In another embodiment, T1R family members may be recombinantly expressed in cells, and modulation of taste transduction via GPCR activity may be assayed by measuring changes in $Ca^{2+}$ levels and other intracellular messages such as cAMP, cGMP, or IP3.

In certain embodiments, a domain of a T1R polypeptide, e.g., an extracellular, transmembrane, or intracellular domain, is fused to a heterologous polypeptide, thereby forming a chimeric polypeptide, e.g., a chimeric polypeptide with GPCR activity. Such chimeric polypeptides are useful, e.g., in assays to identify ligands, agonists, antagonists, or other modulators of a T1R polypeptide. In addition, such chimeric polypeptides are useful to create novel taste receptors with novel ligand binding specificity, modes of regulation, signal transduction pathways, or other such properties, or to create novel taste receptors with novel combinations of ligand binding specificity, modes of regulation, signal transduction pathways, etc.

In one embodiment, a T1R polypeptide is expressed in a eukaryotic cell as a chimeric receptor with a heterologous, chaperone sequence that facilitates plasma membrane trafficking, or maturation and targeting through the secretory pathway. The optional heterologous sequence may be a rhodopsin sequence, such as an N-terminal fragment of a rhodopsin. Such chimeric T1R receptors can be expressed in any eukaryotic cell, such as human kidney two hundred ninety three cells. Preferably, the cells comprise a G protein, e.g., Gα15 or Gα16 or another type of promiscuous G protein capable of pairing a wide range of chemosensory GPCRs to an intracellular signaling pathway or to a signaling protein such as phospholipase C. Activation of such chimeric receptors in such cells can be detected using any standard method, such as by detecting changes in intracellular calcium by detecting FURA-2 dependent fluorescence in the cell. If preferred host cells do not express an appropriate G protein, they may be transfected with a gene encoding a promiscuous G protein such as those described in U.S. Application Ser. No. 60/243,770, which is herein incorporated by reference in its entirety.

Methods of assaying for modulators of taste transduction include in vitro ligand-binding assays using: T1R polypeptides, portions thereof, i.e., the extracellular domain, transmembrane region, or combinations thereof, or chimeric proteins comprising one or more domains of a T1R family member; oocyte or tissue culture cells expressing T1R polypeptides, fragments, or fusion proteins; phosphorylation and dephosphorylation of T1R family members; G protein binding to GPCRs; ligand-binding assays; voltage, membrane potential and conductance changes; ion flux assays; changes in intracellular second messengers such as cGMP, cAMP and inositol triphosphate; changes in intracellular calcium levels; and neurotransmitter release.

Further, the invention provides methods of detecting T1R nucleic acid and protein expression, allowing investigation of taste transduction regulation and specific identification of taste receptor cells. T1R family members also provide useful nucleic acid probes for paternity and forensic investigations. T1R genes are also useful as a nucleic acid probes for identifying taste receptor cells, such as foliate, fungiform, circumvallate, geschmackstreifen, and epiglottis taste receptor cells. T1R receptors can also be used to generate monoclonal and polyclonal antibodies useful for identifying taste receptor cells. Taste receptor cells can be identified using techniques such as reverse transcription and amplification of mRNA, isolation of total RNA or poly A+ RNA, northern blotting, dot blotting, in situ hybridization, RNase protection, S1 digestion, probing DNA microchip arrays, western blots, and the like.

Functionally, the T1R polypeptides comprise a family of related seven transmembrane G protein-coupled receptors, which are believed to be involved in taste transduction and may interact with a G protein to mediate taste signal transduction (see, e.g., Fong, *Cell Signal*, 8:217 (1996); Baldwin, *Curr. Opin. Cell Biol.*, 6:180 (1994)). Structurally, the nucleotide sequences of T1R family members may encode related polypeptides comprising an extracellular domain, seven transmembrane domains, and a cytoplasmic domain. Related T1R family genes from other species share at least about 50%, and optionally 60%, 70%, 80%, or 90%, nucleotide sequence identity over a region of at least about 50 nucleotides in length, optionally 100, 200, 500, or more nucleotides in length to SEQ ID NOS: 1, 2, 3, 9, 11, 13, 15, 16, 20, or conservatively modified variants thereof, or encode polypeptides sharing at least about 35 to 50%, and optionally 60%, 70%, 80%, or 90%, amino acid sequence identity over an amino acid region at least about 25 amino acids in length, optionally 50 to 100 amino acids in length to SEQ ID NOS: 4, 10, 12, 14, 17, or conservatively modified variants thereof.

Several consensus amino acid sequences or domains have also been identified that are characteristic of T1R family members. For example, T1R family members typically comprise a sequence having at least about 50%, optionally 55%, 60%, 65%, 70%, 75%, 80%, 85%, 90%, 95-99%, or higher, identity to T1R consensus sequences 1 and 2 (SEQ ID NOs 18 and 19, respectively). These conserved domains thus can be used to identify members of the T1R family, by identity, specific hybridization or amplification, or specific binding by antibodies raised against a domain. Such T1R consensus sequences have the following amino acid sequences:

T1R Family Consensus Sequence 1:
(SEQ ID NO: 18)
(TR)C(FL)(RQP)R(RT)(SPV)(VERKT)FL(AE)(WL)(RHG)E T1R Family Consensus Sequence 2:
(SEQ ID NO: 19)
(LQ)P(EGT)(NRC)YN(RE)A(RK)(CGF)(VLI)T(FL)(AS)(ML)

These consensus sequences are inclusive of those found in the T1R polypeptides described herein, but T1R family members from other organisms may be expected to comprise consensus sequences having about 75% identity or more to the inclusive consensus sequences described specifically herein.

Specific regions of the T1R nucleotide and amino acid sequences may be used to identify polymorphic variants, interspecies homologs, and alleles of T1R family members. This identification can be made in vitro, e.g., under stringent hybridization conditions or PCR (e.g., using primers encoding the T1R consensus sequences identified above), or by using the sequence information in a computer system for comparison with other nucleotide sequences. Different alleles of T1R genes within a single species population will also be useful in determining whether differences in allelic sequences correlate to differences in taste perception between members of the population. Classical PCR-type amplification and cloning techniques are useful for isolating orthologs, for example, where degenerate primers are sufficient for detecting related genes across species, which typically have a higher level of relative identity than paralogous members of the T1R family within a single species.

For instance, degenerate primers SAP077 (SEQ. ID NO. 5) and SAP0079 (SEQ. ID NO. 6) can be used can be used to amplify and clone T1R3 genes from different mammalian genomes. In contrast, genes within a single species that are related to T1R3 are best identified using sequence pattern recognition software to look for related sequences. Typically, identification of polymorphic variants and alleles of T1R family members can be made by comparing an amino acid sequence of about 25 amino acids or more, e.g., 50-100 amino acids. Amino acid identity of approximately at least 35 to 50%, and optionally 60%, 70%, 75%, 80%, 85%, 90%, 95-99%, or above typically demonstrates that a protein is a polymorphic variant, interspecies homolog, or allele of a T1R family member. Sequence comparison can be performed using any of the sequence comparison algorithms discussed below. Antibodies that bind specifically to T1R polypeptides or a conserved region thereof can also be used to identify alleles, interspecies homologs, and polymorphic variants.

Polymorphic variants, interspecies homologs, and alleles of T1R genes can be confirmed by examining taste-cell-specific expression of the putative T1R polypeptide. Typically, T1R polypeptides having an amino acid sequence disclosed herein can be used as a positive control in comparison to the putative T1R polypeptide to demonstrate the identification of a polymorphic variant or allele of the T1R family member. The polymorphic variants, alleles, and interspecies homologs are expected to retain the seven transmembrane structure of a G protein-coupled receptor. For further detail, see WO 00/06592, which discloses related T1R family members, GPCR-B3s, the contents of which are herein incorporated by reference in a manner consistent with this disclosure. GPCR-B3 receptors are referred to herein as rT1R1 and mT1R1. Additionally, see WO 00/06593, which also discloses related T1R family members, GPCR-B4s, the contents of which are herein incorporated by reference in a manner consistent with this disclosure. GPCR-B4 receptors are referred to herein as rT1R2 and mT1R2.

Nucleotide and amino acid sequence information for T1R family members may also be used to construct models of taste-cell-specific polypeptides in a computer system. These models can be subsequently used to identify compounds that can activate or inhibit T1R receptor proteins. Such compounds that modulate the activity of T1R family members can then be used to investigate the role of T1R genes and receptors in taste transduction.

The present invention also provides assays, preferably high throughput assays, to identify molecules that interact with and/or modulate a T1R polypeptide. In numerous assays, a particular domain of a T1R family member is used, e.g., an extracellular, transmembrane, or intracellular domain or region. In numerous embodiments, an extracellular domain, transmembrane region or combination thereof may be bound to a solid substrate, and used, e.g., to isolate ligands, agonists, antagonists, or any other molecules that can bind to and/or modulate the activity of a T1R polypeptide.

In one aspect of the invention, a new human GPCR gene of the T1R family, termed hT1R3, is provided. The hT1R3 gene was identified from the human genome sequence database including the HTGS division of GenBank. The nucleotide and conceptually translated amino acid sequence for hT1R3 are provided in SEQ. ID NOS 1-4. The hT1R3 receptor was identified in the partially sequenced BAC genomic clone RP5-890O3 (database accession number AL139287) by virtue of its sequence similarity to the candidate rat taste receptor rT1R1 (accession number AF127389). By reference, the pairwise identity between the predicted hT1R3 and rT1R1 protein sequences is approximately 34%. Sequence comparisons with additional members of the GPCR Family C (which includes the calcium-sensing receptors, putative V2R pheromone receptors, GABA-B receptors, fish taste receptors, and metabotropic glutamate receptors) indicate that hT1R3 is likely to belong to the Family C subgroup defined by T1R1 and a second rat candidate taste receptor (rT1R2, accession number AF127390).

The invention also provides the human ortholog, termed hT1R1, of a rat taste receptor, designated rT1R1. The gene products of rT1R1 and hT1R1 are approximately 74% identical. The mouse gene, mT1R1 has been reported, see Hoon et al., Cell, 96:541-551 (2000), and maps to a chromosomal interval homologous to the interval containing hT1R1. The nucleotide and conceptually-translated hT1R1 sequences are described herein as SEQ. ID NOS 15 and 16, respectively.

While not wishing to be bound to any particular theory, the T1R family of receptors is predicted to be involved in sweet taste transduction by virtue of the linkage of mT1R3 to the Sac locus, a locus on the distal end of chromosome four that influences sweet taste. Human T1R3 has also been reported to localize to 1p36.2-1p36.33, a region that displays conserved synteny with the mouse interval containing Sac and T1R1. However, T1R type receptors may mediate other taste modalities, such as bitter, umami, sour and salty.

Various conservative mutations and substitutions are envisioned to be within the scope of the invention. For instance, it would be within the level of skill in the art to perform amino acid substitutions using known protocols of recombinant gene technology including PCR, gene cloning, site-directed mutagenesis of cDNA, transfection of host cells, and in-vitro transcription. The variants could then be screened for taste-cell-specific GPCR functional activity.

A. Identification and Characterization of T1R Polypeptides

The amino acid sequences of the T1R proteins and polypeptides of the invention can be identified by putative translation of the coding nucleic acid sequences. These various amino acid sequences and the coding nucleic acid sequences may be compared to one another or to other sequences according to a number of methods.

For example, in sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, as described below for the BLASTN and BLASTP programs, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Natl. Acad Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J Mol. Biol.* 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Altschul et al., *Nuc. Acids Res.* 25:3389-3402 (1977) and Altschul et al., *J Mol. Biol.* 215:403-410 (1990)). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad Sci. USA* 89:10915 (1989)) alignments (B) of 50, expectation (E) of 10, M=5, N=−4, and a comparison of both strands.

Another example of a useful algorithm is PILEUP. PILEUP creates a multiple sequence alignment from a group of related sequences using progressive, pairwise alignments to show relationship and percent sequence identity. It also plots a so-called "tree" or "dendogram" showing the clustering relationships used to create the alignment see. PILEUP uses a simplification of the progressive alignment method of Feng & Doolittle, *J Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984) encoded by the genes were derived by conceptual translation of the corresponding open reading frames. Comparison of these protein sequences to all known proteins in the public sequence databases using BLASTP algorithm revealed their strong homology to the members of the T1R family, each of the T1R family sequences having at least about 35 to 50%, and preferably at least 55%, at least 60%, at least 65%, and most preferably at least 70%, amino acid identity to at least one known member of the family.

B. Definitions

As used herein, the following terms have the meanings ascribed to them unless specified otherwise.

"Taste cells" include neuroepithelial cells that are organized into groups to form taste buds of the tongue, e.g., foliate, fungiform, and circumvallate cells (see, e.g., Roper et al., *Ann. Rev. Neurosci.* 12:329-353 (1989)). Taste cells are also found in the palate and other tissues, such as the esophagus and the stomach.

"T1R" refers to one or more members of a family of G protein-coupled receptors that are expressed in taste cells such as foliate, fungiform, and circumvallate cells, as well as cells of the palate, and esophagus (see, e.g., Hoon et al., *Cell*, 96:541-551 (1999), herein incorporated by reference in its entirety). Members of this family are also referred to as GPCR-B3 and TR1 in WO 00/06592 as well as GPCR-B4 and TR2 in WO 00/06593. GPCR-B3 is also herein referred to as rT1R1, and GPCR-B4 is referred to as rT1R2. Taste receptor cells can also be identified on the basis of morphology (see, e.g., Roper, supra), or by the expression of proteins specifically expressed in taste cells. T1R family members may have the ability to act as receptors for sweet taste transduction, or to distinguish between various other taste modalities.

"T1R" nucleic acids encode a family of GPCRs with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase (for a description of the structure and function of GPCRs, see, e.g., Fong, supra, and Baldwin, supra). A single taste cell may contain many distinct T1R polypeptides.

The term "T1R" family therefore refers to polymorphic variants, alleles, mutants, and interspecies homologs that: (1) have at least about 35 to 50% amino acid sequence identity, optionally about 60, 75, 80, 85, 90, 95, 96, 97, 98, or 99% amino acid sequence identity to SEQ ID NOS: 4, 10, 12, 14, or 17, over a window of about 25 amino acids, optionally 50-100 amino acids; (2) specifically bind to antibodies raised against an immunogen comprising an amino acid sequence selected from the group consisting of SEQ ID NOS: 4, 10, 12, 14, 17, and conservatively modified variants thereof; (3) are encoded by a nucleic acid molecule which specifically hybridize (with a size of at least about 100, optionally at least about 500-1000 nucleotides) under stringent hybridization conditions to a sequence selected from the group consisting of SEQ ID NOS: 1, 2, 3, 9, 11, 13, 15, 16, 20, and conservatively modified variants thereof; (4) comprise a sequence at least about 35 to 50% identical to an amino acid sequence selected from the group consisting of SEQ ID NOS: 4, 10, 12, 14, or 17; or (5) are amplified by primers that specifically hybridize under stringent hybridization conditions to the same sequence as degenerate primer sets encoding SEQ ID NOS: 7, 8, and conservatively modified variants thereof.

Topologically, certain chemosensory GPCRs have an "N-terminal domain;" "extracellular domains;" "transmembrane domains" comprising seven transmembrane regions, and corresponding cytoplasmic, and extracellular loops; "cytoplasmic domains," and a "C-terminal domain" (see, e.g., Hoon et al., *Cell*, 96:541-551 (1999); Buck & Axel, *Cell*, 65:175-187 (1991)). These domains can be structurally identified using methods known to those of skill in the art, such as sequence analysis programs that identify hydrophobic and hydrophilic domains (see, e.g., Stryer, *Biochemistry*, (3rd ed. 1988); see also any of a number of Internet based sequence analysis programs, such as those found at dot.imgen.bcm.tmc.edu). Such domains are useful for making chimeric proteins and for in vitro assays of the invention, e.g., ligand-binding assays.

"Extracellular domains" therefore refers to the domains of T1R polypeptides that protrude from the cellular membrane and are exposed to the extracellular face of the cell. Such domains generally include the "N terminal domain" that is exposed to the extracellular face of the cell, and optionally can include portions of the extracellular loops of the transmembrane domain that are exposed to the extracellular face of the cell, i.e., the loops between transmembrane regions 2 and 3, between transmembrane regions 4 and 5, and between transmembrane regions 6 and 7.

The "N terminal domain" region starts at the N-terminus and extends to a region close to the start of the transmembrane domain. More particularly, in one embodiment of the invention, this domain starts at the N-terminus and ends approximately at the conserved glutamic acid at amino acid position 563 plus or minus approximately 20 amino acid. The region corresponding to amino acids 1-580 of SEQ ID 40 is a particular embodiment of an extracellular domain that extends slightly into the transmembrane domain. These extracellular domains are useful for in vitro ligand-binding assays, both soluble and solid phase. In addition, transmembrane regions, described below, can also bind ligand either in combination with the extracellular domain, and are therefore also useful for in vitro ligand-binding assays.

"Transmembrane domain," which comprises the seven "transmembrane regions," refers to the domain of T1R polypeptides that lies within the plasma membrane, and may also include the corresponding cytoplasmic (intracellular) and extracellular loops. In one embodiment, this region corresponds to the domain of T1R family members which starts approximately at the conserved glutamic acid residue at amino acid position 563 plus or minus 20 amino acids and ends approximately at the conserved tyrosine amino acid residue at position 812 plus or minus approximately 10 amino acids. The seven transmembrane regions and extracellular and cytoplasmic loops can be identified using standard methods, as described in Kyte & Doolittle, *J. Mol. Biol.*, 157:105-32 (1982)), or in Stryer, supra.

"Cytoplasmic domains" refers to the domains of T1R polypeptides that face the inside of the cell, e.g., the "C terminal domain" and the intracellular loops of the transmembrane domain, e.g., the intracellular loop between transmembrane regions 1 and 2, the intracellular loop between transmembrane regions 3 and 4, and the intracellular loop between transmembrane regions 5 and 6. "C terminal domain" refers to the region that spans the end of the last transmembrane domain and the C-terminus of the protein, and which is normally located within the cytoplasm. In one embodiment, this region starts at the conserved tyrosine amino acid residue at position 812 plus or minus approximately 10 amino acids and continues to the C-terminus of the polypeptide.

The term "ligand-binding region" or "ligand-binding domain" refers to sequences derived from a chemosensory receptor, particularly a taste receptor, that substantially incorporates at least the extracellular domain of the receptor. In one embodiment, the extracellular domain of the ligand-binding region may include the N-terminal domain and, optionally, portions of the transmembrane domain, such as the extracellular loops of the transmembrane domain. The ligand-binding region may be capable of binding a ligand, and more particularly, a tastant.

The phrase "functional effects" in the context of assays for testing compounds that modulate T1R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" in the context of assays is meant assays for a compound that increases or decreases a parameter that is indirectly or directly under the influence of a T1R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T1R gene expression; tissue culture cell T1R expression; transcriptional activation of T1R genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T1R genes or proteins are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G proteins; kinases (e.g., homologs of rhodopsin kinase and beta adrenergic receptor kinases that are involved in deactivation and desensitization of a receptor); and arrestins, which also deactivate and desensitize receptors. Modulators can include genetically modified versions of T1R family members, e.g., with altered activity, as well as naturally occurring and synthetic ligands, antagonists, agonists, small chemical molecules and the like. Such assays for inhibitors and activators include, e.g., expressing T1R family members in cells or cell membranes, applying putative modulator compounds, in the presence or absence of tastants, e.g., sweet tastants, and then determining the functional effects on taste transduction, as described above. Samples or assays comprising T1R family members that are treated with a potential activator, inhibitor, or modulator are compared to control samples without the inhibitor, activator, or modulator to examine the extent of modulation. Control samples (untreated with modulators) are assigned a relative T1R activity value of 100%. Inhibition of a T1R is achieved when the T1R activity value relative to the control is about 80%, optionally 50% or 25-0%. Activation of a T1R is achieved when the T1R activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated" "isolated," when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific degenerate oligonucleotide primer pairs) for amplifying (e.g., by polymerase chain reaction, PCR) naturally expressed (e.g., genomic or mRNA) or recombinant (e.g., cDNA) nucleic acids of the invention (e.g., tastant-binding sequences of the invention) in vivo or in vitro.

The term "7-transmembrane receptor" means a polypeptide belonging to a superfamily of transmembrane proteins that have seven domains that span the plasma membrane seven times (thus, the seven domains are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "library" means a preparation that is a mixture of different nucleic acid or polypeptide molecules, such as the library of recombinantly generated chemosensory, particularly taste receptor ligand-binding domains generated by amplification of nucleic acid with degenerate primer pairs, or an isolated collection of vectors that incorporate the amplified ligand-binding domains, or a mixture of cells each randomly transfected with at least one vector encoding an taste receptor.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones (see e.g., *Oligonucleotides and Analogues, a Practical Approach*, ed. F. Eckstein, Oxford Univ. Press (1991);

Antisense Strategies, *Annals of the N.Y. Academy of Sciences*, Vol. 600, Eds. Baserga et al. (NYAS 1992); Milligan *J. Med. Chem.* 36:1923-1937 (1993); *Antisense Research and Applications* (1993, CRC Press), WO 97/03211; WO 96/39154; Mata, *Toxicol. Appl. Pharmacol.* 144:189-197 (1997); Strauss-Soukup, *Biochemistry* 36:8692-8698 (1997); Samstag, *Antisense Nucleic Acid Drug Dev,* 6:153-156 (1996)).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., *Nucleic Acid Res.,* 19:5081 (1991); Ohtsuka et al., *J. Biol. Chem.,* 260:2605-2608 (1985); Rossolini et al., *Mol. Cell. Probes,* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "plasma membrane translocation domain" or simply "translocation domain" means a polypeptide domain that, when incorporated into the amino terminus of a polypeptide coding sequence, can with great efficiency "chaperone" or "translocate" the hybrid ("fusion") protein to the cell plasma membrane. For instance, a "translocation domain" may be derived from the amino terminus of the bovine rhodopsin receptor polypeptide, a 7-transmembrane receptor. However, rhodopsin from any mammal may be used, as can other translocation facilitating sequences. Thus, the translocation domain is particularly efficient in translocating 7-transmembrane fusion proteins to the plasma membrane, and a protein (e.g., a taste receptor polypeptide) comprising an amino terminal translocating domain will be transported to the plasma membrane more efficiently than without the domain. However, if the N-terminal domain of the polypeptide is active in binding, the use of other translocation domains may be preferred.

The "translocation domain," "ligand-binding domain", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser, arg/lys; asn/gln or his; asp/glu; cys/ser, gln/asn; gly/asp; gly/ala or pro; his/asn or gin; ile/leu or val; leu/ile or val; lys/arg or gin or glu; met/leu or tyr or ile; phe/met or leu or tyr, ser/thr, thr/ser, trp/tyr, tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, *Proteins*, W.H. Freeman and Company (1984); Schultz and Schimer, *Principles of Protein Structure*, Springer-Vrlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding domains, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$), thiazole, retroamide, thioamide, or ester (see, e.g., Spatola, *Chemistry and Biochemistry of Amino Acids, Peptides and Proteins*, Vol. 7, pp 267-357, "Peptide Backbone Modifications," Marcell Dekker, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental- or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridisation with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, S×SSC, and 1% SDS, incubating at 42° C., or, S×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCI, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof; is altered, replaced or exchanged with a variable region having a different or altered antigen specificity.

An "anti-T1R" antibody is an antibody or antibody fragment that specifically binds a polypeptide encoded by a T1R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a T1R family member from specific species such as rat, mouse, or human can be selected to obtain only those polyclonal antibodies that are specifically immunoreactive with the T1R polypeptide or an immunogenic portion thereof and not with other proteins, except for orthologs or polymorphic variants and alleles of the T1R polypeptide. This selection may be achieved by subtracting out antibodies that cross-react with T1R molecules from other species or other T1R molecules. Antibodies can also be selected that recognize only T1R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual*, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as E. toll, or eukaryotic cells such as yeast, insect, amphibian, or mammalian cells such as CHO, HeLa, human kidney two hundred ninety three, and the like, e.g., cultured cells, explants, and cells in vivo.

C. Isolation and Expression of T1R Polypeptides

Isolation and expression of the T1Rs, or fragments or variants thereof, of the invention can be performed as described below. PCR primers can be used for the amplification of nucleic acids encoding taste receptor ligand-binding regions, and libraries of these nucleic acids can optionally be generated. Individual expression vectors or libraries of expression vectors can then be used to infect or transfect host cells for the functional expression of these nucleic acids or libraries. These genes and vectors can be made and expressed in vitro or in vivo. One of skill will recognize that desired phenotypes for altering and controlling nucleic acid expression cam be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect, or plant systems.

Alternatively, these nucleic acids can be synthesized in vitro by well-known chemical synthesis techniques, as described in, e.g., Carruthers, *Cold Spring Harbor Symp. Quant. Biol.* 47:411-418 (1982); Adams, *Am. Chem. Soc.* 105:661 (1983); Belousov, *Nucleic Acids Res.* 25:3440-3444 (1997); Frenkel, *Free Radic. Biol. Med.* 19:373-380 (1995); Blommers, *Biochemistry* 33:7886-7896 (1994); Narang, *Meth. Enzymol.* 68:90 (1979); Brown, *Meth. Enzymol.* 68:109 (1979); Beaucage, *Tetra. Lett.* 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: a Laboratory manual (2nd ed.), Vols. 1-3, Cold Spring Harbor Laboratory (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I, Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassays (RIAs), enzyme-linked immunosorbant assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acid fragments encoding taste receptor ligand-binding regions. The nucleic acids described herein can also be cloned or measured quantitatively using amplification techniques. Amplification methods are also well known in the art, and include, e.g., polymerase chain reaction, PCR (*PCR Protocols, a Guide to Methods and Applications*, ed. Innis. Academic Press, N.Y. (1990) and *PCR Strategies*, ed. Innis, Academic Press, Inc., N.Y. (1995), ligase chain reaction (LCR) (see, e.g., Wu, *Genomics* 4:560 (1989); Landegren, *Science* 241:1077, (1988); Barringer, *Gene* 89:117 (1990)); transcription amplification (see, e.g., Kwoh, *Proc. Natl. Acad. Sci. USA* 86:1173 (1989)); and, self-sustained sequence replication (see. e.g., Guatelli, *Proc. Natl. Acad. Sci. USA* 87:1 S74 (1990)); Q Beta replicase amplification (see. e.g., Smith, *J. Clin. Microbiol.* 35:1477-1491 (1997)); automated Q-beta replicase amplification assay (see, e.g., Burg, *Mol. Cell. Probes* 10:257-271 (1996)) and other RNA polymerase mediated techniques (e.g., NASBA, Cangene, Mississauga, Ontario); see also Berger, *Methods Enzymol.* 152:307-316 (1987); Sambrook; Ausubel; U.S. Pat. Nos. 4,683,195 and 4,683,202; Sooknanan, *Biotechnology* 13:563-564 (1995). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like). Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039.

The primer pairs may be designed to selectively amplify ligand-binding regions of the T1R family members. These regions may vary for different ligands or tastants. Thus, what may be a minimal binding region for one tastant, may be too limiting for a second tastant. Accordingly, ligand-binding regions of different sizes comprising different extracellular domain structures may be amplified.

Paradigms to design degenerate primer pairs are well known in the art. For example, a COnsensus-DEgenerate Hybrid Oligonucleotide Primer (CODEHOP) strategy computer program is accessible and is directly linked from the BlockMaker multiple sequence alignment site for hybrid primer prediction beginning with a set of related protein sequences, as known taste receptor ligand-binding regions (see, e.g., Rose, Nucleic Acids Res. 26:1628-1635 (1998); Singh, Biotechniques 24:318-319 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, *Nucleic Acids Res.* 25:4866-4871 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, *Nat. Struct. Biol.* 5:950-954 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, *Proc. Natl. Acad. Sci. USA* 95:4258-4263 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T1R polypeptides and polymorphic variants, alleles, and interspecies homologs thereof, by detecting expressed homologs immunologically with antisera or purified antibodies made against a T1R polypeptide, which also recognize and selectively bind to the T1R homolog.

Nucleic acids that encode ligand-binding regions of taste receptors may be generated by amplification (e.g., PCR) of appropriate nucleic acid sequences using degenerate primer pairs. The amplified nucleic acid can be genomic DNA from any cell or tissue or mRNA or cDNA derived from taste receptor-expressing cells.

In one embodiment, hybrid protein-coding sequences comprising nucleic acids encoding T1Rs fused to a translocation sequences may be constructed. Also provided are hybrid T1Rs comprising the translocation motifs and tastant-binding domains of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, *Biochimie* 80:289-293 (1998)), subtilisin protease recognition motif (see, e.g., Polyak, *Protein Eng.* 10:615-619 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, *Biochemistry* 34:1787-1797 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature, see, e.g., Kroll, *DNA Cell. Biol.* 12:441-53 (1993).

Expression vectors, either as individual expression vectors or as libraries of expression vectors, comprising the ligand-binding domain encoding sequences may be introduced into a genome or into the cytoplasm or a nucleus of a cell and expressed by a variety of conventional techniques, well described in the scientific and patent literature. See, e.g., Roberts, *Nature* 328:731 (1987); Berger supra; Schneider, *Protein Eprr. Purif.* 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault, *Gene* 190:315-317 (1997); Aubrecht, *J. Pharmacol. Exp. Ther.* 281:992-997 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T1R ligand-binding domain within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, *Protein Sci.* 2:55-70 (1993). Other alignment and modeling algorithms are well known in the art, see, e.g., Peitsch, Receptors Channels 4:161-164 (1996); Kyte & Doolittle, *J. Md. Bio.*, 157:105-132 (1982); Cronet, Protein Eng. 6:59-64 (1993) (homology and "discover modeling.

The present invention also includes not only the DNA and proteins having the specified nucleic and amino acid sequences, but also DNA fragments, particularly fragments of, e.g., 40, 60, 80, 100, 150, 200, or 250 nucleotides, or more, as well as protein fragments of, e.g., 10, 20, 30, 50, 70, 100, or 150 amino acids, or more. Optionally, the nucleic acid fragments can encode an antigenic polypeptide which is capable of binding to an antibody raised against a T1R family member. Further, a protein fragment of the invention can optionally be an antigenic fragment which is capable of binding to an antibody raised against a T1R family member.

Also contemplated are chimeric proteins, comprising at least 10, 20, 30, 50, 70, 100, or 150 amino acids, or more, of one of at least one of the T1R polypeptides described herein, coupled to additional amino acids representing all or part of another GPCR, preferably a member of the 7 transmembrane superfamily. These chimeras can be made from the instant receptors and another GPCR, or they can be made by combining two or more of the present receptors. In one embodiment, one portion of the chimera corresponds tom or is derived from the extracellular domain of a T1R polypeptide of the invention. In another embodiment, one portion of the chimera corresponds to, or is derived from the extracellular domain and one or more of the transmembrane domains of a T1R polypeptide described herein, and the remaining portion or portions can come from another GPCR. Chimeric receptors are well known in the art, and the techniques for creating them and the selection and boundaries of domains or fragments of G protein-coupled receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

For example, a domain such as a ligand-binding domain, an extracellular domain, a transmembrane domain, a transmembrane domain, a cytoplasmic domain, an N-terminal domain, a C-terminal domain, or any combination thereof, can be covalently linked to a heterologous protein. For instance, an T1R extracellular domain can be linked to a heterologous GPCR transmembrane domain, or a heterologous GPCR extracellular domain can be linked to a T1R transmembrane domain. Other heterologous proteins of choice can include, e.g., green fluorescent protein, β-gal, glutamate receptor, and the rhodopsin presequence.

Also within the scope of the invention are host cells for expressing the T1Rs, fragments, or variants of the invention. To obtain high levels of expression of a cloned gene or nucleic acid, such as cDNAs encoding the T1Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. However, bacterial or eukaryotic expression systems can be used.

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T1R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

D. Detection of T1R Polypeptides

In addition to the detection of T1R genes and gene expression using nucleic acid hybridization technology, one can also use immunoassays to detect T1Rs, e.g., to identify taste receptor cells, and variants of T1R family members. Immunoassays can be used to qualitatively or quantitatively analyze the T1Rs. A general overview of the applicable technology can be found in Harlow & Lane, Antibodies: A Laboratory Manual (1988).

1. Antibodies to T1R Family Members

Methods of producing polyclonal and monoclonal antibodies that react specifically with a T1R family member are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature*, 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science*, 246:1275-1281 (1989); Ward et al., *Nature*, 341:544-546 (1989)).

A number of T1R-comprising immunogens may be used to produce antibodies specifically reactive with a T1R family member. For example, a recombinant T1R polypeptide, or an antigenic fragment thereof, can be isolated as described herein. Suitable antigenic regions include, e.g., the consensus sequences that are used to identify members of the T1R family. Recombinant proteins can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. For example, an inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the T1R. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen may be immortalized, commonly by fusion with a myeloma cell (see Kohler & Milstein, *Eur. J. Immunol.*, 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science*, 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of 104 or greater are selected and tested for their cross reactivity against non-T1R polypeptides, or even other T1R family members or other related proteins from other organisms, using a competitive binding immunoassay. Specific polyclonal antisera and monoclonal antibodies will usually bind with a Kd of at least about 0.1 mM, more usually at least about 1 pM, optionally at least about 0.1 p.M or better, and optionally 0.01 pM or better.

Once T1R family member specific antibodies are available, individual T1R proteins and protein fragments can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

2. Immunological Binding Assays

T1R proteins, fragments, and variants can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case a T1R family member or an antigenic subsequence thereof). The antibody (e.g., anti-T1R) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled T1R polypeptide or a labeled anti-T1R antibody. Alternatively, the labeling agent may be a third moiety, such as a secondary antibody, that specifically binds to the antibody/T1R complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.*, 111:1401-1406 (1973); Akerstrom et al., *J. Immunol.*, 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

a. Non-Competitive Assay Formats

Immunoassays for detecting a T1R polypeptide in a sample may be either competitive or noncompetitive. Non-competitive immunoassays are assays in which the amount of antigen is directly measured. In one preferred "sandwich" assay, for example, the anti-T1R antibodies can be bound directly to a solid substrate on which they are immobilized. These immobilized antibodies then capture the T1R polypeptide present in the test sample. The T1R polypeptide is thus immobilized is then bound by a labeling agent, such as a second T1R antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

b. Competitive Assay Formats

In competitive assays, the amount of T1R polypeptide present in the sample is measured indirectly by measuring the amount of a known, added (exogenous) T1R polypeptide displaced (competed away) from an anti-T1R antibody by the unknown T1R polypeptide present in a sample. In one competitive assay, a known amount of T1R polypeptide is added to a sample and the sample is then contacted with an antibody that specifically binds to the T1R. The amount of exogenous T1R polypeptide bound to the antibody is inversely proportional to the concentration of T1R polypeptide present in the sample. In a particularly preferred embodiment, the antibody is immobilized on a solid substrate. The amount of T1R polypeptide bound to the antibody may be determined either by measuring the amount of T1R polypeptide present in a T1R/antibody complex, or alternatively by measuring the amount of remaining uncomplexed protein. The amount of T1R polypeptide may be detected by providing a labeled T1R molecule.

A hapten inhibition assay is another preferred competitive assay. In this assay the known T1R polypeptide is immobilized on a solid substrate. A known amount of anti-T1R antibody is added to the sample, and the sample is then contacted with the immobilized T1R. The amount of anti-T1R antibody bound to the known immobilized T1R polypeptide is inversely proportional to the amount of T1R polypeptide present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

c. Cross-Reactivity Determinations

Immunoassays in the competitive binding format can also be used for cross-reactivity determinations. For example, a protein at least partially encoded by the nucleic acid sequences disclosed herein can be immobilized to a solid support. Proteins (e.g., T1R polypeptides and homologs) are added to the assay that compete for binding of the antisera to the immobilized antigen. The ability of the added proteins to compete for binding of the antisera to the immobilized protein is compared to the ability of the T1R polypeptide encoded by the nucleic acid sequences disclosed herein to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs. In addition, peptides comprising amino acid sequences representing conserved motifs that are used to identify members of the T1R family can be used in cross-reactivity determinations.

The immunoabsorbed and pooled antisera are then used in a competitive binding immunoassay as described above to compare a second protein, thought to be perhaps an allele or polymorphic variant of a T1R family member, to the immunogen protein (i.e., T1R polypeptide encoded by the nucleic acid sequences disclosed herein). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by nucleic acid sequences disclosed herein required to inhibit 50% of binding, then the second protein is said to specifically bind to the polyclonal antibodies generated to a T1R immunogen.

Antibodies raised against T1R conserved motifs can also be used to prepare antibodies that specifically bind only to GPCRs of the T1R family, but not to GPCRs from other families.

Polyclonal antibodies that specifically bind to a particular member of the T1R family can be made by subtracting out cross-reactive antibodies using other T1R family members. Species-specific polyclonal antibodies can be made in a similar way. For example, antibodies specific to human T1R1 can be made by, subtracting out antibodies that are cross-reactive with orthologous sequences, e.g., rat T1R1 or mouse T1R1.

d. Other Assay Formats

Western blot (immunoblot) analysis is used to detect and quantify the presence of T1R polypeptide in the sample. The technique generally comprises separating sample proteins by gel electrophoresis on the basis of molecular weight, transferring the separated proteins to a suitable solid support, (such as a nitrocellulose filter a nylon filter, or derivatized nylon filter), and incubating the sample with the antibodies that specifically bind the T1R polypeptide. The anti-T1R polypeptide antibodies specifically bind to the T1R polypeptide on the solid support. These antibodies may be directly labeled or alternatively may be subsequently detected using labeled antibodies (e.g., labeled sheep anti-mouse antibodies) that specifically bind to the anti-T1R antibodies.

Other, assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.*, 5:34-41 (1986)).

e. Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

f. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most any label useful in such methods can be applied to the present invention. Thus, a label is any composition detectable by spectroscopic, photochemical, biochemical, immunochemical, electrical, optical, or chemical means. Useful labels in the present invention include magnetic beads (e.g., DYNABEADS™), fluorescent dyes (e.g., fluorescein isothiocyanate, Texas red, rhodamine, and the like), radiolabels (e.g., 3H, 125I, 3sS, 14C, or $^{32}$P), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a T1R polypeptide, or secondary antibodies that recognize anti-T1R.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by, samples comprising the target antibodies. In this format, none of the components need be labeled and the presence of the target antibody is detected by simple visual inspection.

E. Detection of Modulators

Compositions and methods for determining whether a test compound specifically binds to a chemosensory receptor of the invention, both in vitro and in vivo, are described below. Many aspects of cell physiology can be monitored to assess the effect of ligand binding to a T1R polypeptide of the invention. These assays may be performed on intact cells expressing a chemosensory receptor, on permeabilized cells, or on membrane fractions produced by standard methods.

Taste receptors bind tastants and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

The T1R proteins or polypeptides of the assay will typically be selected from a polypeptide having a sequence of SEQ ID NOS: 4, 10, 12, 14, 17, or fragments or conservatively modified variants thereof. Optionally, the fragments and variants can be antigenic fragments and variants which bind to an anti-T1R antibody.

Alternatively, the T1R proteins or polypeptides of the assay can be derived from a eukaryote host cell and can include an amino acid subsequence having amino acid sequence identity to SEQ ID NOS: 4, 10, 12, 14, 17, or fragments or conservatively modified variants thereof. Generally, the amino acid sequence identity will be at least 35 to 50%, or optionally 75%, 85%, 90%, 95%, 96%, 97%, 98%, or 99%. Optionally, the T1R proteins or polypeptides of the assays can comprise a domain of a T1R protein, such as an extracellular domain, transmembrane region, transmembrane domain, cytoplasmic domain, ligand-binding domain, and the like. Further, as described above, the T1R protein or a domain thereof can be covalently linked to a heterologous protein to create a chimeric protein used in the assays described herein.

Modulators of T1R receptor activity are tested using T1R proteins or polypeptides as described above, either recombinant or naturally occurring. The T1R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vive assays described herein.

1. In Vitro Binding Assays

Taste transduction can also be examined in vitro with soluble or solid state reactions, using a T1R polypeptide of the invention. In a particular embodiment, a T1R ligand-binding domain can be used in vitro in soluble or solid state reactions to assay for ligand binding.

For instance, the T1R N-terminal domain is predicted to be involved in ligand binding. More particularly, the T1Rs belong to a GPCR sub-family that is characterized by large, approximately 600 amino acid, extracellular N-terminal segments. These N-terminal segments are thought to form, at least in part, the ligand-binding domains, and are therefore useful in biochemical assays to identify T1R agonists and antagonists. The ligand-binding domain may also contain additional portions of the extracellular domain, such as the extracellular loops of the transmembrane domain. Similar assays have been used with other GPCRs that are related to the T1Rs, such as the metabotropic glutamate receptors (see. e.g., Han and Hampson, *J. Biol. Chem.* 274:10008-10013 (1999)). These assays might involve displacing a radioactively or fluorescently labeled ligand, measuring changes in intrinsic fluorescence or changes in proteolytic susceptibility, etc.

Ligand binding to a T1R polypeptide of the invention can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties. Preferred binding assays of the invention are biochemical binding assays that use recombinant soluble N-terminal T1R domains.

Receptor-G protein interactions can also be examined. For example, binding of the G protein to the receptor, or its release from the receptor can be examined. More particularly, in the absence of GTP, an activator will lead to the formation of a tight complex of a G protein (all three subunits) with the receptor. This complex can be detected in a variety of ways, as noted above. Such an assay can be modified to search for inhibitors, e.g., by adding an activator to the receptor and G protein in the absence of GTP, which form a tight complex, and then screen for inhibitors by looking at dissociation of the receptor-G protein complex. In the presence of GTP, release of the alpha subunit of the G protein from the other two G protein subunits serves as a criterion of activation. An activated or inhibited G protein will in turn alter the properties of target enzymes, channels, and other effector proteins.

In another embodiment of the invention, a GTPγS assay may be used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively-labeled GTPγ$^{35}$S to the G protein in the presence of a putative ligand. Typically, membranes containing the chemosensory receptor of interest are mixed with a complex of G proteins. Potential inhibitors and/or activators and GTPγS are added to the assay, and binding of GTPγS to the G protein is measured. Binding can be measured by liquid scintillation counting or by any other means known in the art, including scintillation proximity assays (SPA). In other assays formats, fluorescently-labeled GTPγS can be utilized.

2. Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T1R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor tastant-binding which may activate or inhibit the chemosensory receptors of the invention, fluorescence-labeled tastants or auto-fluorescent tastants may be used.

Fluorescence polarization (P) is defined as:

$$P = \frac{Int_\parallel - Int_\perp}{Int_\parallel + Int_\perp}$$

Where Π is the intensity of the emission light parallel to the excitation light plane and Int ⊥ is the intensity of the emission light perpendicular to the excitation light plane. P, being a ratio of light intensities, is a dimensionless number. For example, the Beacon® and Beacon 2000™ System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236-240, which gives a thorough explanation of this equation. Summarily, the Perrin equation states that polarization is directly proportional to the rotational relaxation time, the time that it takes a molecule to rotate through an angle of approximately 68.50 Rotational relaxation time is related to viscosity (η), absolute temperature (T), molecular volume (V), and the gas constant (R) by the following equation:

$$\text{Rotational Relaxation Time} = \frac{3\eta V}{RT}$$

The rotational relaxation time is small (≈1 nanosecond) for small molecules (e.g. fluorescein) and large (≈100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

3. Solid State and Soluble High Throughput Assays

In yet another embodiment, the invention provides soluble assays using a T1R polypeptide; or a cell or tissue expressing an T1R polypeptide. In another embodiment, the invention provides solid phase based in vitro assays in a high throughput format, where the T1R polypeptide, or cell or tissue expressing the T1R polypeptide is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.*, 85:2149-2154 (1963) (describing solid phase synthesis of, e.g., peptides); Geysen et al., *J. Immun. Meth.*, 102:259-274 (1987) (describing synthesis of solid phase components on pins); Frank & Doring, *Tetrahedron*, 44:60316040 (1988) (describing synthesis of various peptide sequences on cellulose disks); Fodor et al., *Science*, 251:767-777 (1991); *Sheldon et al., Clinical Chemistry*, 39(4):718-719 (1993); and Kozal et al., *Nature Medicine*, 2(7):753759 (1996) (all describing arrays of biopolymers fixed to solid substrates). Non-chemical approaches for fixing tag binders to substrates include other common methods, such as heat, cross-linking by UV radiation, and the like.

4. Computer-Based Assays

Yet another assay for compounds that modulate T1R polypeptide activity involves computer assisted compound design, in which a computer system is used to generate a three-dimensional structure of an T1R polypeptide based on the structural information encoded by its amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a T1R polypeptide into the computer system. The nucleotide sequence encoding the T1R polypeptide, or the amino acid sequence thereof, can be any sequence disclosed herein, and conservatively modified versions thereof.

The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand-binding regions are identified by the computer system. Three-dimensional structures for potential ligands are generated by entering amino acid or nucleotide sequences or chemical formulas of compounds, as described above. The three-dimensional structure of the potential ligand is then compared to that of the T1R polypeptide to identify ligands that bind to the protein. Binding affinity between the protein and ligands is determined using energy terms to determine which ligands have an enhanced probability of binding to the protein.

Computer systems are also used to screen for mutations, polymorphic variants, alleles, and interspecies homologs of T1R genes. Such mutations can be associated with disease states or genetic traits. As described above, GeneChip™ and related technology can also be used to screen for mutations, polymorphic variants, alleles, and interspecies homologs. Once the variants are identified, diagnostic assays can be used to identify patients having such mutated genes. Identification of the mutated T1R genes involves receiving input of a first nucleic acid or amino acid sequence of a T1R gene, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various T1R genes, and mutations associated with disease states and genetic traits.

5. Cell-Based Binding Assays

In one embodiment, a T1R protein or polypeptide is expressed in a eukaryotic cell as a chimeric receptor with a heterologous, chaperone sequence that facilitates its maturation and targeting through the secretory pathway. Such chimeric T1R polypeptides can be expressed in any eukaryotic cell, such as human kidney two hundred ninety three cells. Preferably, the cells comprise a functional G protein, e.g., Gα15, that is capable of coupling the chimeric receptor to an intracellular signaling pathway or to a signaling protein such as phospholipase C. Activation of such chimeric receptors in such cells can be detected using any standard method, such as by detecting changes in intracellular calcium by detecting FURA-2 dependent fluorescence in the cell.

Activated GPCR receptors become substrates for kinases that phosphorylate the C-terminal tail of the receptor (and possibly other sites as well). Thus, activators will promote the transfer of 32P from gamma-labeled GTP to the receptor, which can be assayed with a scintillation counter. The phosphorylation of the C-terminal tail will promote the binding of arrestin-like proteins and will interfere with the binding of G proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., *Methods in Enzymology*, vols. 237 and 238 (1994) and volume 96 (1983); Bourne et al., *Nature*, 10:349:117-27 (1991); Bourne et al., *Nature*, 348:125-32 (1990); Pitcher et al., *Annu. Rev. Biochem.*, 67:653-92 (1998).

T1R modulation may be assayed by comparing the response of a T1R polypeptide treated with a putative T1R modulator to the response of an untreated control sample. Such putative T1R modulators can include tastants that either inhibit or activate T1R polypeptide activity. In one embodiment, control samples (untreated with activators or inhibitors) are assigned a relative T1R activity value of 100. Inhibition of a T1R polypeptide is achieved when the T1R activity value relative to the control is about 90%, optionally 50%, optionally 25-0%. Activation of a T1R polypeptide is achieved when the T1R activity value relative to the control is 110%, optionally 150%, 200-500%, or 1000-2000%.

Changes in ion flux may be assessed by determining changes in ionic polarization (i.e., electrical potential) of the cell or membrane expressing a T1R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., *New Engl. J Med.*, 336:1575-1595 (1997)). Whole cell currents are conveniently determined using the standard. Other known assays include: radiolabeled ion flux assays and fluorescence assays using voltage-sensitive dyes (see, e.g., Vestergarrd-Bogind et al., *J. Membrane Biol.*, 88:67-75 (1988); Gonzales & Tsien, *Chem. Biol.*, 4:269277 (1997); Daniel et al., *J. Pharmacol. Meth.*, 25:185-193 (1991); Holevinsky et al., *J. Membrane Biology*, 137:59-70 (1994)). Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein-coupled receptors, promiscuous G proteins such as Gα15 and Gα16 can be used in the assay of choice (Wilkie et al., *Proc. Nat'l Acad Sci.*, 88:10049-10053 (1991)). Such promiscuous G proteins allow coupling of a wide range of receptors.

Receptor activation typically initiates subsequent intracellular events, e.g., increases in second messengers such as IP3, which releases intracellular stores of calcium ions. Activation of some G protein-coupled receptors stimulates the formation of inositol triphosphate (IP3) through phospholipase C-mediated hydrolysis of phosphatidylinositol (Berridge & Irvine, *Nature*, 312:315-21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Nat'l Acad. Sci.*, 88:9868-9872 (1991) and Dhallan et al., *Nature*, 347:184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a preferred embodiment, T1R polypeptide activity is measured by expressing a T1R gene in a heterologous cell with a promiscuous G protein that links the receptor to a phospholipase C signal transduction pathway (see Offermanns & Simon, *J. Biol. Chem.*, 270:15175-15180 (1995)). Optionally the cell line is human kidney two hundred ninety the (which does not naturally express T1R genes) and the promiscuous G protein is G$\alpha$15 (Offermanns & Simon, supra). Modulation of taste transduction, is assayed by measuring changes in intracellular $Ca^{2+}$ levels, which change in response to modulation of the T1R signal transduction pathway via administration of a molecule that associates with a T1R polypeptide. Changes in $Ca^{2-}$ levels are optionally measured using fluorescent $Ca^{2+}$ indicator dyes and fluorometric imaging.

In one embodiment, the changes in intracellular cAMP or cGMP can be measured using immunoassays. The method described in Offermanns & Simon, *J. Bio. Chem.*, 270: 15175-15180 (1995), may be used to determine the level of cAMP. Also, the method described in Felley-Bosco et al., *Am. J. Resp. Cell and Mol. Biol.*, 11:159-164 (1994), may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

In another embodiment, transcription levels can be measured to assess the effects of a test compound on signal transduction. A host cell containing a T1R polypeptide of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, '3-galactosidase and alkaline phosphatase. Furthermore, the protein of interest can be used as an indirect reporter via attachment to a second reporter such as green fluorescent protein (see, e.g., Mistili & Spector, *Nature Biotechnology*, 15:961-964 (1997)).

The amount of transcription is then compared to the amount of transcription in either the same cell in the absence of the test compound, or it may be compared with the amount of transcription in a substantially identical cell that lacks the T1R polypeptide of interest. A substantially identical cell may be derived from the same cells from which the recombinant cell was prepared but which had not been modified by introduction of heterologous DNA. Any difference in the amount of transcription indicates that the test compound has in some manner altered the activity of the T1R polypeptide of interest.

6. Transgenic Non-Human Animals Expressing Chemosensory Receptors

Non-human animals expressing one or more chemosensory receptor sequences of the invention, can also be used for receptor assays. Such expression can be used to determine whether a test compound specifically binds to a mammalian taste transmembrane receptor polypeptide in vivo by contacting a non-human animal stably or transiently transfected with a nucleic acid encoding a chemosensory receptor or ligand-binding region thereof with a test compound and determining whether the animal reacts to the test compound by specifically binding to the receptor polypeptide.

Animals transfected or infected with the vectors of the invention are particularly useful for assays to identify and characterize tastants/ligands that can bind to a specific or sets of receptors. Such vector-infected animals expressing human chemosensory receptor sequences can be used for in vivo screening of tastants and their effect on, e.g., cell physiology (e.g., on taste neurons), on the CNS, or behavior.

Means to infect/express the nucleic acids and vectors, either individually or as libraries, are well known in the art. A variety of individual cell, organ, or whole animal parameters can be measured by a variety of means. The T1R sequences of the invention can be for example expressed in animal taste tissues by delivery with an infecting agent, e.g., adenovirus expression vector.

The endogenous chemosensory receptor genes can remain functional and wild-type (native) activity can still be present. In other situations, where it is desirable that all chemosensory receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, *Transgenic Res* 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, *Hum. Mol. Genet.* 7:53-62 (1998); Moreadith, *J. Mol. Med.* 75:208-216 (1997); Tojo, *Cytotechnology* 19:161-165 (1995); Mudgett, *Methods Mol. Biol.* 48:167-184 (1995); Longo, *Transgenic Res.* 6:321-328 (1997); U.S. Pat. Nos. 5,616,491; 5,464,764; 5,631,153; 5,487,992; 5,627,059; 5,272,071; WO 91/09955; WO93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T1R gene sequences can replace the orthologous T1R in the mouse genome. In this way, a mouse expressing a human or rat T1R is produced. This mouse can then be used to analyze the function of human or rat T1Rs, and to identify ligands for such T1Rs.

F. Modulators

The compounds tested as modulators of a T1R family member can be any small chemical compound, or a biological entity, such as a protein, sugar, nucleic acid or lipid. Alternatively, modulators can be genetically altered versions of a T1R gene. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487-493 (1991) and Houghton et al., *Nature*, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci.*, 90:6909-6913 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.*, 114:9217-9218 (1992)), analogous organic syntheses of small compound libraries (Chen et al., *J. Amer. Chem. Soc.*, 116:2661 (1994)), oligocarbamates (Cho et al., *Science*, 261:1303 (1993)), peptidyl phosphonates (Campbell et al., *J. Org. Chem.*, 59:658 (1994)), nucleic acid libraries (Ausubel, Berger and Sambrook, all supra), peptide nucleic acid libraries (U.S. Pat. No. 5,539,083), antibody libraries (Vaughn et al., *Nature Biotechnology*, 14(3):309-314 (1996) and PCT/US96/10287), carbohydrate libraries (Liang et al., *Science*, 274:1520-1522 (1996) and U.S. Pat. No. 5,593, 853), small organic molecule libraries (benzodiazepines, Baum, *C&EN*, January 18, page 33 (1993); thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T1R modulators can be used in any food product, confectionery, pharmaceutical composition, or ingredient thereof to thereby modulate the taste of the product, composition, or ingredient in a desired manner. For instance, T1R modulators which enhance sweet taste sensation can be added to sweeten a product or composition, while T1R modulators which block undesirable taste sensations can be added to improve the taste of a product or composition.

G. Methods for Representing and Predicting the Perception of Taste

The invention also preferably provides methods for representing the perception of taste and/or for predicting the perception of taste in a mammal, including in a human. Preferably, such methods may be performed by using the receptors and genes encoding said T1R polypeptides disclosed herein.

Also contemplated as within the invention, is a method of screening one or more compounds for the presence of a taste detectable by a mammal, comprising: contacting said one or more compounds with the disclosed receptors, preferably wherein the mammal is a human. Also contemplated as within the invention, is a method for representing taste perception of a particular taste in a mammal, comprising the steps of: providing values $X_1$ to $X_n$ representative of the quantitative stimulation of each of n chemosensory receptors of said vertebrate, where n is greater than or equal to 2; and generating from said values a quantitative representation of taste perception. The chemosensory receptors may be a chemosensory receptor disclosed herein, the representation may constitutes a point or a volume in n-dimensional space, may constitutes a graph or a spectrum, and may constitutes a matrix of quantitative representations. Also, the providing step may comprise contacting a plurality of recombinantly-produced chemosensory receptors with a test composition and quantitatively measuring the interaction of said composition with said receptors.

Also contemplated as within the invention, is a method for predicting the taste perception in a mammal generated by one or more molecules or combinations of molecules yielding unknown taste perception in a mammal, comprising the steps of: providing values $X_1$ to $X_n$ representative of the quantitative stimulation of each of n chemosensory receptors of said vertebrate, where n is greater than or equal to 2, for one or more molecules or combinations of molecules yielding known taste perception in a mammal; and generating from said values a quantitative representation of taste perception in a mammal for the one or more molecules or combinations of molecules yielding known taste perception in a mammal, providing values $X_1$ to $X_n$ representative of the quantitative stimulation of each of n chemosensory receptors of said vertebrate, where n is greater than or equal to 2, for one or more molecules or combinations of molecules yielding unknown taste perception in a mammal; and generating from said values a quantitative representation of taste perception in a mammal for the one or more molecules or combinations of molecules yielding unknown taste perception in a mammal, and predicting the taste perception in a mammal generated by one or more molecules or combinations of molecules yielding unknown taste perception in a mammal by comparing the quantitative representation of taste perception in a mammal for the one or more molecules or combinations of molecules yielding unknown taste perception in a mammal to the quantitative representation of taste perception in a mammal for the one or more molecules or combinations of molecules yielding known taste perception in a mammal. The chemosensory receptors used in this method may include a chemosensory receptor disclosed herein.

In another embodiment, novel molecules or combinations of molecules are generated which elicit a predetermined taste perception in a mammal by determining a value of taste perception in a mammal for a known molecule or combinations of molecules as described above; determining a value of taste perception in a mammal for one or more unknown molecules or combinations of molecules as described above; comparing the value of taste perception in a mammal for one or more unknown compositions to the value of taste perception in a mammal for one or more known compositions; selecting a molecule or combination of molecules that elicits a predetermined taste perception in a mammal; and combining two or more unknown molecules or combinations of molecules to form a molecule or combination of molecules that elicits a predetermined taste perception in a mammal. The combining step yields a single molecule or a combination of molecules that elicits a predetermined taste perception in a mammal.

In another embodiment of the invention, there is provided a method for simulating a taste, comprising the steps of: for each of a plurality of cloned chemosensory receptors, preferably human receptors, ascertaining the extent to which the receptor interacts with the tastant; and combining a plurality of compounds, each having a previously-ascertained interaction with one or more of the receptors, in amounts that together provide a receptor-stimulation profile that mimics the profile for the tastant. Interaction of a tastant with a chemosensory receptor can be determined using any of the binding or reporter assays described herein. The plurality of compounds may then be combined to form a mixture. If desired, one or more of the plurality of the compounds can be combined covalently. The combined compounds substantially stimulate at least 75%, 80%, or 90% of the receptors that are substantially stimulated by the tastant.

In another preferred embodiment of the invention, a plurality of standard compounds are tested against a plurality of chemosensory receptors to ascertain the extent to which the receptors each interact with each standard compound, thereby generating a receptor stimulation profile for each standard compound. These receptor stimulation profiles may then be stored in a relational database on a data storage medium. The method may further comprise providing a desired receptor-stimulation profile for a taste; comparing the desired receptor stimulation profile to the relational database; and ascertaining one or more combinations of standard compounds that most closely match the desired receptor-stimulation profile. The method may further comprise combining standard compounds in one or more of the ascertained combinations to simulate the taste.

H. Kits

T1R genes and their homologs are useful tools for identifying chemosensory receptor cells, for forensics and paternity determinations, and for examining taste transduction. T1R family member-specific reagents that specifically hybridize to T1R nucleic acids, such as T1R probes and primers, and T1R specific reagents that specifically bind to a T1R polypeptide, e.g., T1R antibodies are used to examine taste cell expression and taste transduction regulation.

Nucleic acid assays for the presence of DNA and RNA for a T1R family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques*, 4:230250 (1986); Haase et al., *Methods in Virology*, vol. VII, pp. 189-226 (1984); and *Nucleic Acid Hybridization: A Practical Approach* (Names et al., eds. 1987). In addition, a T1R polypeptide can be detected with the various immunoassay techniques described above. The test sample is typically compared to both a positive control (e.g., a sample expressing a recombinant T1R polypeptide) and a negative control.

The present invention also provides for kits for screening for modulators of T1R family members. Such kits can be prepared from readily available materials and reagents. For example, such kits can comprise any one or more of the following materials: T1R nucleic acids or proteins, reaction tubes, and instructions for testing T1R activity. Optionally, the kit contains a biologically active T1R receptor. A wide variety of kits and components can be prepared according to the present invention, depending upon the intended user of the kit and the particular needs of the user.

EXAMPLES

In the protein sequences presented herein, the one-letter code X or Xaa refers to any of the twenty common amino acid residues. In the DNA sequences presented herein, the one letter codes N or n refers to any of the of the four common nucleotide bases, A, T, C, or G.

Example 1—hT1R3

The hT1R3 genomic DNA is provided below as SEQ ID NO 1 and SEQ ID NO 2 with predicted coding sequences (cds) shown in boldface. The break between the 5' and 3' contigs is shown as ellipses (' . . . '). The hT1R3 predicted cds are described in SEQ ID NO 3. Finally, a preferred, predicted hT1R3 amino acid sequence is provided as SEQ ID NO 4, using the one-letter code for the amino acids.

hT1R3 genomic DNA-5' contig (SEQ ID NO 1)

(SEQ ID NO: 1)

AGCCTGGCAGTGGCCTCAGGCAGAGTCTGACGCGCACAAACTTTCAGGCCCAGGAAGCGA
GGACACCACTGGGGCCCCAGGGTGTGGCAAGTGAGGATGGCAAGGGTTTTGCTAAACAAA
TCCTCTGCCCGCTCCCCGCCCCGGGCTCACTCCATGTGAGGCCCCAGTCGGGGCAGCCACC
TGCCGTGCCTGTTGGAAGTTGCCTCTGCCATGCTGGGCCCTGCTGTCCTGGGCCTCAGC
CTCTGGGCTCTCCTGCACCCTGGGACGGGGGCCCCATTGTGCCTGTCACAGCAACTT
AGGATGAAGGGGGACTACGTGCTGGGGGGGCTGTTCCCCCTGGGCGAGGCCGAGGA
GGCTGGCCTCCGCAGCCGGACACGGCCCAGCAGCCCTGTGTGCACCAGGTACAGAGG
TGGGACGGCCTGGGTCGGGGTCAGGGTGACCAGGTCTGGGGTGCTCCTGAGCTGGGGCCG
AGGTGGCCATCTGCGGTTCTGTGTGGCCCCAGGTTCTCCTCAAACGGCCTGCTCTGGGC
ACTGGCCATGAAAATGGCCGTGGAGGAGATCAACAACAAGTCGGATCTGCTGCCCGG
GCTGCGCCTGGGCTACGACCTCTTTGATACGTGCTCGGAGCCTGTGGTGGCCATGAA
GCCCAGCCTCATGTTCCTGGCCAAGGCAGGCAGCCGCGACATCGCCGCCTACTGCAA
CTACACGCAGTACCAGCCCCGTGTGCTGGCTGTCATCGGGCCCCACTCGTCAGAGCT
CGCCATGGTCACCGGCAAGTTCTTCAGCTTCTTCCTCATGCCCCAGTGGGGCGCCCCC
CACCATCACCCACCCCCAACCAACCCCTGCCCCGTGGGAGCCCCTTGTGTCAGGAGAATGC hT1R3 genomic DNA-3' contig (SEQ ID NO 2)

(SEQ ID NO 2)

...............TACATGCACCCCACCCAGCCCTGCCCTGGGAGCCCTGTGTCAGAAGATGC
TCTTGGCCTTGCAGGTCAGCTACGGTGCTAGCATGGAGCTGCTGAGCGCCCGGGAGAC
CTTCCCCTCCTTCTTCCGCACCGTGCCCAGCGACCGTGTGCAGCTGACGGCCGCCGC
GGAGCTGCTGCAGGAGTTCGGCTGGAACTGGGTGGCCGCCCTGGGCAGCGACGACG
AGTACGGCCGGCAGGGCCTGAGCATCTTCTCGGCCCTGGCCGCGGCACGCGGCATCT
GCATCGCGCACGAGGGCCTGGTGCCGCTGCCCCGTGCCGATGACTCGCGGCTGGGG
AAGGTGCAGGACGTCCTGCACCAGGTGAACCAGAGCAGCGTGCAGGTGGTGCTGCT
GTTCGCCTCCGTGCACGCCGCCCACGCCCTCTTCAACTACAGCATCAGCAGCAGGCT
CTCGCCCAAGGTGTGGGTGGCCAGCGAGGCCTGGCTGACCTCTGACCTGGTCATGGG
GCTGCCCGGCATGGCCCAGATGGGCACGGTGCTTGGCTTCCTCCAGAGGGGTGCCCA
GCTGCACGAGTTCCCCCAGTACGTGAAGACGCACCTGGCCCTGGCCACCGACCCGGC
CTTCTGCTCTGCCCTGGGCGAGAGGGAGCAGGGTCTGGAGGAGGACGTGGTGGGCC
AGCGCTGCCCGCAGTGTGACTGCATCACGCTGCAGAACGTGAGCGCAGGGCTAAATC
ACCACCAGACGTTCTCTGTCTACGCAGCTGTGTATAGCGTGGCCCAGGCCCTGCACA
ACACTCTTCAGTGCAACGCCTCAGGCTGCCCCGCGCAGGACCCCGTGAAGCCCTGGC
AGGTGAGCCCGGGAGATGGGGGTGTGCTGTCCTCTGCATGTGCCCAGGCCACCAGGCACG
GCCACCACGCCTGAGCTGGAGGTGGCTGGCGGCTCAGCCCCGTCCCCCGCCCGCAGCTCC
TGGAGAACATGTACAACCTGACCTTCCACGTGGGCGGGCTGCCGCTGCGGTTCGACA
GCAGCGGAAACGTGGACATGGAGTACGACCTGAAGCTGTGGGTGTGGCAGGGCTCA
GTGCCCAGGCTCCACGACGTGGGCAGGTTCAACGGCAGCCTCAGGACAGAGCGCCT
GAAGATCCGCTGGCACACGTCTGACAACCAGGTGAGGTGAGGGTGGGTGTGCCAGGCG
TGCCCGTGGTAGCCCCCGCGGCAGGGCGCAGCCTGGGGGTGGGGGCCGTTCCAGTCTGCC
GTGGGCATGCCCAGCCGAGCAGAGCCAGACCCCAGGCCTGTGCGCAGAAGCCCGTGTCC
CGGTGCTCGCGGCAGTGCCAGGAGGGCCAGGTGCGCCGGGTCAAGGGGTTCCACTC

CTGCTGCTACGACTGTGTGGACTGCGAGGCGGGCAGCTACCGGCAAAACCCAGGTGA

GCCGCCTTCCCGGCAGGCGGGGGTGGGAACGCAGCAGGGGAGGGTCCTGCCAAGTCCTGA

CTCTGAGACCAGAGCCCACAGGGTACAAGACGAACACCCAGCGCCCTTCTCCTCTCTCACA

GACGACATCGCCTGCACCTTTTGTGGCCAGGATGAGTGGTCCCCGGAGCGAAGCACA

CGCTGCTTCCGCCGCAGGTCTCGGTTCCTGGCATGGGGCGAGCCGGCTGTGCTGCTG

CTGCTCCTGCTGCTGAGCCTGGCGCTGGGCCTTGTGCTGGCTGCTTTGGGGCTGTTC

GTTCACCATCGGGACAGCCCACTGGTTCAGGCCTCGGGGGGGCCCCTGGCCTGCTTT

GGCCTGGTGTGCCTGGGCCTGGTCTGCCTCAGCGTCCTCCTGTTCCCTGGCCAGCCC

AGCCCTGCCCGATGCCTGGCCCAGCAGCCCTTGTCCCACCTCCCGCTCACGGGCTGC

CTGAGCACACTCTTCCTGCAGGCGGCCGAGATCTTCGTGGAGTCAGAACTGCCTCTG

AGCTGGGCAGACCGGCTGAGTGGCTGCCTGCGGGGCCCTGGGCCTGGCTGGTGGT

GCTGCTGGCCATGCTGGTGGAGGTCGCACTGTGCACCTGGTACCTGGTGGCCTTCCC

GCCGGAGGTGGTGACGGACTGGCACATGCTGCCCACGGAGGCGCTGGTGCACTGCC

GCACACGCTCCTGGGTCAGCTTCGGCCTAGCGCACGCCACCAATGCCACGCTGGCCT

TTCTCTGCTTCCTGGGCACTTTCCTGGTGCGGAGCCAGCCGGGCTGCTACAACCGTG

CCCGTGGCCTCACCTTTGCCATGCTGGCCTACTTCATCACCTGGGTCTCCTTTGTGCC

CCTCCTGGCCAATGTGCAGGTGGTCCTCAGGCCCGCCGTGCAGATGGGCGCCCTCCT

GCTCTGTGTCCTGGGCATCCTGGCTGCCTTCCACCTGCCCAGGTGTTACCTGCTCATG

CGGCAGCCAGGGCTCAACACCCCCGAGTTCTTCCTGGGAGGGGGCCCTGGGGATGC

CCAAGGCCAGAATGACGGGAACACAGGAAATCAGGGGAAACATGAGTGACCCAACCC

TGTGATCTCAGCCCCGGTGAACCCAGACTTAGCTGCGATCCCCCCCAAGCCAGCAATGACC

CGTGTCTCGCTACAGAGACCCTCCCGCTCTAGGTTCTGACCCCAGGTTGTCTCCTGACCCT

GACCCCACAGTGAGCCCTAGGCCTGGAGCACGTGGACACCCCTGTGACCATC hT1R3 full-length genomic DNA (SEQ ID NO 20)

(SEQ ID NO 20)

AGCCTGGCAGTGGCCTCAGGCAGAGTCTGACGCGCACAAACTTTCAGGCCCAGGAAGCGA

GGACACCACTGGGGCCCCAGGGTGTGGCAAGTGAGGATGGCAAGGGTTTTGCTAAACAAA

TCCTCTGCCCGCTCCCCGCCCCGGGCTCACTCCATGTGAGGCCCCAGTCGGGGCAGCCACC

TGCCGTGCCTGTTGGAAGTTGCCTCTGCCATGCTGGGCCCTGCTGTCCTGGGCCTCAGC

CTCTGGGCTCTCCTGCACCCTGGGACGGGGGCCCCATTGTGCCTGTCACAGCAACTT

AGGATGAAGGGGGACTACGTGCTGGGGGGGCTGTTCCCCCTGGGCGAGGCCGAGGA

GGCTGGCCTCCGCAGCCGGACACGGCCCAGCAGCCCTGTGTGCACCAGGTACAGAGG

TGGGACGGCCTGGGTCGGGGTCAGGGTGACCAGGTCTGGGGTGCTCCTGAGCTGGGGCCG

AGGTGGCCATCTGCGGTTCTGTGTGGCCCCAGGTTCTCCTCAAACGGCCTGCTCTGGGC

ACTGGCCATGAAAATGGCCGTGGAGGAGATCAACAACAAGTCGGATCTGCTGCCCGG

GCTGCGCCTGGGCTACGACCTCTTTGATACGTGCTCGGAGCCTGTGGTGGCCATGAA

GCCCAGCCTCATGTTCCTGGCCAAGGCAGGCAGCCGCGACATCGCCGCCTACTGCAA

CTACACGCAGTACCAGCCCCGTGTGCTGGCTGTCATCGGGCCCCACTCGTCAGAGCT

CGCCATGGTCACCGGCAAGTTCTTCAGCTTCTTCCTCATGCCCCAGTGGGGCGCCCC

CACCATCACCCACCCCCAACCAACCCCTGCCCCGTGGGAGCCCCTTGTGTCAGGAGAATGC

TACATGCACCCCACCCAGCCCTGCCCTGGGAGCCCTGTGTCAGAAGATGCTCTTGGCCTTG

-continued

```
CAGGTCAGCTACGGTGCTAGCATGGAGCTGCTGAGCGCCCGGGAGACCTTCCCCTCC

TTCTTCCGCACCGTGCCCAGCGACCGTGTGCAGCTGACGGCCGCCGCGGAGCTGCTG

CAGGAGTTCGGCTGGAACTGGGTGGCCGCCCTGGGCAGCGACGACGAGTACGGCCG

GCAGGGCCTGAGCATCTTCTCGGCCCTGGCCGCGGCACGCGGCATCTGCATCGCGCA

CGAGGGCCTGGTGCCGCTGCCCCGTGCCGATGACTCGCGGCTGGGGAAGGTGCAGG

ACGTCCTGCACCAGGTGAACCAGAGCAGCGTGCAGGTGGTGCTGCTGTTCGCCTCCG

TGCACGCCGCCCACGCCCTCTTCAACTACAGCATCAGCAGCAGGCTCTCGCCCAAGG

TGTGGGTGGCCAGCGAGGCCTGGCTGACCTCTGACCTGGTCATGGGGCTGCCCGGCA

TGGCCCAGATGGGCACGGTGCTTGGCTTCCTCCAGAGGGGTGCCCAGCTGCACGAGT

TCCCCCAGTACGTGAAGACGCACCTGGCCCTGGCCACCGACCCGGCCTTCTGCTCTG

CCCTGGGCGAGAGGGAGCAGGGTCTGGAGGAGGACGTGGTGGGCCAGCGCTGCCCG

CAGTGTGACTGCATCACGCTGCAGAACGTGAGCGCAGGGCTAAATCACCACCAGACG

TTCTCTGTCTACGCAGCTGTGTATAGCGTGGCCCAGGCCCTGCACAACACTCTTCAGT

GCAACGCCTCAGGCTGCCCCGCGCAGGACCCCGTGAAGCCCTGGCAGGTGAGCCCGG

GAGATGGGGGTGTGCTGTCCTCTGCATGTGCCCAGGCCACCAGGCACGGCCACCACGCCT

GAGCTGGAGGTGGCTGGCGGCTCAGCCCCGTCCCCGCCCGCAGCTCCTGGAGAACATGT

ACAACCTGACCTTCCACGTGGGCGGGCTGCCGCTGCGGTTCGACAGCAGCGGAAACG

TGGACATGGAGTACGACCTGAAGCTGTGGGTGTGGCAGGGCTCAGTGCCCAGGCTCC

ACGACGTGGGCAGGTTCAACGGCAGCCTCAGGACAGAGCGCCTGAAGATCCGCTGG

CACACGTCTGACAACCAGGTGAGGTGAGGGTGGGTGTGCCAGGCGTGCCCGTGGTAGCC

CCCGCGGCAGGGCGCAGCCTGGGGGTGGGGGCCGTTCCAGTCTCCCGTGGGCATGCCCAG

CCGAGCAGAGCCAGACCCCAGGCCTGTGCGCAGAAGCCCGTGTCCCGGTGCTCGCGGC

AGTGCCAGGAGGGCCAGGTGCGCCGGGTCAAGGGGTTCCACTCCTGCTGCTACGACT

GTGTGGACTGCGAGGCGGGCAGCTACCGGCAAAACCCAGGTGAGCCGCCTTCCCGGCA

GGCGGGGGTGGGAACGCAGCAGGGGAGGGTCCTGCCAAGTCCTGACTCTGAGACCAGAGC

CCACAGGGTACAAGACGAACACCCAGCGCCCTTCTCCTCTCTCACAGACGACATCGCCTG

CACCTTTTGTGGCCAGGATGAGTGGTCCCCGGAGCGAAGCACACGCTGCTTCCGCCG

CAGGTCTCGGTTCCTGGCATGGGCGAGCCGGCTGTGCTGCTGCTGCTCCTGCTGCT

GAGCCTGGCGCTGGGCCTTGTGCTGGCTGCTTTGGGGCTGTTCGTTCACCATCGGGA

CAGCCCACTGGTTCAGGCCTCGGGGGGCCCCTGGCCTGCTTTGGCCTGGTGTGCCT

GGGCCTGGTCTGCCTCAGCGTCCTCCTGTTCCCTGGCCAGCCCAGCCCTGCCCGATG

CCTGGCCCAGCAGCCCTTGTCCCACCTCCCGCTCACGGGCTGCCTGAGCACACTCTT

CCTGCAGGCGGCCGAGATCTTCGTGGAGTCAGAACTGCCTCTGAGCTGGGCAGACCG

GCTGAGTGGCTGCCTGCGGGGCCCTGGGCCTGGCTGGTGGTGCTGCTGGCCATGCT

GGTGGAGGTCGCACTGTGCACCTGGTACCTGGTGGCCTTCCCGCCGGAGGTGGTGAC

GGACTGGCACATGCTGCCCACGGAGGCGCTGGTGCACTGCCGCACACGCTCCTGGGT

CAGCTTCGGCCTAGCGCACGCCACCAATGCCACGCTGGCCTTTTCTCTGCTTCCTGGG

CACTTTCCTGGTGCGGAGCCAGCCGGGCTGCTACAACCGTGCCCGTGGCCTCACCTT

TGCCATGCTGGCCTACTTCATCACCTGGGTCTCCTTTGTGCCCCTCCTGGCCAATGTG

CAGGTGGTCCTCAGGCCCGCCGTGCAGATGGGCGCCCTCCTGCTCTGTGTCCTGGGC

ATCCTGGCTGCCTTCCACCTGCCCAGGTGTTACCTGCTCATGCGGCAGCCAGGGCTC
```

```
AACACCCCCGAGTTCTTCCTGGGAGGGGCCCTGGGGATGCCCAAGGCCAGAATGAC

GGGAACACAGGAAATCAGGGGAAACATGAGTGACCCAACCCTGTGATCTCAGCCCCGG

TGAACCCAGACTTAGCTGCGATCCCCCCCAAGCCAGCAATGACCCGTGTCTCGCTACAGAG

ACCCTCCCGCTCTAGGTTCTGACCCCAGGTTGTCTCCTGACCCTGACCCCACAGTGAGCCC

TAGGCCTGGAGCACGTGGACACCCCTGTGACCATC
``` hT1R3 predicted cds (SEQ ID NO 3)

(SEQ ID NO 3)
```
ATGCTGGGCCCTGCTGTCCTGGGCCTCAGCCTCTGGGCTCTCCTGCACCCTGGGACGGGGG

CCCCATTGTGCCTGTCACAGCAACTTAGGATGAAGGGGGACTACGTGCTGGGGGGGCTGT

TCCCCCTGGGCGAGGCCGAGGAGGCTGGCCTCCGCAGCCGGACACGGCCCAGCAGCCCTG

TGTGCACCAGGTTCTCCTCAAACGGCCTGCTCTGGGCACTGGCCATGAAAATGGCCGTGGA

GGAGATCAACAACAAGTCGGATCTGCTGCCCGGGCTGCGCCTGGGCTACGACCTCTTTGAT

ACGTGCTCGGAGCCTGTGGTGGCCATGAAGCCCAGCCTCATGTTCCTGGCCAAGGCAGGC

AGCCGCGACATCGCCGCCTACTGCAACTACACGCAGTACCAGCCCCGTGTGCTGGCTGTCA

TCGGGCCCCACTCGTCAGAGCTCGCCATGGTCACCGGCAAGTTCTTCAGCTTCTTCCTCAT

GCCCCACTACGGTGCTAGCATGGAGCTGCTGAGCGCCCGGGAGACCTTCCCCTCCTTCTTC

CGCACCGTGCCCAGCGACCGTGTGCAGCTGACGGCCGCCGCGGAGCTGCTGCAGGAGTTC

GGCTGGAACTGGGTGGCCGCCCTGGGCAGCGACGACGAGTACGGCCGGCAGGGCCTGAGC

ATCTTCTCGGCCCTGGCCGCGGCACGCGGCATCTGCATCGCGCACGAGGGCCTGGTGCCGC

TGCCCCGTGCCGATGACTCGCGGCTGGGGAAGGTGCAGGACGTCCTGCACCAGGTGAACC

AGAGCAGCGTGCAGGTGGTGCTGCTGTTCGCCTCCGTGCACGCCGCCCACGCCCTCTTCAA

CTACAGCATCAGCAGCAGGCTCTCGCCCAAGGTGTGGGTGGCCAGCGAGGCCTGGCTGAC

CTCTGACCTGGTCATGGGGCTGCCCGGCATGGCCCAGATGGGCACGGTGCTTGGCTTCCTC

CAGAGGGGTGCCCAGCTGCACGAGTTCCCCCAGTACGTGAAGACGCACCTGGCCCTGGCC

ACCGACCCGGCCTTCTGCTCTGCCCTGGGCGAGAGGGAGCAGGGTCTGGAGGAGGACGTG

GTGGGCCAGCGCTGCCCGCAGTGTGACTGCATCACGCTGCAGAACGTGAGCGCAGGGCTA

AATCACCACCAGACGTTCTCTGTCTACGCAGCTGTGTATAGCGTGGCCCAGGCCCTGCACA

ACACTCTTCAGTGCAACGCCTCAGGCTGCCCCGCGCAGGACCCCGTGAAGCCCTGGCAGCT

CCTGGAGAACATGTACAACCTGACCTTCCACGTGGGCGGGCTGCCGCTGCGGTTCGACAGC

AGCGGAAACGTGGACATGGAGTACGACCTGAAGCTGTGGGTGTGGCAGGGCTCAGTGCCC

AGGCTCCACGACGTGGGCAGGTTCAACGGCAGCCTCAGGACAGAGCGCCTGAAGATCCGC

TGGCACACGTCTGACAACCAGAAGCCCGTGTCCCGGTGCTCGCGGCAGTGCCAGGAGGGC

CAGGTGCGCCGGGTCAAGGGGTTCCACTCCTGCTGCTACGACTGTGTGGACTGCGAGGCG

GGCAGCTACCGGCAAAACCCAGACGACATCGCCTGCACCTTTTGTGGCCAGGATGAGTGG

TCCCCGGAGCGAAGCACACGCTGCTTCCGCCGCAGGTCTCGGTTCCTGGCATGGGGCGAGC

CGGCTGTGCTGCTGCTGCTCCTGCTGCTGAGCCTGGCGCTGGGCCTTGTGCTGGCTGCTTT

GGGGCTGTTCGTTCACCATCGGGACAGCCCACTGGTTCAGGCCTCGGGGGGGCCCCTGGCC

TGCTTTGGCCTGGTGTGCCTGGGCCTGGTCTGCCTCAGCGTCCTCCTGTTCCCTGGCCAGCC

CAGCCCTGCCCGATGCCTGGCCCAGCAGCCCTTGTCCCACCTCCCGCTCACGGGCTGCCTG

AGCACACTCTTCCTGCAGGCGGCCGAGATCTTCGTGGAGTCAGAACTGCCTCTGAGCTGGG

CAGACCGGCTGAGTGGCTGCCTGCGGGGGCCCTGGGCCTGGCTGGTGGTGCTGCTGGCCA
```

```
-continued
TGCTGGTGGAGGTCGCACTGTGCACCTGGTACCTGGTGGCCTTCCCGCCGGAGGTGGTGAC

GGACTGGCACATGCTGCCCACGGAGGCGCTGGTGCACTGCCGCACACGCTCCTGGGTCAG

CTTCGGCCTAGCGCACGCCACCAATGCCACGCTGGCCTTTCTCTGCTTCCTGGGCACTTTCC

TGGTGCGGAGCCAGCCGGGCTGCTACAACCGTGCCCGTGGCCTCACCTTTGCCATGCTGGC

CTACTTCATCACCTGGGTCTCCTTTGTGCCCCTCCTGGCCAATGTGCAGGTGGTCCTCAGGC

CCGCCGTGCAGATGGGCGCCCTCCTGCTCTGTGTCCTGGGCATCCTGGCTGCMCCACCT

GCCCAGGTGTTACCTGCTCATGCGGCAGCCAGGGCTCAACACCCCCGAGTTCTTCCTGGGA

GGGGGCCCTGGGGATGCCCAAGGCCAGAATGACGGGAACACAGGAAATCAGGGGAAACA

TGAGTGA hT1R3 conceptual translation (SEQ ID NO 4)
                                                   (SEQ ID NO 4)
MLGPAVLGLSLWALLHPGTGAPLCLSQQLRMKGDYVLGGLFPLGEAEEAGLRSRTRPSSPVCT

RFSSNGLLWALAMKMAVEEINNKSDLLPGLRLGYDLFDTCSEPVVAMKPSLMFLAKAGSRDI

AAYCNYTQYQPRVLAVIGPHSSELAMVTGKFFSFFLMPHYGASMELLSARETFPSFFRTVPSDR

VQLTAAAELLQEFGWNWVAALGSDDEYGRQGLSIFSALAAARGICIAHEGLVPLPRADDSRLG

KVQDVLHQVNQSSVQVVLLFASVHAAHALFNYSISSRLSPKVWVASEAWLTSDLVMGLPGM

AQMGTVLGFLQRGAQLHEFPQYVKTHLALATDPAFCSALGEREQGLEEDVVGQRCPQCDCIT

LQNVSAGLNHHQTFSVYAAVYSVAQALHNTLQCNASGCPAQDPVKPWQLLENWNLTFHVG

GLPLRFDSSGNVDMEYDLKLWVWQGSVPRLHDVGRFNGSLRTERLKIRWHTSDNQKPVSRCS

RQCQEGQVRRVKGFHSCCYDCVDCEAGSYRQNPDDIACTFCGQDEWSPERSTRCFRRRSRFLA

WGEPAVLLLLLLLSLALGLVLAALGLFVHHRDSPLVQASGGPLACFGLVCLGLVCLSVLLFPG

QPSPARCLAQQPLSHLPLTGCLSTLFLQAAEIFVESELPLSWADRLSGCLRGPWAWLVVLLAML

VEVALCTWYLVAFPPEVVTDWHMLPTEALVHCRTRSWVSFGLAHATNATLAFLCFLGTFLVR

SQPGCYNRARGLTFAMLAYFITWVSFVPLLANVQVVLRPAVQMGALLLCVLGILAAFHLPRCY

LLMRQPGLNTPEFFLGGGPGDAQGQNDGNTGNQGKHE
```

Example 2—rT1R3 and mT1R3

Segments of the rat and mouse T1R3 genes were isolated by PCR amplification from genomic DNA using degenerate primers based on the human T1R3 sequence. The degenerate primers SAP077 (5'-CGNTTYYTNGCNTGGGGN-GARCC-3'; SEQ ID NO 5) and SAP079 (5'-CGNGC-NCGRTTRTARCANCCNGG-3'; SEQ ID NO 6) are complementary to human T1R3 residues RFLAWGEPA (corresponding to SEQ ID NO 7) and PGCYNRAR (corresponding to SEQ ID NO 8), respectively. The PCR products were cloned and sequenced. Plasmid SAV115 carries a cloned segment of the mouse T1R3 gene, and SAV118 carries a segment of the rat gene. These sequences, shown below, clearly represent the rodent counterparts of human T1R3, since the mouse segment is 74% identical to the corresponding segment of human T1R3, and the rat segment is 80% identical to the corresponding segment of human T1R3. The mouse and rat segments are 88% identical. No other database sequences are more than 40% identical to these T1R3 segments.

```
SAV115 mouse T1R3 segment in sense orientation (sequence
corresponding to degenerate primer removed) (SEQ ID NO 9)
                                                      (SEQ ID NO 9)
  GTGCTGTCACTCCTCCTGCTGCTTTGCCTGGTGCTGGGTCTAGCACTGGCTGCTCTGGGGCT

CTCTGTCCACCACTGGGACAGCCCTCTTGTCCAGGCCTCAGGCGGCTCACAGTTCTGCTTT

GGCCTGATCTGCCTAGGCCTCTTCTGCCTCAGTGTCCTTCTGTTCCCAGGACGGCCAAGCTC

TGCCAGCTGCCTTGCACAACAACCAATGGCTCACCTCCCTCTCACAGGCTGCCTGAGCACA

CTCTTCCTGCAAGCAGCTGAGACCTTTGTGGAGTCTGAGCTGCCACTGAGCTGGGCAAACT

GGCTATGCAGCTACCTTCGGGACTCTGGCCTGCTAGTGGTACTGTTGGCCACTTTTGTGGA

GGCAGCACTATGTGCCTGGTATTTGACCGCTTCACCAGAAGTGGTGACAGACTGGTCAGTG
``` mT1R3 segment, conceptual translation (SEQ ID NO 10)

(SEQ ID NO 10)
VLSLLLLLCLVLGLALAALGLSVHHWDSPLVQASGGSQFCFGLICLGLFCLSVLLFPGRPSSASC

LAQQPMAHLPLTGCLSTLFLQAAETFVESELPLSWANWLCSYLRDSGLLVVLLATFVEAALCA

WYLTASPEVVTDWSVLPTEVLEHCHVRSWVNLGLVHITNAMVAFLCFLGTFLVQDQ

SAV118 rat T1R3 segment in sense orientation (sequence corresponding
to degenerate primer removed) (SEQ ID NO 11)

(SEQ ID NO 11)
GTGCTGTCACTTCTCCTGCTGCTTTGCCTGGTGCTGGGCCTGACACTGGCTGCCCTGGGGC

TCTTTGTCCACTACTGGGACAGCCCTCTTGTTCAGGCCTCAGGTGGGTCACTGTTCTGGTTT

GGCCTGATCTGCCTAGGCCTCTTCTGCCTCAGTGTCCTTCTGTTCCCAGGACGACCACGCTC

TGCCAGCTGCCTTGCCCAACAACCAATGGCTCACCTCCCTCTCACAGGCTGCCTGAGCACA

CTCTTCCTGCAAGCAGCCGAGATCTTTGTGGAGTCTGAGCTGCCACTGAGTTGGGCAAACT

GGCTCTGCAGCTACCTTCGGGGCCCCTGGGCTTGGCTGGTGGTACTGCTGGCCACTCTTGT

GGAGGCTGCACTATGTGCCTGGTACTTGATGGCTTTCCCTCCAGAGGTGGTGACAGATTGG

CAGGTGCTGCCCACGGAGGTACTGGAACACTGCCGCATGCGTTCCTGGGTCAGCCTGGGCT

TGGTGCACATCACCAATGCAGGGGTAGCTTTCCTCTGCTTTCTGGGCACTTTCCTGGTACA

AAGCCAG rT1R3 segment, conceptual translation (SEQ ID NO 12)

(SEQ ID NO 12)
VLSLLLLLCLVLGLTLAALGLFVHYWDSPLVQASGGSLFCFGLICLGLFCLSVLLFPGRPRSASC

LAQQPMAHLPLTGCLSTLFLQAAEIFVESELPLSWANWLCSYLRGPWAWLVVLLATLVEAAL

CAWYLMAFPPEVVTDWQVLPTEVLEHCRMRSWVSLGLVHITNAGVAFLCFLGTFLVQSQ

Example 3—Cloning of rT1R3

The mT1R3 and rT1R3 fragments identified above as SEQ ID NOs 9 and 11 were used to screen a rat taste tissue-derived cDNA library. One positive clone was sequenced and found to contain the full-length rT1R3 sequence presented below as SEQ ID NO 13. Sequence comparison to the mT1R3 and rT1R3 partial sequences and to the full-length hT1R3 sequence established that this cDNA represents the rat counterpart to hT1R3. For example, the pairwise amino acid identity between rT1R3 and hT1R3 is approximately 72%, whereas the most related annotated sequence in public DNA sequence data banks is only approximately 33% identical to rT1R3.

rT1R3 predicted cds (SEQ. ID NO. 13)

(SEQ ID NO 13)
ATGCCGGGTTTGGCTATCTTGGGCCTCAGTCTGGCTGCTTTCCTGGAGCTTGGGATGGGGT

CCTCTTTGTGTCTGTCACAGCAATTCAAGGCACAAGGGGACTATATATTGGGTGGACTATT

TCCCCTGGGCACAACTGAGGAGGCCACTCTCAACCAGAGAACACAGCCCAACGGCATCCT

ATGTACCAGGTTCTCGCCCCTTGGTTTGTTCCTGGCCATGGCTATGAAGATGGCTGTAGAG

GAGATCAACAATGGATCTGCCTTGCTCCCTGGGCTGCGACTGGGCTATGACCTGTTTGACA

CATGCTCAGAGCCAGTGGTCACCATGAAGCCCAGCCTCATGTTCATGGCCAAGGTGGGAA

GTCAAAGCATTGCTGCCTACTGCAACTACACACAGTACCAACCCCGTGTGCTGGCTGTCAT

TGGTCCCCACTCATCAGAGCTTGCCCTCATTACAGGCAAGTTCTTCAGCTTCTTCCTCATGC

CACAGGTCAGCTATAGTGCCAGCATGGATCGGCTAAGTGACCGGGAAACATTTCCATCCTT

CTTCCGCACAGTGCCCAGTGACCGGGTGCAGCTGCAGGCCGTTGTGACACTGTTGCAGAAT

TTCAGCTGGAACTGGGTGGCTGCCTTAGGTAGTGATGATGACTATGGCCGGGAAGGTCTG

AGCATCTTTTCTGGTCTGGCCAACTCACGAGGTATCTGCATTGCACACGAGGGCCTGGTGC

-continued

```
CACAACATGACACTAGTGGCCAACAATTGGGCAAGGTGGTGGATGTGCTACGCCAAGTGA
ACCAAAGCAAAGTACAGGTGGTGGTGCTGTTTGCATCTGCCCGTGCTGTCTACTCCCTTTT
TAGCTACAGCATCCTTCATGACCTCTCACCCAAGGTATGGGTGGCCAGTGAGTCCTGGCTG
ACCTCTGACCTGGTCATGACACTTCCCAATATTGCCCGTGTGGGCACTGTTCTTGGGTTTCT
GCAGCGCGGTGCCCTACTGCCTGAATTTTCCCATTATGTGGAGACTCGCCTTGCCCTAGCT
GCTGACCCAACATTCTGTGCCTCCCTGAAAGCTGAGTTGGATCTGGAGGAGCGCGTGATGG
GGCCACGCTGTTCACAATGTGACTACATCATGCTACAGAACCTGTCATCTGGGCTGATGCA
GAACCTATCAGCTGGGCAGTTGCACCACCAAATATTTGCAACCTATGCAGCTGTGTACAGT
GTGGCTCAGGCCCTTCACAACACCCTGCAGTGCAATGTCTCACATTGCCACACATCAGAGC
CTGTTCAACCCTGGCAGCTCCTGGAGAACATGTACAATATGAGTTTCCGTGCTCGAGACTT
GACACTGCAGTTTGATGCCAAAGGGAGTGTAGACATGGAATATGACCTGAAGATGTGGGT
GTGGCAGAGCCCTACACCTGTACTACATACTGTAGGCACCTTCAACGGCACCCTTCAGCTG
CAGCACTCGAAAATGTATTGGCCAGGCAACCAGGTGCCAGTCTCCCAGTGCTCCCGGCAGT
GCAAAGATGGCCAGGTGCGCAGAGTAAAGGGCTTTCATTCCTGCTGCTATGACTGTGTGG
ACTGCAAGGCAGGGAGCTACCGGAAGCATCCAGATGACTTCACCTGTACTCCATGTGGCA
AGGATCAGTGGTCCCCAGAAAAAAGCACAACCTGCTTACCTCGCAGGCCCAAGTTTCTGGC
TTGGGGGGAGCCAGCTGTGCTGTCACTTCTCCTGCTGCTTTGCCTGGTGCTGGGCCTGACA
CTGGCTGCCCTGGGGCTCYTTGTCCACTACTGGGACAGCCCTCTTGTTCAGGCCTCAGGTG
GGTCACTGTTCTGCTTTGGCCTGATCTGCCTAGGCCTCTTCTGCCTCAGTGTCCTTCTGTTC
CCAGGACGACCACGCTCTGCCAGCTGCCTTGCCCAACAACCAATGGCTCACCTCCCTCTCA
CAGGCTGCCTGAGCACACTCTTCCTGCAAGCAGCCGAGATCTTTGTGGAGTCTGAGCTGCC
ACTGAGTTGGGCAAACTGGCTCTGCAGCTACCTTCGGGGCCCCTGGGCTTGGCTGGTGGTA
CTGCTGGCCACTCTTGTGGAGGCTGCACTATGTGCCTGGTACTTGATGGCTTTCCCTCCAG
AGGTGGTGACAGATTGGCAGGTGCTGCCCACGGAGGTACTGGAACACTGCCGCATGCGTT
CCTGGGTCAGCCTGGGCTTGGTGCACATCACCAATGCAGTGTTAGCTTTCCTCTGCTTTCTG
GGCACTTTCCTGGTACAGAGCCAGCCTGGTCGCTATAACCGTGCCCGTGGCCTCACCTTCG
CCATGCTAGCTTATTTCATCATCTGGGTCTCTTTTGTGCCCCTCCTGGCTAATGTGCAGGTG
GCCTACCAGCCAGCTGTGCAGATGGGTGCTATCTTATTCTGTGCCCTGGGCATCCTGGCCA
CCTTCCACCTGCCCAAATGCTATGTACTTCTGTGGCTGCCAGAGCTCAACACCCAGGAGTT
CTTCCTGGGAAGGAGCCCCAAGGAAGCATCAGATGGGAATAGTGGTAGTAGTGAGGCAAC
TCGGGGACACAGTGAATGA
``` rT1R3 conceptual translation (SEQ. ID NO. 14)

(SEQ ID NO 14)
MPGLAILGLSLAAFLELGMGSSLCLSQQFKAQGDYILGGLFPLGTTEEATLNQRTQPNGILCTRF
SPLGLFLAMAMKMAVEEINNGSALLPGLRLGYDLFDTCSEPVVTMKPSLMFMAKVGSQSIAA
YCNYTQYQPRVLAVIGPHSSELALITGKFFSFFLMPQVSYSASMDRLSDRETFPSFFRTVPSDRV
QLQAVVTLLQNFSWNWVAALGSDDDYGREGLSIFSGLANSRGICIAHEGLVPQHDTSGQQLG
KVVDVLRQVNQSKVQVVVLFASARAVYSLFSYSILHDLSPKVWVASESWLTSDLVMTLPNIA
RVGTVLGFLQRGALLPEFSHYVETRLALAADPTFCASLKAELDLEERVMGPRCSQCDYIMLQN
LSSGLMQNLSAGQLHHQIFATYAAVYSVAQALHNTLQCNVSHCHTSEPVQPWQLLENMYNM
SFRARDLTLQFDAKGSVDMEYDLKMWVWQSPTPVLHTVGTFNGTLQLQHSKMYWPGNQVP

-continued

```
VSQCSRQCKDGQVRRVKGFHSCCYDCVDCKAGSYRKHPDDFTCTPCGKDQWSPEKSTTCLPR

RPKFLAWGEPAVLSLLLLLCLVLGLTLAALGLFVHYWDSPLVQASGGSLFCFGLICLGLFCLSV

LLFPGRPRSASCLAQQPMAHLPLTGCLSTLFLQAAEIFVESELPLSWANWLCSYLRGPWAWLV

VLLATLVEAALCAWYLMAFPPEVVTDWQVLPTEVLEHCRMRSWVSLGLVHITNAVLAFLCFL

GTFLVQSQPGRYNRARGLTFAMLAYFIIWVSFVPLLANVQVAYQPAVQMGAILFCALGILATF

HLPKCYVLLWLPELNTQEFFLGRSPKEASDGNSGSSEATRGHSE
```

Example 4—Expression of mT1R3

The above described mouse T1R3 fragment contained in SAV115 was PCR amplified using M13forward and M13reverse primers and then gel purified. The T1R3 DNA template was placed into an in vitro transcription labeling reaction where Digoxigenin labeled UTP was incorporated into an antisense cRNA probe. This probe was hybridized to adult mouse taste tissue containing cicumvallate papillae. The T1R3 in situ hybridization and detection were performed following the protocol of Schaeren-Wiemers et al., *Histochemistry*, 100:431-400 (1993). Briefly, fresh frozen mouse tongue was sectioned at 14 μm and prepared for hybridization. 200 ng/mL of the antisense Digoxigenin T1R3 probe was hybridized for 14 hours at 72° C. Posthybridization consisted of a 0.2×SSC wash at 72° C. Digoxigenin detection was accomplished by incubation with 1:5000 dilution of anti-DIG Alkaline Phosphatase antibody followed by a 12-hour reaction of the phosphatase in NBT/BCIP. FIG. 1 shows T1R3 gene expression in taste buds of mouse circumvallate papillae.

Example 5—hT1R1

The human ortholog (Database accession no. AL159177) of a rat taste receptor, designated rT1R1, is provided below as SEQ ID NO 15. Predicted cds are indicated in bold and some intronic sequence intervals are denoted as runs of N. The nucleotide and conceptually-translated hT1R1 sequences are also described herein as SEQ ID NO 16 and 17, respectively hT1R1 genomic DNA (SEQ ID NO 15)

(SEQ ID NO 15)
```
GAGAATCTCGCGAGATCCCGTCGGTCCGCCCCGCTGCCCTCCCAGCTGCCGAAAAGAGGG

GCCTCCGAGCCGCCGGCGCCCTCTGCCGGCAACCTCCGGAAGCACACTAGGAGGTTCCAG

CCGATCTGGTCGAGGGGCTCCACGGAGGACTCCATTTACGTTACGCAAATTCCCTACCCA

GCCGGCCGGAGAGAGAAAGCCAGAAACCTCGCGACCAGCCATGGGCCACCTCTCCGGAAA

AACACCGGGATATTTTTTTCTCCTGCAGAAAAAGCTTTAGGATTGGCAGTTTAAACAAAA

CATGTCTATTTGCATACCTTCGGTTTGCATGCATTTGTTTCGAAGTGAGCAACCCTGGGTA

ACAAGGCGAAAGTATATGACAATTTGCTCAGAATCTTAATGTCAGAAAACTGGAGACTGG

GGCAGGGGGTGTCGACTCAAAGCTGTGTCTCATTTAGTAAACTGAGGCCCAGGTAAAAA

GTTCTGAAACCTCGCAACACCCGGAGAAATTGTGTTCCAGCCTCCCACCTCGCCCCAAAT

GCCAGAGCTCCTTTTCTAAGCCAGGTQAAGTCACAGAGCGTGGACAGAACCCACAACCGT

CCAGAGGAAGGGTCACTGGGTGCCACCTGGTTTGCATCTGTGCCTTCGTCCTGCCCAGTTC

CTGAGTGGGACCGCAGGCCCGGAATGTCAAGGCAAACAGTCCTGCTTCAGCCACTGGGCT

CCAGTCCCACCCCTTTTGGGGGCCTGAAGTTAGGAAGCATCCGGCAGCTGCCTTCTATTTA

AGCAACTGGCCTCCTTAGAGGCCACTCCTTGGCCATGCCAGGCGCGGGCATCTGGCCAGCA

TGCTGCTCTGCACGGCTCGCCTGGTCGGCCTGCAGCTTCTCATTTCCTGCTGCTGGG

CCTTTGCCTGCCATAGCACGGAGTCTTCTCCTGACTTCACCCTCCCCGGAGATTACCT

CCTGGCAGGCCTGTTCCCTCTCCATTCTGGCTGTCTGCAGGTGAGGCACAGACCCGA

GGTGACCCTGTGTGACAGGTGAGTGAGGGGCCAGCAGAGCCACACTTAGTGGGACCCCT

GGCTATAGGGCCCCTCTGGCTGCCATCCTCCAAACAGGACCTTGCCTCTGCCTTTGCCCCTT

GAACTGTCCCCAGGCCTTGTTCATCAATCCACTTGCCACCTAAGTGCTGGCTAGACCTTCCT

AGACACTTCGGCCAGTTTCCAATTATTTCACCCTTGCTGTTAGAATGTNNNNNNNNNNNNNN

NNNNNNNNNNNNNNNNNNNNNNNNNNNNNNNNNNNNNNNNNNNAATTCCTTAAACTAAATTTCTC
```

-continued

```
ACTTTCTCTCTCTCTCTGGAAAACACTGACTAATGTAGCAGGTTTCTCTGCTCCAGGACTTC
AGGACCTTTTCGATGCTAATAAGTTTCTCCATCAGGGCCAGCTTGTTCCTCCTACTGAGCTT
GAGAGCCCTTGTTGAAGTTGTGGTTTGGGGGACTGGACCGATGACCTCAAAGGTTCCCTTT
GCTCCCAAGCCTCAGAGTCTAGGAGGCCAGAGGGTCTCAGCAGGCCTTTGTCCTTCTCAGC
TGTCTCTTACTGGCTTTCTCCACAGGTCTTGTAGCTTCAATGAGCATGGCTACCACCTCT
TCCAGGCTATGCGGCTTGGGGTTGAGGAGATAAACAACTCCACGGCCCTGCTGCCCA
ACATCACCCTGGGGTACCAGCTGTATGATGTGTGTTCTGACTCTGCCAATGTGTATGC
CACGCTGAGAGTGCTCTCCCTGCCAGGGCAACACCACATAGAGCTCCAAGGAGACCT
TCTCCACTATTCCCCTACGGTGCTGGCAGTGATTGGGCCTGACAGCACCAACCGTGC
TGCCACCACAGCCGCCCTGCTGAGCCCTTTCCTGGTGCCCATGGTAAGCTGGAGCCTC
AGACCTTTGCCCATCTCCCTTCAGGCAAGTCTGGGNNNNNNNNNNNNNNNNNNNNNNNNNN
NNNNNNNNNNNNNNNNNNNNNNNNNGCCACCATGCCCGGCTAATTTTTTGTATTTTTAG
TAGAGACGGGGTTTCACCGTGTTAGCCAGGCTGGTCGCAAACTCCTAACCTCGTGATCCAC
CCACCTCGGCCTCCCAATGTGCTGGGATTACAGGTGTGAGCCACTGCACCCGGCCATAATG
TATTAATATAATAAAATAATTATACAACTCACCATAATGTAGAATCAGTGGGAGCCCTGAG
CTTGTTTTCCTACAACTAGATGGTCCCATCTGGGGGTGATGGGAGACAGTGACAGATCATC
AGACATTAGATTCTCATAAGTAGCGTGCAACCCAGATCCCTCGCATGTGCAGTTCACAGTA
GGGTTCAAGCTCCTACAAGAATCTGATGCTGCTGCTGATCTGACAGGAGGGGA6CAGCTG
TAAATACAGATGAAGCTTCGCTTACTCACCAGCTGCTCACCTCCTCCTGTGAGGCCCGGTT
CCTAACAGGCCACTGACCTAACTTCTGCCCTGACCTACACATGCTTCTCTTCTTCCTTGCAA
ACTGCCTCCAGTGGAAGTCCCTGAAGGTCCCCAAACACACGGGACTATTTCACTCCTATGC
AGGTTTTGTCTCCTTTGCTTGGAATGCATCCCCTCACCCCTTGTCCCCAGGCAGATTCCCAC
CCCTCCCCCAGAACCTGCCCCAGTGGAGCCTTCGCAGGTGATTTGTCAGTTTCACAGGCTG
AGGGGTGCTCTCCTGGTCTCCCCGGCTCCCTGTATCCCCACACCCAGCACAGGGCCAGGCA
CTGGGGGGGCCTTCAGTGGAGACTGAAATGGCTGAACGGGACCTCCCATAGATTAGCTAT
GCGGCCAGCAGCGAGACGCTCAGCGTGAAGCGGCAGTATCCCTCTTTCCTGCGCACC
ATCCCCAATGACAAGTACCAGGTGGAGACCATGGTGCTGCTGCTGCAGAAGTTCGGG
TGGACCTGGATCTCTCTGGTTGGCAGCAGTGACGACTATGGGCAGCTAGGGGTGCAG
GCACTGGAGAACCAGGCCACTGGTCAGGGGATCTGCATTGCTTTCAAGGACATCATG
CCCTTCTCTGCCCAGGTGGGCGATGAGAGGATGCAGTGCCTCATGCGCCACCTGGCC
CAGGCCGGGGCCACCGTCGTGGTTGTTTTTTCCAGCCGGCAGTTGGCCAGGGTGTTT
TTCGAGTCCGTGGTGCTGACCAACCTGACTGGCAAGGTGTGGGTCGCCTCAGAAGCC
TGGGCCCTCTCCAGGCACATCACTGGGGTGCCCGGGATCCAGCGCATTGGGATGGTG
CTGGGCGTGGCCATCCAGAAGAGGGCTGTCCCTGGCCTGAAGGCGTTTGAAGAAGCC
TATGCCCGGGCAGACAAGAAGGCCCCTAGGCCTTGCCACAAGGGCTCCTGGTGCAGC
AGCAATCAGCTCTGCAGAGAATGCCAAGCTTTCATGGCACACACGATGCCCAAGCTC
AAAGCCTTCTCCATGAGTTCTGCCTACAACGCATACCGGGCTGTGTATGCGGTGGCC
CATGGCCTCCACCAGCTCCTGGGCTGTGCCTCTGGAGCTTGTTCCAGGGGCCGAGTC
TACCCCTGGCAGGTAAGAGAGCCCACCCCAGCACCTCCTGTCAGGGAGAACAGCCAATCC
TGAGATGAGCAGAGTGGGCACTCTCCGGTCACTCTAAATGCCAAGGGGGATAAATGCCAC
TAACTTGAGGTTTTTTGTTTTGTTTTGTTTTGTTTTTTGAGACAGTCTGGCTCTGTCACCCA
```

```
GGCTGCAGTGTAGTGATGCGATCTCGGCTCTCTGCAACTTCCACCTCCTGGGTTCAAGTGA

TTCTCTTGCCTCGGCCTCCTGAGTAGCTGGGATTACAGGCACCCACCACCATGCCTGGATA

ATTTTTCTTTTCTTTTTTTTTTTTTTGAGATAGAGTCTCGCTCTGTTGCCCAGGCTGGAATGC

AGTGGTGCGATCTTGGCTCACTGTGAGCTCCGCCTCCCAGGTTCACTCCATTCCCCTGCCTC

AGCCTCCCAAGTAGGTGGGACTACGGGCGCCCGCCACCACGCCCAGCTAATTTTTTTGTA

TTTTGAGTAGAGACGGGGTTTCACCATGTTAGCCAGGATGGTCTCAATCTCCTGACCTTGT

CATCCGCCCACCTCGTCCTCCCAAAGTGCTGGGATTACAGGCGTGAGCCACCGCACCCGGC

CTAATTTTTGTATTTTTAGTAGAGATGGGGTTTCACCATGTTGGCCAGGCTGGTCTCGAAC

TCCTGGCATCAAGTGATCCTCCTGCTTCGGCCTCCCAAAGTGCTGGGATTACAGGCATTAG

CTCTCTTCTCTTAGACAGATCTTTCTCTCTGATCCTTGCCTTCTCTCACCCACTGTGTCTTGG

AAGTGTCAAGTGATAAGATCCAGGGCTAAAACTGTCTGTAAAGGAGTGTTTGTTAGAGGC

CTCCTCTCAGGAGGTTGGTGGGAAGATTGAGGGGCTTCCTAAGAAGGAAGGGACGAGAC

CTTCCTGATGGGCTGAAACCACCAGGACGGAAACCCAGGAAGGCCCCAGGCCCTTGCTTCT

GGGACCATGTGGGTCTGTGCTGTCTGTGGTGGCTTCATGATACGCGTTTCTTTCAGCTTTT

GGAGCAGATCCACAAGGTGCATTTCCTTCTACACAAGGACACTGTGGCGTTTAATGA

CAACAGAGATCCCCTCAGTAGCTATAACATAATTGCCTGGGACTGGAATGGACCCAA

GTGGACCTTCACGGTCCTCGGTTCCTCCACATGGTCTCCAGTTCAGCTAAACATAAAT

GAGACCAAAATCCAGTGGCACGGAAAGGACAACCAGGTAATGGGGATGTGGCTACTCA

CCATGTAACTGGCTTATGGGCAACCTAGAGCCTGGGGGTGATGCTGACACAGTGTACAGG

GAGCAGGAGGGGGCCCCAGGGGTCCAGCTGCCACCACTCTACCCATCCTGGCCAGGGAA

GCAGGGAAGACACTCCGTAGGCGAGTGTGCAGATGCCCTGGGGCGGAAGTTCACACGACC

AGGGGCCCTGCCCTGGGAGTGAGCCCTGAGGGCAGATGCACAGAGATTCTGTTTTCTGTTC

CACATGTGAGCTGTCCTTTGACTTGGGCCCCTACGTGTGGCCCCTCTGGCTTCTTACAGGT

GCCTAAGTCTGTGTGTTCCAGCGACTGTCTTGAAGGGCACCAGCGAGTGGTTACGGG

TTTCCATCACTGCTGCTTTGAGTGTGTGCCCTGTGGGGCTGGGACCTTCCTCAACAAG

AGTGGTGAGTGGGCAATGGAGCAGGCGAGCTACCCAGCACTCCCGGGGGCTGCACGGTGG

AGGGAGGGCCTCCCTTGGGCCCCATGTGCCCTGCCCCAGAACCAAGGCCCAGTCACTGGG

CTGCCAGTTAGCTTCAGGTTGGAGGACACCTGCTACCAGACAGAATTCTGATCAAGAGAAT

CAGCCACTGGGTGCGGTGGCTCATGCCTGTAATCCCAGCACTTTGGGAGGCTGAGGCGGG

TGGATCACTTGAGGTCGGGAGTTCGAGACCAGCCTGGCCAACATGGTGAAACCCCATCTCT

ACCAAAAATATAAAAAATTAGCTGGGTGTGGTGGCGCGTGCCTGTAATCCCAGCTACTCG

GGAGGCTGAGGCAGGAGAATCACTTGAACCCAGGAGGCGGAGGTTGCAGTGAGCCAAGA

TGCATTCCAGCCTGGACCACAAAGCGAGAATTCGTCCCCCCAAAAAAAGAAAGGAGGCCG

GGCGCGGTGGCTCACACCTGTAATCCCAGCACTTTGGGAGGCCGAGGTGGGTGGATCACC

TGAGGTCAGGAGTTCGAGACCAGCCTGACCAACATGGTGAAACCCCATCTCTACTAAAAA

TACAAAAAAAGTTAGCCGGGCGTTGTGGCGTGTGCCTGTAATTCCAGCTACTCGGGAGGCT

GAGGCAGGAGAATTGCTTGAACCCGGGAGGCGGAGGTTGCAGTGAGCCAAGATTGCACCA

TTGCACTCCAGCCTGGGCGACAAGAGAAAAACTCTGTCTCAAAAAAAAAGAAAGAAAGAA

AGAATTAGCCAACTGAAAGCCTTAGACTGAGGTGTGTCCTCTGTTAGAGAGCTGTCATCAC

AACTCCTACAAAAGCAGTCGTATCCTGAATTCAACCTCTTTCTCTAAATGAATATAGCTAT
```

-continued

```
TGTTCCCTTTGTGCCCTCTTGTCCTACTGTCCCTTCTGTTGCCCATGCCAAAGACAGCTAGC

TCCTTGAACAGCTTGGCCTGAATACAGATACTAGCGTGTCTGCAGCAGAGAAAAAAACAG

CATTCCCCATCCAGAAATGCAAGGTCAAGAACAGAGAGCAAATTAGGTAGCTAAGGACTC

AGGTCCTTAGTTGGTGTCCAGGGGCCACATTCTTTCCTTTCACCATCTCTGTAGGGACAGG

AATACTTCCCTTCTGTCCTCAGAGGGTCAGGACTCAGAGAAACCACAGAGCAGCAGCTCA

GGAAAGTGGTTCATGGAAATGCTGGCAAGAGAGAGGGGTTACAATGCCCTCCCTTGGGAG

CAGGCTGCTCCCATCAGATCGTAACCTCTCTGGTATGTGGGCAGAGCTACCAGGTTAAGGT

CCTCCCTAGGGTTTGCAAAACCCTCATGGGATCATGAGCCATACAGAACCGACCTGTGTGT

CTCCAGAGTCTGTAATTAACACAGGCATTTTGAGGAAATGCGTGGCCTCAGGCCCCACTCC

CGGCTACCCCCATCCCACTATGCCTAGTATAGTCTAGCTGCCCTGGTACAATTCTCCCAGT

ATCTTGCAGGCCCCTATTTCCTATTCCTACTCTGCTCATCTGGCTCTCAGGAACCTTCTTGG

CCTTCCCTTTCAGACCTCTACAGATGCCAGCCTTGTGGGAAAGAAGAGTGGGCACCTG

AGGGAAGCCAGACCTGCTTCCCGCGCACTGTGGTGTTTTTGGCTTTGCGTGAGCACA

CCTCTTGGGTGCTGCTGGCAGCTAACACGCTGCTGCTGCTGCTGCTGCTTGGGACTG

CTGGCCTGTTTGCCTGGCACCTAGACACCCCTGTGGTGAGGTCAGCAGGGGCCGCC

TGTGCTTTCTTATGCTGGGCTCCCTGGCAGCAGGTAGTGGCAGCCTCTATGGCTTCTT

TGGGGAACCCACAAGGCCTGCGTGCTTGCTACGCCAGGCCCTCTTTGCCCTTGGTTT

CACCATCTTCCTGTCCTGCCTGACAGTTCGCTCATTCCAACTAATCATCATCTTCAAG

TTTTCCACCAAGGTACCTACATTCTACCACGCCTGGGTCCAAAACCACGGTGCTGGCC

TGTTTGTGATGATCAGCTCAGCGGCCCAGCTGCTTATCTGTCTAACTTGGCTGGTGGT

GTGGACCCCACTGCCTGCTAGGGAATACCAGCGCTTCCCCCATCTGGTGATGCTTGA

GTGCACAGAGACCAACTCCCTGGGCTTCATACTGGCCTTCCTCTACAATGGCCTCCTC

TCCATCAGTGCCTTTGCCTGCAGCTACCTGGGTAAGGACTTGCCAGAGAACTACAAC

GAGGCCAAATGTGTCACCTTCAGCCTGCTCTTCAACTTCGTGTCCTGGATCGCCTTCT

TCACCACGGCCAGCGTCTACGACGGCAAGTACCTGCCTGCGGCCAACATGATGGCTG

GGCTGAGCAGCCTGAGCAGCGGCTTCGGTGGGTATTTTCTGCCTAAGTGCTACGTGA

TCCTCTGCCGCCCAGACCTCAACAGCACAGAGCACTTCCAGGCCTCCATTCAGGACT

ACACGAGGCGCTGCGGCTCCACCTGACCAGTGGGTCAGCAGGCACGGCTGGCAGCCTTC

TCTGCCCTGAGGGTCGAAGGTCGAGCAGGCCGGGGGTGTCCGGGAGGTCTTTGGGCATCG

CGGTCTGGGGTTGGGACGTGTAAGCGCCTGGGAGAGCCTAGACCAGGCTCCGGGCTGCCA

ATAAGAAGTGAAATGCGTATCTGGTCTCCTGTCGTGGGAGAGTGTGAGGTGTAACGGAT

TCAAGTCTGAACCCAGAGCCTGGAAAAGGCTGACCGCCCAGATTGACGTTGCTAGGCAAC

TCCGGAGGCGGGCCCAGCGCCAAAAGAACAGGGCGAGGCGTCGTCCCCGCATCCCATTGG

CCGTTCTCTGCGGGGCCCCGCCCTCGGGGGCCGGAGCTAGAAGCTCTACGCTTCCGAGGCG

CACCTCCTGGCCTGCACGCTTTGACGT
``` hT1R1 predicted cds (SEQ ID NO 16)

(SEQ ID NO 16)
```
ATGCTGCTCTGCACGGCTCGCCTGGTCGGCCTGCAGCTTCTCATTTCCTGCTGCTGGGCCTT

TGCCTGCCATAGCACGGAGTCTTCTCCTGACTTCACCCTCCCCGGAGATTACCTCCTGGCA

GGCCTGTTCCCTCTCCATTCTGGCTGTCTGCAGGTGAGGCACAGACCCGAGGTGACCCTGT
```

-continued

```
GTGACAGGTCTTGTAGCTTCAATGAGCATGGCTACCACCTCTTCCAGGCTATGCGGCTTGG

GGTTGAGGAGATAAACAACTCCACGGCCCTGCTGCCCAACATCACCCTGGGGTACCAGCT

GTATGATGTGTTCTGACTCTGCCAATGTGTATGCCACGCTGAGAGTGCTCTCCCTGCCA

GGGCAACACCACATAGAGCTCCAAGGAGACCTTCTCCACTATTCCCCTACGGTGCTGGCAG

TGATTGGGCCTGACAGCACCAACCGTGCTGCCACCACAGCCGCCCTGCTGAGCCCTTTCCT

GGTGCCCATGATTAGCTATGCGGCCAGCAGCGAGACGCTCAGCGTGAAGCGGCAGTATCC

CTCTTTCCTGCGCACCATCCCCAATGACAAGTACCAGGTGGAGACCATGGTGCTGCTGCTG

CAGAAGTTCGGGTGGACCTGGATCTCTCTGGTTGGCAGCAGTGACGACTATGGGCAGCTA

GGGGTGCAGGCACTGGAGAACCAGGCCACTGGTCAGGGATCTGCATTGCTTTCAAGGAC

ATCATGCCCTTCTCTGCCCAGGTGGGCGATGAGAGGATGCAGTGCCTCATGCGCCACCTGG

CCCAGGCCGGGGCCACCGTCGTGGTTGTTTTTTCCAGCCGGCAGTTGGCCAGGGTGTTTTT

CGAGTCCGTGGTGCTGACCAACCTGACTGGCAAGGTGTGGGTCGCCTCAGAAGCCTGGGC

CCTCTCCAGGCACATCACTGGGGTGCCCGGGATCCAGCGCATTGGGATGGTGCTGGGCGT

GGCCATCCAGAAGAGGGCTGTCCCTGGCCTGAAGGCGTTTGAAGAAGCCTATGCCCGGGC

AGACAAGAAGGCCCCTAGGCCTTGCCACAAGGGCTCCTGGTGCAGCAGCAATCAGCTCTG

CAGAGAATGCCAAGCTTTCATGGCACACACGATGCCCAAGCTCAAAGCCTTCTCCATGAGT

TCTGCCTACAACGCATACCGGGCTGTGTATGCGGTGGCCCATGGCCTCCACCAGCTCCTGG

GCTGTGCCTCTGGAGCTTGTTCCAGGGGCCGAGTCTACCCCTGGCAGCTTTTGGAGCAGAT

CCACAAGGTGCATTTCCTTCTACACAAGGACACTGTGGCGTTTAATGACAACAGAGATCCC

CTCAGTAGCTATAACATAATTGCCTGGGACTGGAATGGACCCAAGTGGACCTTCACGGTCC

TCGGTTCCTCCACATGGTCTCCAGTTCAGCTAAACATAAATGAGACCAAAATCCAGTGGCA

CGGAAAGGACAACCAGGTGCCTAAGTCTGTGTGTTCCAGCGACTGTCTTGAAGGGCACCA

GCGAGTGGTTACGGGTTTCCATCACTGCTGCTTTGAGTGTGTGCCCTGTGGGGCTGGGACC

TTCCTCAACAAGAGTGACCTCTACAGATGCCAGCCTTGTGGGAAAGAAGAGTGGGCACCT

GAGGGAAGCCAGACCTGCTTCCCGCGCACTGTGGTGTTTTTGGCTTTGCGTGAGCACACCT

CTTGGCTGCTGCTGGCAGCTAACACGCTGCTGCTGCTGCTGCTTGGGACTGCTGGCCT

GTTTGCCTGGCACCTAGACACCCCTGTGGTGAGGTCAGCAGGGGCCGCCTGTGCTTTCTT

ATGCTGGGCTCCCTGGCAGCAGGTAGTGGCAGCCTCTATGGCTTCTTTGGGGAACCCACAA

GGCCTGCGTGCTTGCTACGCCAGGCCCTCTTTGCCCTTGGTTTCACCATCTTCCTGTCCTGC

CTGACAGTTCGCTCATTCCAACTAATCATCATCTTCAAGTTTTCCACCAAGGTACCTACATT

CTACCACGCCTGGGTCCAAAACCACGGTGCTGGCCTGTTTGTGATGATCAGCTCAGCGGCC

CAGCTGCTTATCTGTCTAACTTGGCTGGTGGTGTGGACCCCACTGCCTGCTAGGGAATACC

AGCGCTTCCCCCATCTGGTGATGCTTGAGTGCACAGAGACCAACTCCCTGGGCTTCATACT

GGCCTTCCTCTACAATGGCCTCCTCTCCATCAGTGCCTTTGCCTGCAGCTACCTGGGTAAG

GACTTGCCAGAGAACTACAACGAGGCAAATGTGTCACCTTCAGCCTGCTCTTCAACTTCG

TGTCCTGGATCGCCTTCTTCACCACGGCCAGCGTCTACGACGGCAAGTACCTGCCTGCGGC

CAACATGATGGCTGGGCTGAGCAGCCTGAGCAGCGGCTTCGGTGGGTATTTTCTGCCTAAG

TGCTACGTGATCCTCTGCCGCCCAGACCTCAACAGCACAGAGCACTTCCAGGCCTCCATTC

AGGACTACACGAGGCGCTGCGGCTCCACCTGA
``` hT1R1 conceptual translation (SEQ ID NO 17)

(SEQ ID NO 17)
MLLCTARLVGLQLLISCCWAFACHSTESSPDFTLPGDYLLAGLFPLHSGCLQVRHRPEVTLCDR

-continued

SCSFNEHGYHLFQAMRLGVEEINNSTALLPNITLGYQLYDVCSDSANVYATLRVLSLPGQHHIE

LQGDLLHYSPTVLAVIGPDSTNRAATTAALLSPFLVPMISYAASSETLSVKRQYPSFLRTIPNDK

YQVETMVLLLQKFGWTWISLVGSSDDYGQLGVQALENQATGQGICIAFKDIMPFSAQVGDER

MQCLMRHLAQAGATVVVVFSSRQLARVFFESVVLTNLTGKVWVASEAWALSRHITGVPGIQR

IGMVLGVAIQKRAVPGLKAFEEAYARADKKAPRPCHKGSWCSSNQLCRECQAFMAHTMPKL

KAFSMSSAYNAYRAVYAVAHGLHQLLGCASGACSRGRVYPWQLLEQIHKVHFLLHKDTVAF

NDNRDPLSSYNIIAWDWNGPKWTFTVLGSSTWSPVQLNINETKIQWHGKDNQVPKSVCSSDC

LEGHQRVVTGFHHCCFECVPCGAGTFLNKSDLYRCQPCGKEEWAPEGSQTCFPRTVVFLALRE

HTSWVLLAANTLLLLLLGTAGLFAWHLDTPVVRSAGGRLCFLMLGSLAAGSGSLYGFFGEPT

RPACLLRQALFALGFTIFLSCLTVRSFQLIIIFKFSTKVPTFYHAWVQNHGAGLFVMISSAAQLLI

CLTWLVVWTPLPAREYQRFPHLVMLECTETNSLGFILAFLYNGLLSISAFACSYLGKDLPENYN

EAKCVTFSLLFNFVSWIAFFTTASVYDGKYLPAANMMAGLSSLSSGFGGYFLPKCYVILCRPDL

NSTEHFQASIQDYTRRCGST

While the foregoing detailed description has described several embodiments of the present invention, it is to be understood that the above description is illustrative only and not limiting of the disclosed invention. The invention is to be limited only by the claims which follow.

What is claimed:

1. A method of identifying putative human or non-human primate cells which respond to sweet tastants which method comprises (i) identifying human or non-human primate cells which express a polypeptide at least 90% identical to the polypeptide of SEQ ID NO:4 and (ii) modifying said cells identified in (i) to comprise a detectable label or incorporating said identified cells into a composition which comprises a detectable label which detectable label permits the use of such identified cells in assays which screen for compounds which bind to or which modulate the activity of said polypeptide expressed by the identified cells which is at least 90% identical to the polypeptide of SEQ ID NO:4.

2. The method of claim 1 which method comprises identifying human or non-human primate cells which express a polypeptide at least 95% identical to the polypeptide of SEQ ID NO:4.

3. The method of claim 1 which method comprises identifying human or non-human primate cells which express the polypeptide of SEQ ID NO:4.

4. The method of claim 1 wherein the method detects the expression of the polypeptide using an antibody.

5. The method of claim 1 wherein the method detects the expression of the polypeptide using one or more nucleic acid probes or primers.

6. The method of claim 5 which comprises polymerase chain reaction.

7. The method of claim 1 wherein the method identifies such cells in a cell sample derived from one or more of the circumvallate or fungiform papillae, geschmackstreifen, oral cavity, gastrointestinal epithelium, and epiglottis.

8. The method of claim 1 wherein the identified cells are human.

9. The method of claim 2 wherein the identified cells are human.

10. The method of claim 3 wherein the identified cells are human.

11. The method of claim 4 wherein the identified cells are human.

12. The method of claim 5 wherein the identified cells are human.

13. The method of claim 6 wherein the identified cells are human.

14. The method of claim 7 wherein the identified cells are human.

15. The method of claim 7 wherein the identified cells are non-human primate.

* * * * *